(12) United States Patent
Fukuzaki

(10) Patent No.: US 8,174,002 B2
(45) Date of Patent: May 8, 2012

(54) ORGANIC ELECTROLUMINESCENCE DEVICE

(75) Inventor: Eiji Fukuzaki, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 170 days.

(21) Appl. No.: 12/554,338

(22) Filed: Sep. 4, 2009

(65) Prior Publication Data

US 2010/0051928 A1    Mar. 4, 2010

(30) Foreign Application Priority Data

Sep. 4, 2008  (JP) ................. 2008-227269

(51) Int. Cl.
   *H01L 35/24*    (2006.01)
(52) U.S. Cl. ................. 257/40; 257/E51.001
(58) Field of Classification Search .............. 257/40, 257/E51.001
   See application file for complete search history.

(56) References Cited

U.S. PATENT DOCUMENTS

| | | | |
|---|---|---|---|
| 6,821,645 B2 | 11/2004 | Igarashi | |
| 6,962,755 B2 | 11/2005 | Ise | |
| 7,238,437 B2 | 7/2007 | Igarashi | |
| 7,351,395 B1* | 4/2008 | Pez et al. ............... | 423/644 |
| 2005/0260452 A1 | 11/2005 | Ise | |
| 2006/0063033 A1* | 3/2006 | Sohn et al. ............. | 428/690 |
| 2007/0231602 A1 | 10/2007 | Igarashi | |
| 2009/0128008 A1 | 5/2009 | Ise | |

FOREIGN PATENT DOCUMENTS

| | | |
|---|---|---|
| JP | 2001-247859 A | 9/2001 |
| JP | 2002-100476 A | 4/2002 |
| JP | 2004-171808 A | 6/2004 |
| JP | 2007-019462 A | 1/2007 |

OTHER PUBLICATIONS

Wharton et al, "The Production and Characterisation of Novel Conducting Redox-Active Oligomeric Thin Films from Electrooxidised Indolo[3,2,1-jk]carbazole," Chem. Eur. J., 2009, 15, pp. 5482-5490.*
Helen G. Dunlop et al., "Attempts to prepare Optically Active Tervalent Nitrogen Compounds. Part I. Synthesis of 1:9-Phenylenecarbazole and Derivatives." Journal of Chemical Society 1939, 399: pp. 1945-1956.

* cited by examiner

*Primary Examiner* — Anthony Ho
(74) *Attorney, Agent, or Firm* — Sughrue Mion, PLLC

(57) ABSTRACT

An organic electroluminescence device includes: a pair of electrodes; and at least one organic layer including a light emitting layer, the light emitting layer being provided between the pair of electrodes, wherein at least one layer of the at least one organic layer contains a compound represented by formula (1):

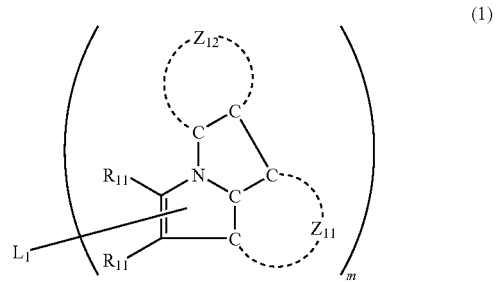

wherein each of $Z_{11}$ and $Z_{12}$ independently represents an aromatic heterocyclic ring or an aromatic hydrocarbon ring; $R_{11}$ represents a hydrogen atom or a substituent, provided that a plurality of $R_{11}$s are the same or different; m represents an integer of 1 or more; and $L_1$ represents a single bond or an m-valent linking group and is linked to any one of C atoms in $R_{11}$, $Z_{11}$ and $Z_{12}$, provided that when m is 1, $L_1$ does not exist.

27 Claims, No Drawings

ORGANIC ELECTROLUMINESCENCE DEVICE

BACKGROUND OF THE INVENTION

1. Field of the Invention

The present invention relates to a luminescence device capable of converting electric energy into light to achieve light emission, in particular to an organic electroluminescence device (luminescence device or EL device).

2. Description of the Related Art

An organic electroluminescence (EL) device is being watched as a promising display device because light emission with high brightness is obtained at a low voltage. A consumed electric power is an important characteristic value of this organic electroluminescence device. The consumed electric power is expressed by a product of voltage and current. When not only a voltage value necessary for obtaining desired brightness is lower, but a current value is smaller, the consumed electric powder of the device can be made lower.

In recent years, high efficiency of the device is being advanced by using a phosphorescent material. Iridium complexes, platinum complexes and so on are known as the phosphorescent material (see, for example, JP-A-2001-247859 and JP-A-2007-19462). However, a device in which high efficiency and high durability are compatible with each other has not been developed yet.

Also, there have been reported organic EL devices using, as a material, a compound having a nitrogen-containing heterocyclic ring intending to provide a device with high efficiency and low voltage (see, for example, JP-A-2002-100476 and JP-A-2004-171808). However, higher efficiency and driving at a lower voltage are being demanded.

On the other hand, though *Journal of Chemical Society*, 1939, pages 1945 to 1956 describes a compound obtained by condensing a nitrogen-containing heterocyclic ring with an aromatic heterocyclic ring or an aromatic hydrocarbon ring, it does not describe any applications thereof.

SUMMARY OF THE INVENTION

An object of the invention is to provide an electroluminescence device having high luminous efficiency and capable of being driven at a low voltage. Another object of the invention is to provide a highly condensed nitrogen-containing heterocyclic compound which is suitably used therefor.

The foregoing problems have been attained by the following measures.

[1] An organic electroluminescence device, comprising:
a pair of electrodes; and
at least one organic layer including a light emitting layer, the light emitting layer being provided between the pair of electrodes,
wherein at least one layer of the at least one organic layer contains a compound represented by formula (1):

(1)

wherein each of $Z_{11}$ and $Z_{12}$ independently represents an aromatic heterocyclic ring or an aromatic hydrocarbon ring;

$R_{11}$ represents a hydrogen atom or a substituent, provided that a plurality of $R_{11}$s are the same or different;

m represents an integer of 1 or more; and $L_1$ represents a single bond or an m-valent linking group and is linked to any one of C atoms in $R_{11}$, $Z_{11}$ and $Z_{12}$, provided that when m is 1, $L_1$ does not exist.

[2] The organic electroluminescence device as described in [1] above,
wherein the compound represented by formula (1) is a compound represented by formula (2):

(2)

wherein $Z_{22}$ represents an aromatic heterocyclic ring or an aromatic hydrocarbon ring;

$R_{21}$ represents a hydrogen atom or a substituent, provided that a plurality of $R_{21}$s are the same or different;

each of $A_{21}$ to $A_{23}$ independently represents a nitrogen atom or C—$R_{22}$;

$R_{22}$ represents a hydrogen atom or a substituent, provided that a plurality of $R_{22}$s are the same or different;

m represents an integer of 1 or more; and $L_2$ represents a single bond or an m-valent linking group and is linked to any one of C atoms in $R_{21}$, $Z_{22}$ and $A_{21}$ to $A_{23}$, provided that when m is 1, $L_2$ does not exist.

[3] The organic electroluminescence device as described in [1] above,
wherein the compound represented by formula (1) is a compound represented by formula (3):

(3)

wherein $Z_{31}$ represents an aromatic heterocyclic ring or an aromatic hydrocarbon ring;

$R_{31}$ represents a hydrogen atom or a substituent, provided that a plurality of $R_{31}$s are the same or different;

each of $A_{31}$ to $A_{34}$ independently represents a nitrogen atom or C—$R_{32}$;

$R_{32}$ represents a hydrogen atom or a substituent, provided that a plurality of $R_{32}$s are the same or different;

m represents an integer of 1 or more; and $L_3$ represents a single bond or an m-valent linking group and is linked to any one of C atoms in $R_{31}$, $Z_{31}$ and $A_{31}$ to $A_{34}$, provided that when m is 1, $L_3$ does not exist.

[4] The organic electroluminescence device as described in [2] or [3] above,
wherein the compound represented by formula (2) or (3) is a compound represented by formula (4):

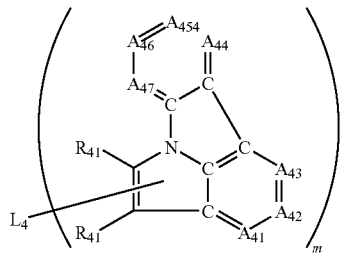

(4)

wherein $R_{41}$ represents a hydrogen atom or a substituent, provided that a plurality of $R_{41}$s are the same or different;
each of $A_{41}$ to $A_{47}$ independently represents a nitrogen atom or C—$R_{42}$;
$R_{42}$ represents a hydrogen atom or a substituent, provided that a plurality of $R_{42}$s are the same or different;
m represents an integer of 1 or more; and
$L_4$ represents a single bond or an m-valent linking group and is linked to any one of C atoms in $R_{41}$ and $A_{41}$ to $A_{47}$, provided that when m is 1, $L_4$ does not exist.

[5] The organic electroluminescence device as described in [1] above,
wherein the compound represented by formula (1) is a compound represented by formula (5):

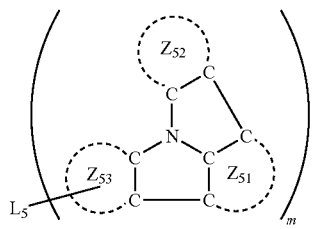

(5)

wherein each of $Z_{51}$ to $Z_{53}$ independently represents an aromatic heterocyclic ring or an aromatic hydrocarbon ring;
m represents an integer of 1 or more; and
$L_5$ represents a single bond or an m-valent linking group and is linked to any one of C atoms in $Z_{51}$ to $Z_{53}$, provided that when m is 1, $L_5$ does not exist.

[6] The organic electroluminescence device as described in [5] above,
wherein the compound represented by the formula (5) is a compound represented by formula (6):

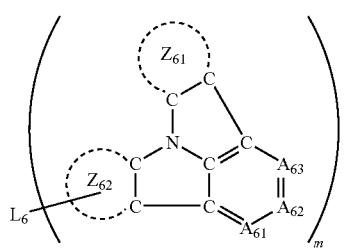

(6)

wherein each of $Z_{61}$ and $Z_{62}$ independently represents an aromatic heterocyclic ring or an aromatic hydrocarbon ring;
each of $A_{61}$ to $A_{63}$ independently represents a nitrogen atom or C—$R_{61}$;
$R_{61}$ represents a hydrogen atom or a substituent, provided that a plurality of $R_{61}$s are the same or different;
m represents an integer of 1 or more; and
$L_6$ represents a single bond or an m-valent linking group and is linked to any one of C atoms in $Z_{61}$, $Z_{62}$ and $A_{61}$ to $A_{63}$, provided that when m is 1, $L_6$ does not exist.

[7] The organic electroluminescence device as described in [5] above,
wherein the compound represented by formula (5) is a compound represented by formula (7):

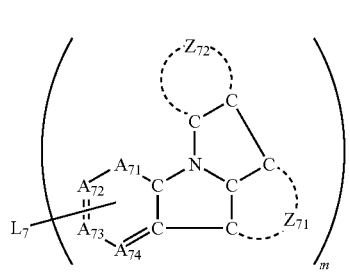

(7)

wherein each of $Z_{71}$ and $Z_{72}$ independently represents an aromatic heterocyclic ring or an aromatic hydrocarbon ring;
each of $A_{71}$ to $A_{74}$ independently represents a nitrogen atom or C—$R_{71}$;
$R_{71}$ represents a hydrogen atom or a substituent, provided that a plurality of $R_{71}$s are the same or different;
m represents an integer of 1 or more; and
$L_7$ represents a single bond or an m-valent linking group and is linked to any one of C atoms in $Z_{71}$, $Z_{72}$ and $A_{71}$ to $A_{74}$, provided that when m is 1, $L_7$ does not exist.

[8] The organic electroluminescence device as described in [6] above, wherein the compound represented by the formula (6) is a compound represented by formula (8):

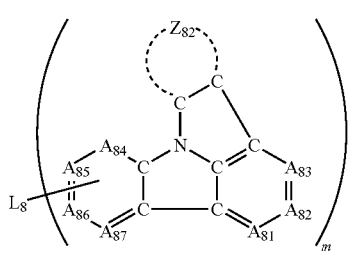

(8)

wherein $Z_{82}$ represents an aromatic heterocyclic ring or an aromatic hydrocarbon ring;
each of $A_{81}$ to $A_{87}$ independently represents a nitrogen atom or C—$R_{81}$;
$R_{81}$ represents a hydrogen atom or a substituent, provided that a plurality of $R_{81}$s are the same or different;
m represents an integer of 1 or more; and
$L_8$ represents a single bond or an m-valent linking group and is linked to any one of C atoms in $Z_{82}$ and $A_{81}$ to $A_{87}$, provided that when m is 1, $L_8$ does not exist.

[9] The organic electroluminescence device as described in [7] above,
wherein the compound represented by the formula (7) is a compound represented by formula (9):

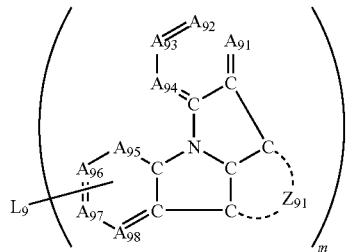

(9)

wherein $Z_{91}$ represents an aromatic heterocyclic ring or an aromatic hydrocarbon ring;
each of $A_{91}$ to $A_{98}$ independently represents a nitrogen atom or $C-R_{91}$;
$R_{91}$ represents a hydrogen atom or a substituent, provided that a plurality of $R_{91}$s are the same or different;
m represents an integer of 1 or more; and
$L_9$ represents a single bond or an m-valent linking group and is linked to any one of C atoms in $Z_{91}$ and $A_{91}$ to $A_{98}$, provided that when m is 1, $L_9$ does not exist.

[10] The organic electroluminescence device as described in [8] or [9] above,
wherein the compound represented by the formula (8) or (9) is a compound represented by formula (10):

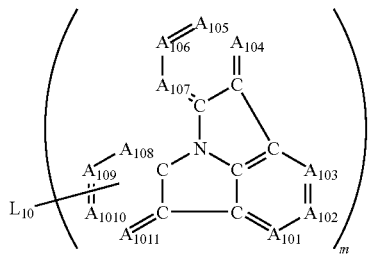

(10)

wherein each of $A_{101}$ to $A_{1011}$ independently represents a nitrogen atom or $C-R_{101}$;
$R_{101}$ represents a hydrogen atom or a substituent, provided that a plurality of $R_{101}$s are the same or different;
m represents an integer of 1 or more; and
$L_{10}$ represents a single bond or an m-valent linking group and is linked to any one of C atoms in $A_{101}$ to $A_{1011}$, provided that when m is 1, $L_{10}$ does not exist.

[11] A compound represented by formula (4-1):

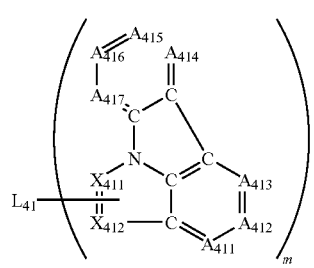

(4-1)

wherein each of $X_{411}$ and $X_{412}$ independently represents $C-R_{411}$;
$R_{411}$ represents a hydrogen atom or a substituent, provided that a plurality of $R_{411}$s are the same or different;
each of $A_{411}$ to $A_{417}$ independently represents a nitrogen atom or $C-R_{412}$;
$R_{412}$ represents a hydrogen atom or a substituent, provided that a plurality of $R_{412}$s are the same or different;
$L_{41}$ represents a single bond or an m-valent linking group and is linked to any one of C atoms in $X_{411}$, $X_{412}$ and $A_{411}$ to $A_{417}$;
when the linking group as $L_{41}$ is an aromatic hydrocarbon ring group or an aromatic heterocyclic group, a size of the ring is from a 5-membered to 6-membered ring; and
m represents an integer of 2 or more.

[12] The compound as described in [11] above, which is a compound represented by formula (4-2):

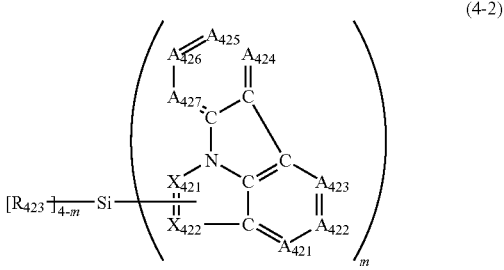

(4-2)

wherein each of $X_{421}$ and $X_{422}$ independently represents $C-R_{421}$;
$R_{421}$ represents a hydrogen atom or a substituent, provided that a plurality of $R_{421}$s are the same or different;
each of $A_{421}$ to $A_{427}$ independently represents a nitrogen atom or $C-R_{422}$;
$R_{422}$ represents a hydrogen atom or a substituent, provided that a plurality of $R_{422}$s are the same or different;
$R_{423}$ represents a hydrogen atom or a substituent, provided that a plurality of $R_{423}$s are the same or different;
m represents an integer of from 2 to 4; and
the silicon linking group is linked to any one of C atoms in $X_{421}$, $X_{422}$ and $A_{421}$ to $A_{427}$.

[13] The compound as described in [11] above, which is a compound represented by formula (4-3):

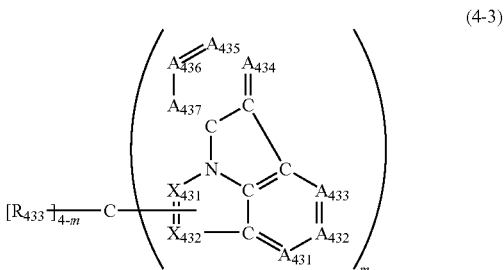

(4-3)

wherein each of $X_{431}$ and $X_{432}$ independently represents C—$R_{431}$;

$R_{431}$ represents a hydrogen atom or a substituent, provided that a plurality of $R_{431}$s are the same or different;

each of $A_{431}$ to $A_{437}$ independently represents a nitrogen atom or C—$R_{432}$;

$R_{432}$ represents a hydrogen atom or a substituent, provided that a plurality of $R_{432}$s are the same or different;

$R_{433}$ represents a hydrogen atom or a substituent, provided that a plurality of $R_{433}$s are the same or different;

m represents an integer of from 2 to 4; and the carbon linking group is linked to any one of C atoms in $X_{431}$, $X_{432}$ and $A_{431}$ to $A_{437}$.

[14] The compound as described in [11] above, which is a compound represented by formula (4-4):

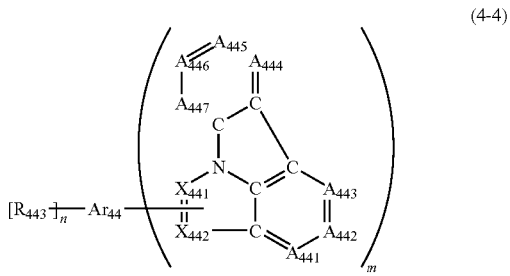

(4-4)

wherein each of $X_{441}$ and $X_{442}$ independently represents C—$R_{441}$;

$R_{441}$ represents a hydrogen atom or a substituent, provided that a plurality of $R_{441}$s are the same or different;

each of $A_{441}$ to $A_{447}$ independently represents a nitrogen atom or C—$R_{442}$;

$R_{442}$ represents a hydrogen atom or a substituent, provided that a plurality of $R_{442}$s are the same or different;

$Ar_{44}$ represents an aromatic hydrocarbon ring or an aromatic heterocyclic ring, and a size of the ring is from 5-membered to 6-membered ring;

$Ar_{44}$ is linked to any one of C atoms in $X_{441}$, $X_{442}$ and $A_{441}$ to $A_{447}$;

$R_{443}$ represents a hydrogen atom or a substituent, provided that a plurality of $R_{443}$s are the same or different;

m represents an integer of 2 or more; and n represents an integer of 0 or more.

[15] A compound represented by formula (4-5):

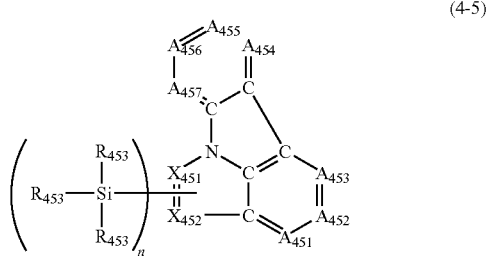

(4-5)

wherein each of $X_{451}$ and $X_{452}$ independently represents C—$R_{451}$;

$R_{451}$ represents a hydrogen atom or a substituent, provided that a plurality of C—$R_{451}$s are the same or different;

each of $A_{451}$ to $A_{457}$ independently represents a nitrogen atom or C—$R_{452}$;

$R_{452}$ represents a hydrogen atom or a substituent, provided that a plurality of $R_{452}$s are the same or different;

$R_{453}$ represents a hydrogen atom or a substituent, provided that a plurality of $R_{453}$s are the same or different;

n represents an integer of 1 or more; and the silicon substituent is linked to any one of C atoms in $X_{451}$, $X_{452}$ and $A_{451}$ to $A_{457}$.

[16] The compound as described in [11] above, which is a compound represented by formula (10-1):

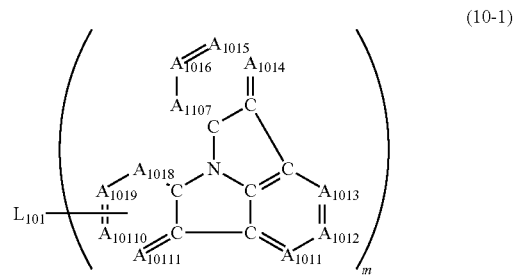

(10-1)

wherein each of $A_{1011}$ to $A_{10111}$ independently represents a nitrogen atom or C—$R_{1011}$;

$R_{1011}$ represents a hydrogen atom or a substituent, provided that a plurality of $R_{1011}$ are the same or different;

$L_{101}$ represents a single bond or an m-valent linking group and is linked to any one of C atoms in $A_{1011}$ to $A_{10111}$;

when the linking group as $L_{101}$ is an aromatic hydrocarbon ring group or an aromatic heterocyclic group, a size of the ring is from a 5-membered to 6-membered ring; and m represents an integer of 2 or more.

[17] The compound as described in [16] above, which is a compound represented by formula (10-2):

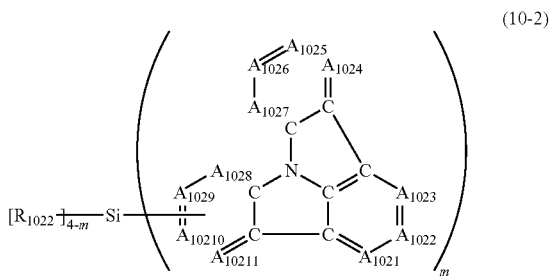

(10-2)

wherein each of $A_{1021}$ to $A_{10211}$ independently represents a nitrogen atom or C—$R_{1021}$;

$R_{1021}$ represents a hydrogen atom or a substituent, provided that a plurality of $R_{1021}$s are the same or different;

$R_{1022}$ represents a hydrogen atom or a substituent, provided that a plurality of $R_{1022}$s are the same or different;

m represents an integer of from 2 to 4; and the silicon linking group is linked to any one of C atoms in $A_{1021}$ to $A_{10211}$.

[18] The compound as described in [16] above, which is a compound represented by formula (10-3):

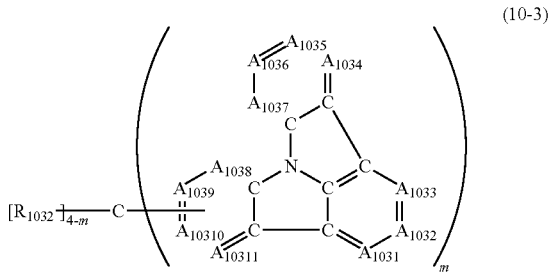

(10-3)

wherein each of $A_{1031}$ to $A_{10311}$ independently represents a nitrogen atom or C—$R_{1031}$;

$R_{1031}$ represents a hydrogen atom or a substituent, provided that a plurality of $R_{1031}$s are the same or different;

$R_{1032}$ represents a hydrogen atom or a substituent, provided that a plurality of $R_{1032}$s are the same or different;

m represents an integer of from 2 to 4; and the carbon linking group is linked to any one of C atoms in $A_{1031}$ to $A_{10311}$.

[19] The compound as described in [16] above, which is a compound represented by formula (10-4):

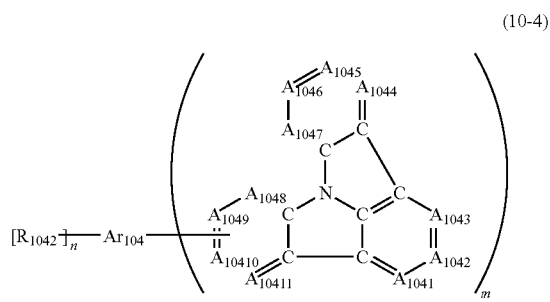

(10-4)

wherein each of $A_{1041}$ to $A_{10411}$ independently represents a nitrogen atom or C—$R_{1041}$;

$R_{1041}$ represents a hydrogen atom or a substituent, provided that a plurality of $R_{1041}$s are the same or different;

$Ar_{104}$ represents an aromatic hydrocarbon ring or an aromatic heterocyclic ring, and a size of the ring is from 5-membered to 6-membered ring;

$Ar_{104}$ is linked to any one of C atoms in $A_{1041}$ to $A_{10411}$;

$R_{1042}$ represents a hydrogen atom or a substituent, provided that a plurality of $R_{1042}$s are the same or different;

m represents an integer of 2 or more; and n represents an integer of 0 or more.

[20] A compound represented by formula (10-5):

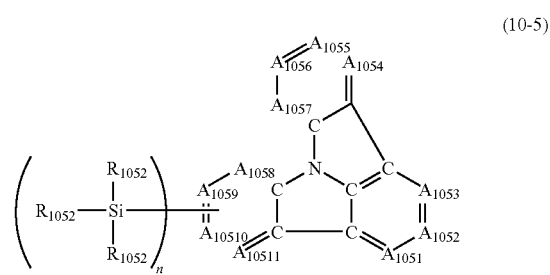

(10-5)

wherein each of $A_{1051}$ to $A_{10511}$ independently represents a nitrogen atom or C—$R_{1051}$;

$R_{1051}$ represents a hydrogen atom or a substituent, provided that a plurality of $R_{1051}$s are the same or different;

$R_{1052}$ represents a hydrogen atom or a substituent, provided that a plurality of $R_{1052}$s are the same or different;

n represents an integer of 1 or more; and the silicon linking group is linked to any one of C atoms in $A_{1051}$ to $A_{10511}$.

[21] An organic electroluminescence device, comprising:
a pair of electrodes; and
at least one organic layer including a light emitting layer, the light emitting layer being provided between the pair of electrodes,
wherein at least one layer of the at least one organic layer contains the compound represented by any one of formulae (4-1) to (4-5) and (10-1) to (10-5) as described in [11] to [20] above.

[22] The organic electroluminescence device as described in any one of [1] to [10] and [21] above,
wherein the light emitting layer contains a phosphorescent material.

[23] The organic electroluminescence device as described in [22] above,
wherein the phosphorescent material is an iridium complex or a platinum complex.

[24] The organic electroluminescence device as described in any one of [1] to [10] and [21] to [23] above,
wherein the light emitting layer contains the compound represented by any one of formulae (1) to (10), (4-1) to (4-5) and (10-1) to (10-5).

[25] The organic electroluminescence device as described in any one of [1] to [10] and [21] to [24] above,
wherein the pair of electrodes includes an anode,
a hole transport layer is provided between the light emitting layer and the anode, and
the hole transport layer contains the compound represented by any one of formulae (1) to (10), (4-1) to (4-5) and (10-1) to (10-5).

[26] The organic electroluminescence device as described in any one of [1] to [10] and [21] to [25] above,
wherein the pair of electrodes includes a cathode,
an electron transport layer is provided between the light emitting layer and the cathode, and
the electron transport layer contains the compound represented by any one of formulae (1) to (10), (4-1) to (4-5) and (10-1) to (10-5).

[27] The organic electroluminescence device as described in any one of [1] to [10] and [21] to [26] above,
wherein a glass transition temperature of the compound represented by any one of formulae (1) to (10), (4-1) to (4-5) and (10-1) to (10-5) is 130° C. or higher and not higher than 450° C.

[28] The organic electroluminescence device as described in any one of [1] to [10] and [21] to [27] above,
wherein a minimum excitation triplet energy level of the compound represented by any one of the formulae (1) to (10), (4-1) to (4-5) and (10-1) to (10-5) is 60 kcal/mole (251.4 kJ/mole) or more and not more than 95 kcal/mole (398.1 kJ/mole).

DETAILED DESCRIPTION OF THE INVENTION

The organic electroluminescence device of the invention is an organic electroluminescence device comprising a pair of electrodes having therebetween at least one organic layer including a light emitting layer, wherein a compound represented by the following formula (1) is contained in at least one of the organic layers.

The compound represented by the formula (1) includes a partial structure described below, and according to this structure, it becomes possible to attain high efficiency and low-voltage driving of the organic electroluminescence device.

The compound represented by the formula (1) is a condensed heterocyclic compound in which at least four rings are condensed with each other. Since the thus highly condensed compound represented by the formula (1) is expanded with respect to conjugation as compared with existing nitrogen-containing heterocyclic compounds, it is able to enhance electron injection properties while keeping hole injection properties and to enhance a balance of the charge transfer in the organic electroluminescence device. In particular, in the case where the light emitting layer is in a hole-excess state, by using the compound of the invention, the injection of an electron into the light emitting layer becomes easy, the charge balance within the light emitting layer is improved, and high efficiency and low-voltage driving of the organic electroluminescence device may be realized.

[Compound Represented by the Formula (1)]

The compound represented by the formula (1) is described in detail.

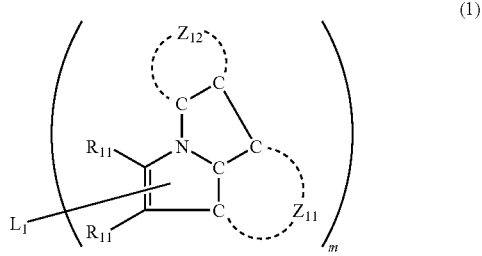

In the formula (1), each of $Z_{11}$ and $Z_{12}$ independently represents an aromatic heterocyclic ring or an aromatic hydrocarbon ring; $R_{11}$ represents a hydrogen atom or a substituent; each $R_{11}$ may be the same as or different from every other $R_{11}$; m represents an integer of 1 or more; and $L_1$ represents a single bond or an m-valent linking group and is linked to any one of C atoms in $R_{11}$, $Z_{11}$ and $Z_{12}$, provided that when m is 1, then $L_1$ does not exist.

As the substituent represented by $R_{11}$, those which are exemplified below as the following group A of substituent are applicable.

(Group A of Substituent)

Examples of the group A of substituent include an alkyl group (preferably an alkyl group having from 1 to 30 carbon atoms, more preferably an alkyl group having from 1 to 20 carbon atoms, and especially preferably an alkyl group having from 1 to 10 carbon atoms; for example, a methyl group, an ethyl group, an isopropyl group, a tert-butyl group, an n-octyl group, an n-decyl group, an n-hexadecyl group, a cyclopropyl group, a cyclopentyl group, a cyclohexyl group, etc.), an alicyclic hydrocarbon group (preferably an alicyclic hydrocarbon group having from 1 to 30 carbon atoms, more preferably an alicyclic hydrocarbon group having from 1 to 20 carbon atoms, and especially preferably an alicyclic hydrocarbon group having from 1 to 10 carbon atoms; for example, an adamantyl group, a cyclopropyl group, a cyclopentyl group, a cyclohexyl group, etc.), an alkenyl group (preferably an alkenyl group having from 2 to 30 carbon atoms, more preferably an alkenyl group having from 2 to 20 carbon atoms, and especially preferably an alkenyl group having from 2 to 10 carbon atoms; for example, a vinyl group, an allyl group, a 2-butenyl group, a 3-pentenyl group, etc.), an alkynyl group (preferably an alkynyl group having from 2 to 30 carbon atoms, more preferably an alkynyl group having from 2 to 20 carbon atoms, and especially preferably an alkynyl group having from 2 to 10 carbon atoms; for example, a propargyl group, a 3-pentynyl group, etc.), an aryl group (preferably an aryl group having from 6 to 30 carbon atoms, more preferably an aryl group having from 6 to 20 carbon atoms, and especially preferably from 6 to 12 carbon atoms; for example, a phenyl group, a p-methylphenyl group, a naphthyl group, an anthranyl group, etc.), an amino group (preferably an amino group having from 0 to 30 carbon atoms, more preferably an amino group having from 0 to 20 carbon atoms, and especially preferably an amino group having from 0 to 10 carbon atoms; for example, an amino group, a methylamino group, a dimethylamino group, a diethylamino group, a dibenzylamino group, a diphenylamino group, a ditolylamino group, etc.); an alkoxy group (preferably an alkoxy group having from 1 to 30 carbon atoms, more preferably an alkoxy group having from 1 to 20 carbon atoms, and especially preferably an alkoxy group having from 1 to 10 carbon atoms; for example, a methoxy group, an ethoxy group, a butoxy group, a 2-ethylhexyloxy group, etc.), an aryloxy group (preferably an aryloxy group having from 6 to 30 carbon atoms, an aryloxy group having from 6 to 20 carbon atoms, and especially preferably an aryloxy group having from 6 to 12 carbon atoms; for example, a phenyloxy group, a 1-naphthyloxy group, a 2-naphthyloxy group, etc.), a heterocyclic oxy group (preferably a heterocyclic oxy group having from 1 to 30 carbon atoms, more preferably a heterocyclic oxy group having from 1 to 20 carbon atoms, and especially preferably a heterocyclic oxy group having from 1 to 12 carbon atoms; for example, a pyridyloxy group, a pyrazyloxy group, a pyrimidyloxy group, a quinolyloxy group, etc.), an acyl group (preferably an acyl group having from 1 to 30 carbon atoms, more preferably an acyl group having from 1 to 20 carbon atoms, and especially preferably an acyl group having from 1 to 12 carbon atoms; for example, an acetyl group, a benzoyl group, a formyl group, a pivaloyl group, etc.), an alkoxycarbonyl group (preferably an alkoxycarbonyl group having from 2 to 30 carbon atoms, more preferably an alkoxycarbonyl group having from 2 to 20 carbon atoms, and especially preferably an alkoxycarbonyl group having from 2 to 12 carbon atoms; for example, a methoxycarbonyl group, an ethoxycarbonyl group, etc.), an aryloxycarbonyl group (preferably an aryloxycarbonyl group having from 7 to 30 carbon atoms, more preferably an aryloxycarbonyl group having from 7 to 20 carbon atoms, and especially preferably an aryloxycarbonyl group having from 7 to 12 carbon atoms; for example, a phenyloxycarbonyl group, etc.), an acyloxy group (preferably an acyloxy group having from 2 to 30 carbon atoms, more preferably an acyloxy group having from 2 to 20 carbon atoms, and especially preferably an acyloxy group having from 2 to 10 carbon atoms; for example, an acetoxy group, a benzoyloxy group, etc.), an acylamino group (preferably an acylamino group having from 2 to 30 carbon atoms, more preferably an acylamino group having from 2 to 20 carbon atoms, and especially preferably an acylamino group having from 2 to 10 carbon atoms; for example, an acetylamino group, a benzoylamino group, etc.), an alkoxycarbonylamino group (preferably an alkoxycarbonylamino group having from 2 to 30 carbon atoms, more preferably an alkoxycarbonylamino group having from 2 to 20 carbon atoms, and especially preferably an alkoxycarbonylamino group having from 2 to 12 carbon atoms; for example, a methoxycarbonylamino group, etc.), an aryloxycarbonylamino group (preferably an aryloxycarbonylamino group having from 7 to 30 carbon atoms, more preferably an aryloxycarbonylamino group having from 7 to 20 carbon atoms, and especially preferably an aryloxycarbonylamino group having from 7 to 12 carbon atoms; for example, a phenyloxycarbonylamino group, etc.), a sulfonylamino group (preferably a sulfonylamino group having from 1 to 30 carbon atoms, more preferably a sulfonylamino group having from 1 to 20 carbon atoms, and especially preferably a sulfonylamino group having from 1 to 12 carbon atoms; for example, a methanesulfonylamino group, a benzenesulfonylamino group, etc.), a sulfamoyl group (preferably a sulfamoyl group having from 0 to 30 carbon atoms, more preferably a sulfamoyl group having from 0 to 20 carbon atoms, and especially preferably a sulfamoyl group having from 0 to 12 carbon atoms; for example, a sulfamoyl group, a methylsulfamoyl group, a dimethylsulfamoyl group, a phenylsulfamoyl group, etc.), a carbamoyl group (preferably a carbamoyl group having from 1 to 30 carbon atoms, more preferably a carbamoyl group having from 1 to 20 carbon atoms, and especially preferably a carbamoyl group having from 1 to 12 carbon atoms; for example, a carbamoyl group, a methylcarbamoyl group, a diethylcarbamoyl group, a phenylcarbamoyl group, etc.), an alkylthio group (preferably an alkylthio group having from 1 to 30 carbon atoms, more preferably an alkylthio group having from 1 to 20 carbon atoms, and especially preferably an alkylthio group having from 1 to 12 carbon atoms; for example, a methylthio group, an ethylthio group, etc.), an arylthio group (preferably an arylthio group having from 6 to 30 carbon atoms, more preferably an arylthio group having from 6 to 20 carbon atoms, and especially preferably an arylthio group having from 6 to 12 carbon atoms; for example, a phenylthio group, etc.), a heterocyclic thio group (preferably a heterocyclic thio group having from 1 to 30 carbon atoms, more preferably a heterocyclic thio group having from 1 to 20 carbon atoms, and especially preferably a heterocyclic thio group having from 1 to 12 carbon atoms; for example, a pyridylthio group, a 2-benzimizolylthio group, a 2-benzoxazolylthio group, a 2-benzthiazolylthio group, etc.), a sulfonyl group (preferably a sulfonyl group having from 1 to 30 carbon atoms, more preferably a sulfonyl group having from 1 to 20 carbon atoms, and especially preferably a sulfonyl group having from 1 to 12 carbon atoms; for example, a mesyl group, a tosyl group, etc.), a sulfinyl group (preferably a sulfinyl group having from 1 to 30 carbon atoms, more preferably a sulfinyl group having from 1 to 20 carbon atoms, and especially preferably a sulfinyl group having from 1 to 12 carbon atoms; for example, a methanesulfinyl group, a benzenesulfinyl group, etc.), a ureido group (preferably a ureido group having from 1 to 30 carbon atoms, more preferably a ureido group having from 1 to 20 carbon atoms, and especially preferably a ureido group having from 1 to 12 carbon atoms; for example, a ureido group, a methylureido group, a phenylureido group, etc.), a phosphoric acid amide group (preferably a phosphoric acid amide group having from 1 to 30 carbon atoms, more preferably a phosphoric acid amide group having from 1 to 20 carbon atoms, and especially preferably a phosphoric acid amide group having from 1 to 12 carbon atoms; for example, a diethylphosphoric acid amide group, a phenylphosphoric acid amide group, etc.), a hydroxyl group, a mercapto group, a halogen atom (for example, a fluorine atom, a chlorine atom, a bromine atom, an iodine atom, etc.), a cyano group, a sulfo group, a carboxyl group, a nitro group, a hydroxamic acid group, a sulfino group, a hydrazino group, an imino group, a heterocyclic group (preferably a heterocyclic group having from 1 to 30 carbon atoms, and more preferably a heterocyclic group having from 1 to 12 carbon atoms; examples of the hetero atom include a nitrogen atom, an oxygen atom and a sulfur atom; and specific examples of the heterocyclic group include an imidazolyl group, a pyridyl group, a quinolyl group, a furyl group, a thienyl group, a piperidyl group, a morpholino group, a benzoxazolyl group, a benzimidazolyl group, a benzthiazolyl group, a carbazolyl group, an azepinyl group, etc.), a silyl group (preferably a silyl group having from 3 to 40 carbon atoms, more preferably a silyl group having from 3 to 30 carbon atoms, and especially preferably a silyl group having from 3 to 24 carbon atoms; for example, a trimethylsilyl group, a triphenylsilyl group, etc.), a silyloxy group (preferably a silyloxy group having from 3 to 40 carbon atoms, more preferably a silyloxy group having from 3 to 30 carbon atoms, and especially preferably a silyloxy group having from 3 to 24 carbon atoms; for example, a trimethylsilyloxy group, a triphenylsilyloxy group, etc.) and a phosphoryl group (for example, a diphenylphosphoryl group, a dimethylphosphoryl group, etc.). Each of these substituents may be further substituted. As the further substituent, the groups selected among those in the foregoing group A of substituent may be exemplified.

Also, a plurality of these substituents may be bound to each other to form a ring.

$R_{11}$s may be linked to each other to form a condensed ring. Examples of the ring which is formed include a benzene ring, a pyridine ring, a pyrazine ring, a pyrimidine ring, a triazine ring, a pyridazine ring, a pyrrole ring, a pyrazole ring, an imidazole ring, a triazole ring, an oxazole ring, an oxadiazole ring, a thiazole ring, a thiadiazole ring, a furan ring, a thiophene ring, a selenophene ring, a silole ring, a germole ring and a phosphole ring. Of these, a benzene ring, a pyridine ring, a furan ring, a thiophene ring, an imidazole ring, a thiazole ring, an oxazole ring, a benzothiazole ring, a benzothiophene ring and a benzofuran ring are preferable; and a benzene ring, a pyridine ring, a furan ring, an oxazole ring and a benzofuran ring are more preferable. Each of these rings may be further substituted. As the further substituent, the groups selected among those in the foregoing group A of substituent may be exemplified.

$R_{11}$ is preferably a hydrogen atom, an alkyl group, an alicyclic hydrocarbon group, an aryl group, a fluorine group, an amino group, an alkoxy group, an aryloxy group, a heterocyclic oxy group, an alkylthio group, an arylthio group, a heterocyclic thio group, a cyano group, a heterocyclic group, a silyl group, a silyloxy group or a group capable of forming a condensed ring upon linking of $R_{11}$s each other; more preferably a hydrogen atom, an alkyl group, an alicyclic hydrocarbon group, an aryl group, a fluorine group, a cyano group, a silyl group or a heterocyclic group; further more preferably a hydrogen atom, an alkyl group, an alicyclic hydrocarbon group, an aryl group, a fluorine group, a cyano group, a silyl group, a heterocyclic group or a group capable of forming a condensed ring upon linking of $R_{11}$s each other; still further more preferably an alkyl group, a silyl group, an alicyclic hydrocarbon group, an aryl group, a heterocyclic group or a group capable for forming a benzene ring or a pyridine ring upon linking of $R_{11}$s each other; especially preferably a methyl group, an ethyl group, an isopropyl group, a tert-butyl group, a trimethylsilyl group, a triphenylsilyl group, a phenyl group, a p-methylphenyl group, a naphthyl group, an anthranyl group or a group capable for forming a benzene ring or a pyridine ring upon linking of $R_{11}$s each other; and most preferably a tert-butyl group, a trimethylsilyl group, a triphenylsilyl group, a phenyl group or a group capable for forming a benzene ring or a pyridine ring upon linking of $R_{11}$s each other.

In the formula (1), examples of the aromatic heterocyclic ring and the aromatic hydrocarbon ring represented by each of $Z_{11}$ and $Z_{12}$ include a furan ring, a thiophene ring, a pyridine ring, a pyridazine group, a pyrimidine ring, a pyrazine ring, a triazine ring, a benzimidazole ring, an oxadiazole ring, a triazole ring, an imidazole ring, a pyrazole ring, a thiazole ring, an oxazole ring, an indole ring, a benzimidazole ring, a benzothiazole ring, a benzoxazole ring, a quinoxaline ring, a quinazoline ring, a phthalazine ring, a carbazole ring, a carboline ring, a ring obtained by further substituting a carbon atom of a hydrocarbon ring constituting a carboline ring with a nitrogen atom, a benzene ring, a biphenyl ring, a naphthalene ring, an azulene ring, an anthracene ring, a phenanthrene ring, a pyrene ring, a chrysene ring, a naphthacene ring, a triphenylene ring, an o-terphenyl ring, an m-terphenyl ring, a p-terphenyl ring, an acenaphthene ring, a coronene ring, a fluorene ring, a fluoranthrene ring, a naphthacene ring, a pentacene ring, a perylene ring, a pentaphene ring, a picene ring, a pyrene ring, a pyranthrene ring, an anthranthrene ring and a benzofuran ring.

Each of $Z_{11}$ and $Z_{12}$ is independently preferably a benzene ring, a pyridine ring, a furan ring, a thiophene ring, an imidazole ring, a thiazole ring, an oxazole ring, a benzothiazole ring, a benzothiophene ring or a benzofuran ring; and more preferably a benzene ring, a pyridine ring, a furan ring, an oxazole ring or a benzofuran ring.

Each of the aromatic heterocyclic ring and the aromatic hydrocarbon ring may have a substituent. As the substituent, those which are exemplified previously as the group A of substituent are applicable. As the substituent, a methyl group, an ethyl group, an isopropyl group, a tert-butyl group, a trimethylsilyl group, a triphenylsilyl group, a phenyl group, a p-methylphenyl group, a naphthyl group and an anthranyl group are especially preferable; and a tert-butyl group, a trimethylsilyl group, a triphenylsilyl group and a phenyl group are the most preferable.

$L_1$ represents a single bond or an m-valent linking group. As the m-valent linking group, linking groups constituted of at least one atom selected among a carbon atom, a nitrogen atom, an oxygen atom, a sulfur atom, a silicon atom, a germanium atom and a phosphorus atom are preferable.

m represents an integer of 2 or more, preferably from 2 to 6, more preferably from 2 to 4, further more preferably 2 or 3, and especially preferably 2.

$L_1$ is more preferably a single bond, a substituted or unsubstituted carbon atom, a substituted or unsubstituted nitrogen atom, a substituted silicon atom, a substituted germanium atom, an oxygen atom, a sulfur atom or a 5-membered to 6-membered aromatic hydrocarbon ring group or aromatic heterocyclic group; further more preferably a single bond, a substituted or unsubstituted carbon atom, a substituted or unsubstituted nitrogen atom, a substituted silicon atom, a substituted germanium atom or a 5-membered to 6-membered aromatic hydrocarbon ring group; even further more preferably a single bond, a substituted carbon atom, a substituted silicon atom, a substituted nitrogen atom or a substituted germanium atom; and especially preferably a single bond, a carbon atom substituted with an alkyl group or a phenyl group, a silicon atom, a germanium atom or a nitrogen atom.

If possible, such a linking group may further have a substituent. As the substituent which may be introduced, those which are exemplified previously as the group A of substituent are applicable.

When the linking group is an aromatic hydrocarbon ring group or an aromatic heterocyclic group, then a size of the ring is from a 5-membered to 6-membered ring. This is for the purpose of keeping a high $T_1$ level (minimum excitation triplet energy level). Specific examples of the linking group are given below, but it should not be construed that the invention is limited thereto.

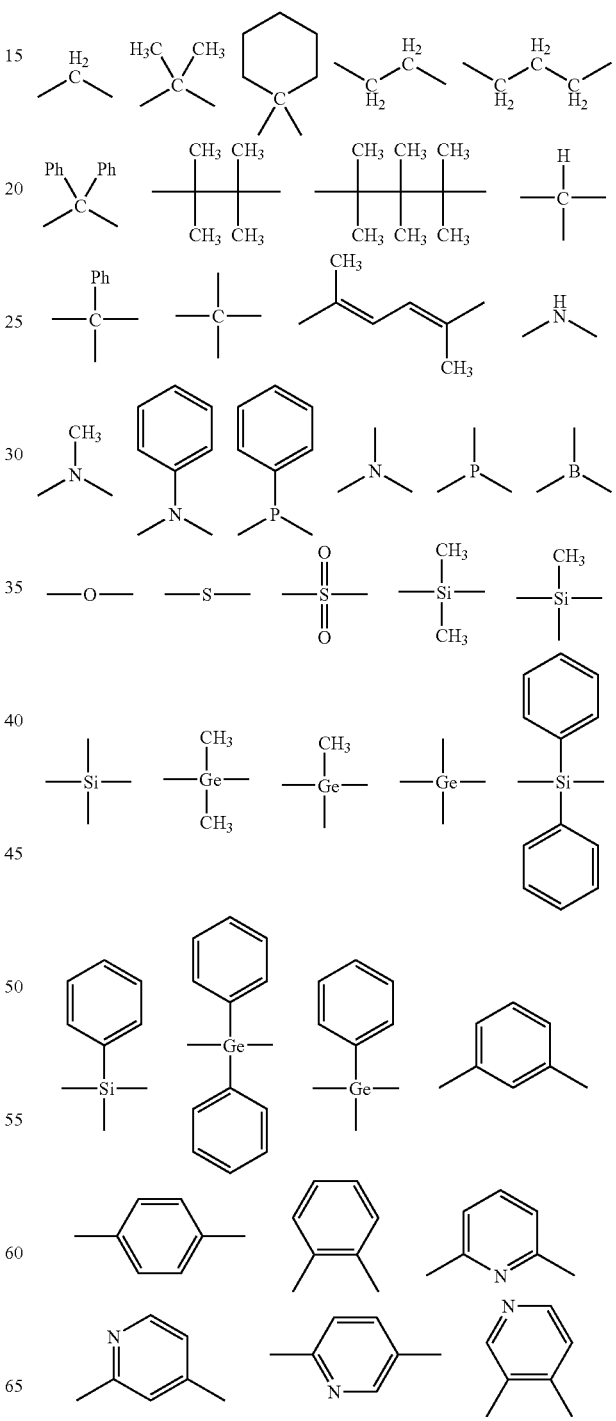

-continued

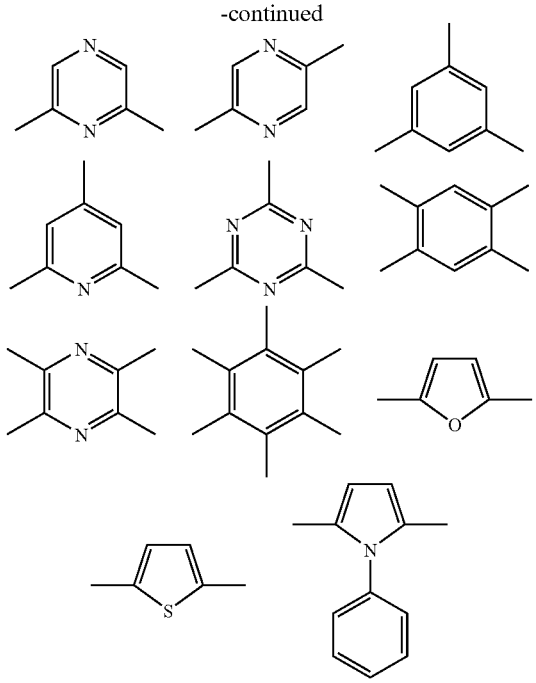

Of these, the following group (a-1) of linking group is preferable.

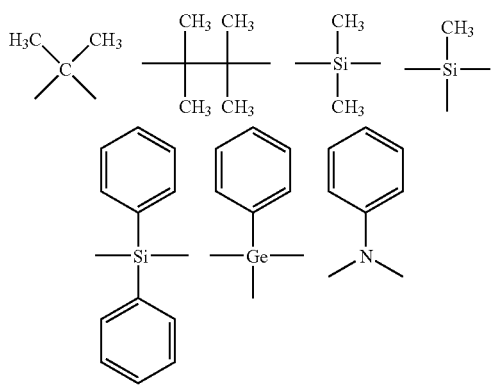

One of preferred embodiments as the compound represented by the formula (1) is concerned with a compound represented by the following formula (2).

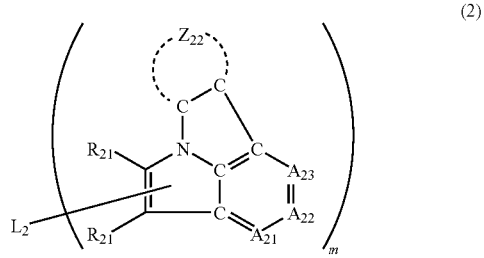

(2)

In the formula (2), $Z_{22}$ represents an aromatic heterocyclic ring or an aromatic hydrocarbon ring; $R_{21}$ represents a hydrogen atom or a substituent; each $R_{21}$ may be the same as or different from every other $R_{21}$; each of $A_{21}$ to $A_{23}$ independently represents a nitrogen atom or C—$R_{22}$; $R_{22}$ represents a hydrogen atom or a substituent; each $R_{22}$ may be the same as or different from every other $R_{22}$; m represents an integer of 1 or more; and $L_2$ represents a single bond or an m-valent linking group and is linked to any one of C atoms in $R_{21}$, $Z_{22}$ and $A_{21}$ to $A_{23}$, provided that when m is 1, then $L_2$ does not exist.

In the formula (2), though a combination of $A_{21}$ to $A_{23}$ is not particularly limited, a number of the nitrogen atom in $A_{21}$ to $A_{23}$ is preferably from 0 to 2, and more preferably from 0 to 1. m, $L_2$, $Z_{22}$ and $R_{21}$ are respectively synonymous with m, $L_1$, $Z_{12}$ and $R_{11}$ in the formula (1), and preferred ranges thereof are also the same.

As the substituent represented by $R_{22}$, those which are exemplified previously as the group A of substituent are applicable.

Each $R_{22}$ may be the same as or different from every other $R_{22}$. Also, $R_{22}$ may further have a substituent, and as the substituent, those which are exemplified previously as the group A of substituent are applicable. Also, $R_{22}$s may be linked to each other to form a condensed ring. Examples of the ring which is formed include a benzene ring, a pyridine ring, a pyrazine ring, a pyrimidine ring, a triazine ring, a pyridazine ring, a pyrrole ring, a pyrazole ring, an imidazole ring, a triazole ring, an oxazole ring, an oxadiazole ring, a thiazole ring, a thiadiazole ring, a furan ring, a thiophene ring, a selenophene ring, a silole ring, a germole ring and a phosphole ring.

$R_{22}$ is preferably a hydrogen atom, an alkyl group, an aromatic hydrocarbon ring group, a fluorine group, an amino group, an alkoxy group, an aryloxy group, a heterocyclic oxy group, an alkylthio group, an arylthio group, a heterocyclic thio group, a cyano group, a heterocyclic group, a silyl group or a silyloxy group; more preferably a hydrogen atom, an alkyl group, an aromatic hydrocarbon ring group, a fluorine group, a cyano group, a silyl group or a heterocyclic group; further more preferably an alkyl group, a silyl group, an aromatic hydrocarbon ring group or an aromatic heterocyclic group; especially preferably a methyl group, an ethyl group, an isopropyl group, a tert-butyl group, a trimethylsilyl group, a triphenylsilyl group, a phenyl group, a p-methylphenyl group, a naphthyl group or an anthranyl group; and most preferably a tert-butyl group, a trimethylsilyl group, a triphenylsilyl group or a phenyl group.

One of preferred embodiments as the compound represented by the formula (1) is concerned with a compound represented by the following formula (3).

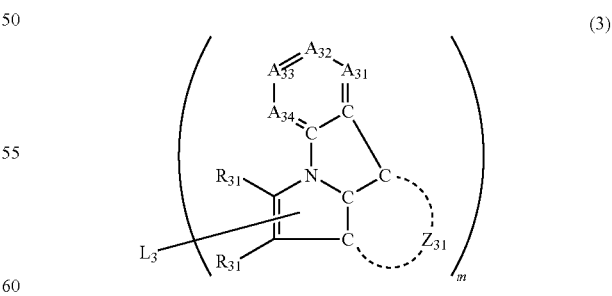

(3)

In the formula (3), $Z_{31}$ represents an aromatic heterocyclic ring or an aromatic hydrocarbon ring; $R_{31}$ represents a hydrogen atom or a substituent; each $R_{31}$ may be the same as or different from every other $R_{31}$; each of $A_{31}$ to $A_{34}$ independently represents a nitrogen atom or C—$R_{32}$; $R_{32}$ represents a hydrogen atom or a substituent; each $R_{32}$ may be the same as or different from every other $R_{32}$; m represents an integer of 1 or more; and $L_3$ represents a single bond or an m-valent linking group and is linked to any one of C atoms in $R_{31}$, $Z_{31}$ and $A_{31}$ to $A_{34}$, provided that when m is 1, then $L_3$ does not exist.

In the formula (3), though a combination of $A_{31}$ to $A_{34}$ is not particularly limited, a number of the nitrogen atom in $A_{31}$ to $A_{34}$ is preferably from 0 to 2, and more preferably from 0 to 1. m, $L_3$, $Z_{31}$ and $R_{31}$ are respectively synonymous with m, $L_1$, $Z_{11}$ and $R_{11}$ in the formula (1), and preferred ranges thereof are also the same.

$R_{32}$ is synonymous with $R_{22}$ in the formula (2), and a preferred range thereof is also the same.

One of preferred embodiments as the compounds represented by the formulae (2) and (3) is concerned with a compound represented by the following formula (4).

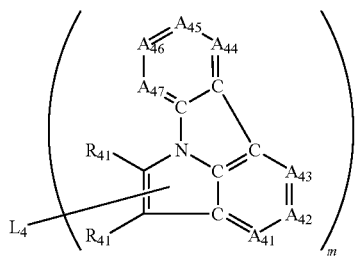

(4)

In the formula (4), $R_{41}$ represents a hydrogen atom or a substituent; each $R_{41}$ may be the same as or different from every other $R_{41}$; each of $A_{41}$ to $A_{47}$ independently represents a nitrogen atom or C—$R_{42}$; $R_{42}$ represents a hydrogen atom or a substituent; each $R_{42}$ may be the same as or different from every other $R_{42}$; m represents an integer of 1 or more; and $L_4$ represents a single bond or an m-valent linking group and is linked to any one of C atoms in $R_{41}$ and $A_{41}$ to $A_{47}$, provided that when m is 1, then $L_4$ does not exist.

In the formula (4), though a combination of $A_{41}$ to $A_{47}$ is not particularly limited, a number of the nitrogen atom in $A_{41}$ to $A_{47}$ is preferably from 0 to 4, and more preferably from 0 to 2.

m, $L_4$, $R_{41}$ and $R_{42}$ are respectively synonymous with m, $L_2$, $R_{21}$ and $R_{22}$ in the formula (2), and preferred ranges thereof are also the same.

One of preferred embodiments as the compound represented by the formula (1) is concerned with a compound represented by the following formula (5).

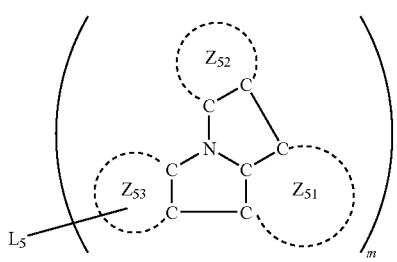

(5)

In the formula (5), each of $Z_{51}$ to $Z_{53}$ independently represents an aromatic heterocyclic ring or an aromatic hydrocarbon ring; m represents an integer of 1 or more; and $L_5$ represents a single bond or an m-valent linking group and is linked to any one of C atoms in $Z_{51}$ to $Z_{53}$, provided that when m is 1, then $L_5$ does not exist.

m, $L_5$ and $Z_{51}$ to $Z_{53}$ are respectively synonymous with m, $L_1$ and $Z_{11}$ to $Z_{12}$ in the formula (1), and preferred ranges thereof are also the same.

One of preferred embodiments as the compound represented by the formula (5) is concerned with a compound represented by the following formula (6).

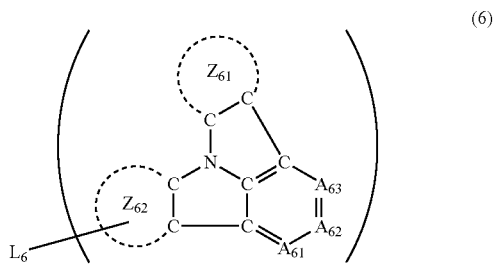

(6)

In the formula (6), each of $Z_{61}$ and $Z_{62}$ independently represents an aromatic heterocyclic ring or an aromatic hydrocarbon ring; each of $A_{61}$ to $A_{63}$ independently represents a nitrogen atom or C—$R_{61}$; $R_{61}$ represents a hydrogen atom or a substituent; each $R_{61}$ may be the same as or different from every other $R_{61}$; m represents an integer of 1 or more; and $L_6$ represents a single bond or an m-valent linking group and is linked to any one of C atoms in $Z_{61}$, $Z_{62}$ and $A_{61}$ to $A_{63}$, provided that when m is 1, then $L_6$ does not exist.

In the formula (6), though a combination of $A_{61}$ to $A_{63}$ is not particularly limited, a number of the nitrogen atom in $A_{61}$ to $A_{63}$ is preferably from 0 to 2, and more preferably from 0 to 1. m, $L_6$, $Z_{61}$ and $Z_{62}$ are respectively synonymous with m, $L_5$, $Z_{52}$ and $Z_{53}$ in the formula (5), and preferred ranges thereof are also the same.

$R_{61}$ is synonymous with $R_{22}$ in the formula (2), and a preferred range thereof is also the same.

One of preferred embodiments as the compound represented by the formula (5) is concerned with a compound represented by the following formula (7).

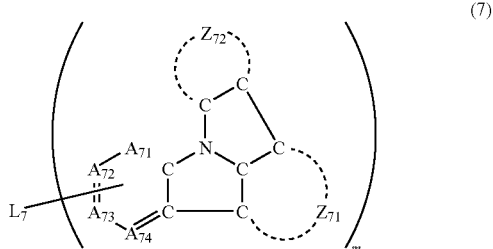

(7)

In the formula (7), each of $Z_{71}$ and $Z_{72}$ independently represents an aromatic heterocyclic ring or an aromatic hydrocarbon ring; each of $A_{71}$ to $A_{74}$ independently represents a nitrogen atom or C—$R_{71}$; $R_{71}$ represents a hydrogen atom or a substituent; each $R_{71}$ may be the same as or different from every other $R_{71}$; m represents an integer of 1 or more; and $L_7$ represents a single bond or an m-valent linking group and is linked to any one of C atoms in $Z_{71}$, $Z_{72}$ and $A_{71}$ to $A_{74}$, provided that when m is 1, then $L_7$ does not exist.

In the formula (7), though a combination of $A_{71}$ to $A_{74}$ is not particularly limited, a number of the nitrogen atom in $A_{71}$ to $A_{74}$ is preferably from 0 to 2, and more preferably from 0 to 1. m, $L_7$, $Z_{71}$ and $Z_{72}$ are respectively synonymous with m, $L_5$, $Z_{51}$ and $Z_{52}$ in the formula (5), and preferred ranges thereof are also the same.

$R_{71}$ is synonymous with $R_{22}$ in the formula (2), and a preferred range thereof is also the same.

One of preferred embodiments as the compound represented by the formula (6) is concerned with a compound represented by the following formula (8).

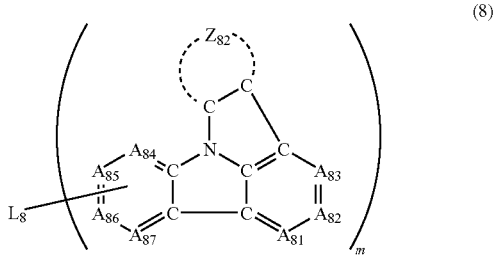

In the formula (8), $Z_{82}$ represents an aromatic heterocyclic ring or an aromatic hydrocarbon ring; each of $A_{81}$ to $A_{87}$ independently represents a nitrogen atom or C—$R_{81}$; $R_{81}$ represents a hydrogen atom or a substituent; each $R_{81}$ may be the same as or different from every other $R_{81}$; m represents an integer of 1 or more; and $L_8$ represents a single bond or an m-valent linking group and is linked to any one of C atoms in $Z_{82}$ and $A_{81}$ to $A_{87}$, provided that when m is 1, then $L_8$ does not exist.

In the formula (8), though a combination of $A_{81}$ to $A_{87}$ is not particularly limited, a number of the nitrogen atom in $A_{81}$ to $A_{87}$ is preferably from 0 to 4, and more preferably from 0 to 2. m, $L_8$, $Z_{82}$ and $R_{81}$ are respectively synonymous with m, $L_6$, $Z_{61}$ and $R_{61}$ in the formula (6), and preferred ranges thereof are also the same.

One of preferred embodiments as the compound represented by the formula (7) is concerned with a compound represented by the following formula (9).

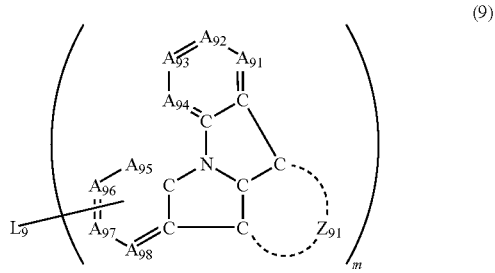

In the formula (9), $Z_{91}$ represents an aromatic heterocyclic ring or an aromatic hydrocarbon ring; each of $A_{91}$ to $A_{98}$ independently represents a nitrogen atom or C—$R_{91}$; $R_{91}$ represents a hydrogen atom or a substituent; each $R_{91}$ may be the same as or different from every other $R_{91}$; m represents an integer of 1 or more; and $L_9$ represents a single bond or an m-valent linking group and is linked to any one of C atoms in $Z_{91}$ and $A_{91}$ to $A_{98}$, provided that when m is 1, then $L_9$ does not exist.

In the formula (9), though a combination of $A_{91}$ to $A_{98}$ is not particularly limited, a number of the nitrogen atom in $A_{91}$ to $A_{98}$ is preferably from 0 to 4, and more preferably from 0 to 2. m, $L_9$, $Z_{91}$ and $R_{91}$ are respectively synonymous with m, $L_7$, $Z_{71}$ and $R_{71}$ in the formula (7), and preferred ranges thereof are also the same.

One of preferred embodiments as the compounds represented by the formulae (8) and (9) is concerned with a compound represented by the following formula (10).

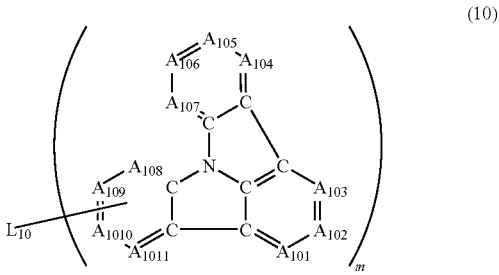

In the formula (10), each of $A_{101}$ to $A_{1011}$ independently represents a nitrogen atom or C—$R_{101}$; $R_{101}$ represents a hydrogen atom or a substituent; each $R_{101}$ may be the same as or different from every other $R_{101}$; m represents an integer of 1 or more; and $L_{10}$ represents a single bond or an m-valent linking group and is linked to any one of C atoms in $A_{101}$ to $A_{1011}$, provided that when m is 1, then $L_{10}$ does not exist.

In the formula (10), though a combination of $A_{101}$ to $A_{1011}$ is not particularly limited, a number of the nitrogen atom in $A_{101}$ to $A_{1011}$ is preferably from 0 to 6, and more preferably from 0 to 3. $L_{10}$, m and $R_{101}$ are respectively synonymous with $L_8$, m and $R_{81}$ in the formula (8), and preferred ranges thereof are also the same.

One of preferred embodiments as the compound represented by the formula (4) is concerned with a compound represented by the following formula (4-1).

The invention is also concerned with the compound represented by the formula (4-1). The compound represented by the formula (4-1) is a novel compound and may be preferably used as a material for organic electroluminescence devices.

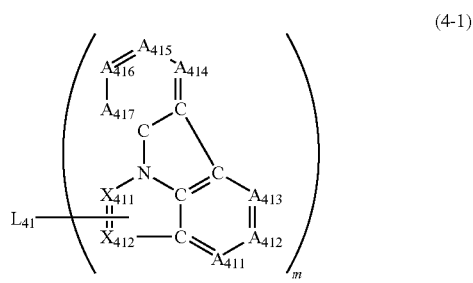

In the formula (4-1), each of $X_{411}$ and $X_{412}$ independently represents C—$R_{411}$; $R_{411}$ represents a hydrogen atom or a substituent; each $R_{411}$ may be the same as or different from every other $R_{411}$; each of $A_{411}$ to $A_{417}$ independently represents a nitrogen atom or C—$R_{412}$; $R_{412}$ represents a hydrogen atom or a substituent; each $R_{412}$ may be the same as or different from every other $R_{412}$; $L_{41}$ represents a single bond or an m-valent linking group and is linked to any one of C atoms in $X_{411}$, $X_{412}$ and $A_{411}$ to $A_{417}$; when the linking group is an aromatic hydrocarbon ring group or an aromatic heterocyclic group, then a size of the ring is from a 5-membered to 6-membered ring; and m represents an integer of 2 or more.

In the formula (4-1), $X_{411}$, $X_{412}$, $A_{411}$ to $A_{417}$, $L_{41}$, $R_{411}$ and $R_{412}$ are respectively synonymous with $X_{41}$, $X_{42}$, $A_{41}$ to $A_{47}$, $L_4$, $R_{41}$ and $R_{42}$ in the formula (4), and preferred ranges thereof are also the same.

One of preferred embodiments as the compound represented by the formula (4-1) is concerned with a compound represented by the following formula (4-2).

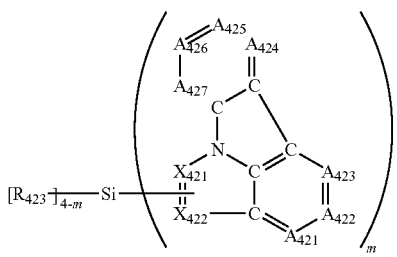

(4-2)

The formula (4-2) is described. Each of $X_{421}$ and $X_{422}$ independently represents C—$R_{421}$; $R_{421}$ represents a hydrogen atom or a substituent; each $R_{421}$ may be the same as or different from every other $R_{421}$; each of $A_{421}$ to $A_{427}$ independently represents a nitrogen atom or C—$R_{422}$; $R_{422}$ represents a hydrogen atom or a substituent; each $R_{422}$ may be the same as or different from every other $R_{422}$; $R_{423}$ represents a hydrogen atom or a substituent; each $R_{423}$ may be the same as or different from every other $R_{423}$; m represents an integer of from 2 to 4; and a silicon linking group is linked to any one of C atoms in $X_{421}$, $X_{422}$ and $A_{421}$ to $A_{427}$.

In the formula (4-2), $X_{421}$, $X_{422}$, $A_{421}$ to $A_{427}$, $R_{421}$ and $R_{422}$ are respectively synonymous with $X_{411}$, $X_{412}$, $A_{411}$ to $A_{417}$, $R_{411}$ and $R_{412}$ in the formula (4-1), and preferred ranges thereof are also the same.

$R_{423}$ is preferably a hydrogen atom, an alkyl group, an aromatic hydrocarbon ring group, an amino group, an alkoxy group, an aryloxy group, an aromatic heterocyclic oxy group, an alkylthio group, an arylthio group, a heterocyclic thio group, a cyano group, an aromatic heterocyclic group, a silyl group or a silyloxy group; more preferably an alkyl group, an aromatic hydrocarbon ring group, an amino group, a cyano group or an aromatic heterocyclic group; further more preferably an alkyl group, an aromatic hydrocarbon ring group, a cyano group or an aromatic heterocyclic group; especially preferably an alkyl group, an aromatic hydrocarbon ring group or an aromatic heterocyclic group; and most preferably an alkyl group or a phenyl group. Each $R_{423}$ may be the same as or different from every other $R_{423}$.

One of preferred embodiments as the compound represented by the formula (4-1) is concerned with a compound represented by the following formula (4-3).

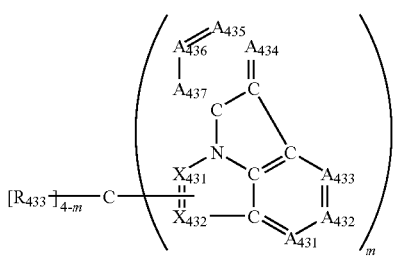

(4-3)

The formula (4-3) is described. Each of $X_{431}$ and $X_{432}$ independently represents C—$R_{431}$; $R_{431}$ represents a hydrogen atom or a substituent; each $R_{431}$ may be the same as or different from every other $R_{431}$; each of $A_{431}$ to $A_{437}$ independently represents a nitrogen atom or C—$R_{432}$; $R_{432}$ represents a hydrogen atom or a substituent; each $R_{432}$ may be the same as or different from every other $R_{432}$; $R_{433}$ represents a hydrogen atom or a substituent; each $R_{433}$ may be the same as or different from every other $R_{433}$; m represents an integer of from 2 to 4; and a carbon linking group is linked to any one of C atoms in $X_{431}$, $X_{432}$ and $A_{431}$ to $A_{437}$.

In the formula (4-3), $X_{431}$, $X_{432}$, $A_{431}$ to $A_{437}$, $R_{431}$ and $R_{432}$ are respectively synonymous with $X_{411}$, $X_{412}$, $A_{411}$ to $A_{417}$, $R_{411}$ and $R_{412}$ in the formula (4-1), and preferred ranges thereof are also the same.

$R_{433}$ is preferably a hydrogen atom, an alkyl group, an aromatic hydrocarbon ring group, an amino group, an alkoxy group, an aryloxy group, an aromatic heterocyclic oxy group, an alkylthio group, an arylthio group, a heterocyclic thio group, a cyano group, an aromatic heterocyclic group, a silyl group or a silyloxy group; more preferably an alkyl group, an aromatic hydrocarbon ring group, an amino group, a cyano group or an aromatic heterocyclic group; further more preferably an alkyl group, an aromatic hydrocarbon ring group, a cyano group or an aromatic heterocyclic group; especially preferably an alkyl group, an aromatic hydrocarbon ring group or an aromatic heterocyclic group; and most preferably an alkyl group or a phenyl group. Of these, a methyl group is preferable. Each $R_{433}$ may be the same as or different from every other $R_{433}$.

One of preferred embodiments as the compound represented by the formula (4-1) is concerned with a compound represented by the following formula (4-4).

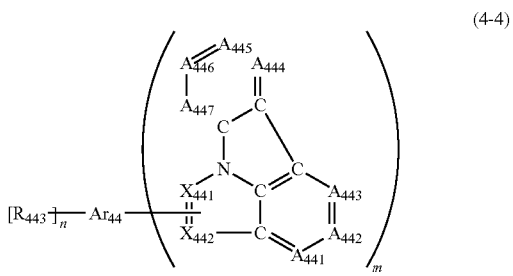

(4-4)

The formula (4-4) is described. Each of $X_{441}$ and $X_{442}$ independently represents C—$R_{441}$; $R_{441}$ represents a hydrogen atom or a substituent; each $R_{441}$ may be the same as or different from every other $R_{441}$; each of $A_{441}$ to $A_{447}$ independently represents a nitrogen atom or C—$R_{442}$; $R_{442}$ represents a hydrogen atom or a substituent; each $R_{442}$ may be the same as or different from every other $R_{442}$; $Ar_{44}$ represents an aromatic hydrocarbon ring or aromatic heterocyclic ring, and a size of the ring is from 5-membered to 6-membered ring; $Ar_{44}$ is linked to any one of C atoms in $X_{441}$, $X_{442}$ and $A_{441}$ to $A_{447}$; $R_{443}$ represents a hydrogen atom or a substituent; each $R_{443}$ may be the same as or different from every other $R_{443}$; m represents an integer of 2 or more; and n represents an integer of 0 or more.

In the formula (4-4), $X_{441}$, $X_{442}$, $A_{441}$ to $A_{447}$, $R_{441}$ and $R_{442}$ are respectively synonymous with $X_{411}$, $X_{412}$, $A_{411}$ to $A_{417}$, $R_{411}$ and $R_{412}$ in the formula (4-1), and preferred ranges thereof are also the same.

$R_{443}$ is preferably a hydrogen atom, an alkyl group, an aromatic hydrocarbon ring group, an amino group, an alkoxy group, an aryloxy group, an aromatic heterocyclic oxy group, an alkylthio group, an arylthio group, a heterocyclic thio group, a cyano group, an aromatic heterocyclic group, a silyl group or a silyloxy group; more preferably an alkyl group, an aromatic hydrocarbon ring group, an amino group, a cyano group or an aromatic heterocyclic group; further more preferably an alkyl group, an aromatic hydrocarbon ring group, a cyano group or an aromatic heterocyclic group; and especially preferably an alkyl group, an aromatic hydrocarbon ring group or an aromatic heterocyclic group. Each $R_{443}$ may be the same as or different from every other $R_{443}$.

$Ar_{44}$ represents a 5-membered to 6-membered aromatic hydrocarbon ring or aromatic heterocyclic ring. The 5-membered to 6-membered aromatic hydrocarbon ring or aromatic heterocyclic ring represented by $Ar_{44}$ is preferably a 6-membered ring.

Though the aromatic heterocyclic ring represented by $Ar_{44}$ is not particularly limited with respect to the hetero atom to be contained therein, it is preferably an aromatic heterocyclic ring containing nitrogen, oxygen, sulfur, selenium, silicon, germanium or phosphorus; more preferably an aromatic heterocyclic ring containing nitrogen, oxygen or sulfur; further more preferably an aromatic heterocyclic ring containing nitrogen or oxygen; and especially preferably an aromatic heterocyclic ring containing nitrogen. Though a number of the hetero atom which is contained in one aromatic heterocyclic ring represented by $Ar_{44}$ is not particularly limited, it is preferably from 1 to 3.

Specific examples of the 5-membered to 6-membered aromatic hydrocarbon ring or aromatic heterocyclic ring represented by $Ar_{44}$ include a benzene ring, a pyridine ring, a pyrazine ring, a pyrimidine ring, a triazine ring, a pyridazine ring, a pyrrole ring, a pyrazole ring, an imidazole ring, a triazole ring, an oxazole ring, an oxadiazole ring, a thiazole ring, a thiadiazole ring, a furan ring, a thiophene ring, a selenophene ring, a silole ring, a germole ring and a phosphole ring.

The aromatic hydrocarbon ring or aromatic heterocyclic ring formed from $Ar_{44}$ may have a substituent. As the substituent, those which are exemplified previously as the group A of substituent are applicable.

The 5-membered to 6-membered aromatic hydrocarbon ring or aromatic heterocyclic ring represented by $Ar_{44}$ is preferably a benzene ring, a pyridine ring, a pyrazine ring, a pyrimidine ring, a triazine ring, a pyrrole ring, a pyrazole ring, an imidazole ring, a triazole ring, an oxazole ring, a thiazole ring, a furan ring or a thiophene ring; more preferably a benzene ring, a pyridine ring, a pyrazine ring, a pyrrole ring, a pyrazole ring, an imidazole ring, an oxazole ring, a thiazole ring or a thiophene ring; further more preferably a benzene ring, a pyridine ring, a pyrazine ring, a pyrazole ring, an imidazole ring or a thiophene ring; and especially preferably a benzene ring, a pyridine ring or a pyrazine ring.

m represents an integer of 2 or more, preferably from 2 to 6, and more preferably from 2 to 4. n represents an integer of 0 or more, preferably from 0 to 4, and more preferably from 2 to 4.

One of preferred embodiments as the compound represented by the formula (4-1) is concerned with a compound represented by the following formula (4-5).

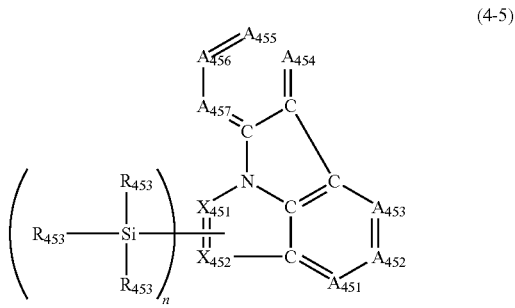

(4-5)

In the formula (4-5), each of $X_{451}$ and $X_{452}$ independently represents C—$R_{451}$; $R_{451}$ represents a hydrogen atom or a substituent; each $R_{451}$ may be the same as or different from every other $R_{451}$; each of $A_{451}$ to $A_{457}$ independently represents a nitrogen atom or C—$R_{452}$; $R_{452}$ represents a hydrogen atom or a substituent; each $R_{452}$ may be the same as or different from every other $R_{452}$; $R_{453}$ represents a hydrogen atom or a substituent; each $R_{453}$ may be the same as or different from every other $R_{453}$; n represents an integer of 1 or more; and a silicon substituent is linked to any one of C atoms in $X_{451}$, $X_{452}$ and $A_{451}$ to $A_{457}$.

In the formula (4-5), $X_{451}$, $X_{452}$, $A_{451}$ to $A_{457}$, $R_{451}$ and $R_{452}$ are respectively synonymous with $X_{411}$, $X_{412}$, $A_{411}$ to $A_{417}$, $R_{411}$ and $R_{412}$ in the formula (4-1), and preferred ranges thereof are also the same.

$R_{453}$ is preferably a hydrogen atom, an alkyl group, an aromatic hydrocarbon ring group, an amino group, an alkoxy group, an aryloxy group, an aromatic heterocyclic oxy group, an alkylthio group, an arylthio group, a heterocyclic thio group, a cyano group, an aromatic heterocyclic group, a silyl group or a silyloxy group; more preferably an alkyl group, an aromatic hydrocarbon ring group, an amino group, a cyano group or an aromatic heterocyclic group; further more preferably an alkyl group, an aromatic hydrocarbon ring group, a cyano group or an aromatic heterocyclic group; especially preferably an alkyl group, an aromatic hydrocarbon ring group or an aromatic heterocyclic group; especially preferably an alkyl group or a phenyl group; and most preferably a phenyl group.

n represents an integer of 0 or more, preferably from 0 to 4, and more preferably from 0 to 2.

One of preferred embodiments as the compound represented by the formula (4-1) is concerned with a compound represented by the following formula (10-1).

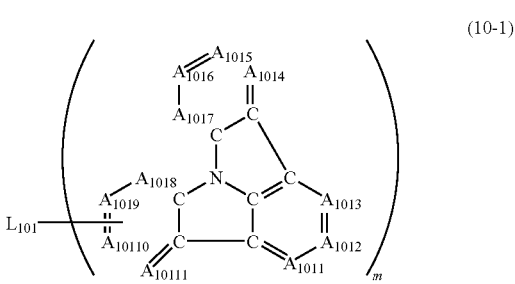

(10-1)

The formula (10-1) is described. Each of $A_{1011}$ to $A_{10111}$ independently represents a nitrogen atom or C—$R_{1011}$; $R_{1011}$ represents a hydrogen atom or a substituent; each $R_{1011}$ may be the same as or different from every other $R_{1011}$; $L_{101}$ represents a single bond or an m-valent linking group and is linked to any one of C atoms in $A_{1011}$ to $A_{10111}$; when the linking group is an aromatic hydrocarbon ring group or an aromatic heterocyclic group, then a size of the ring is from a 5-membered to 6-membered ring; and m represents an integer of 2 or more.

In the formula (10-1), $A_{1011}$ to $A_{10111}$, $L_{101}$ and $R_{1011}$ are respectively synonymous with $A_{101}$ to $A_{1011}$, $L_{10}$ and $R_{101}$ in the formula (10), and preferred ranges thereof are also the same.

m represents an integer of 2 or more, preferably from 2 to 6, more preferably from 2 to 4, further more preferably 2 or 3, and especially preferably 2.

One of preferred embodiments as the compound represented by the formula (10-1) is concerned with a compound represented by the following formula (10-2).

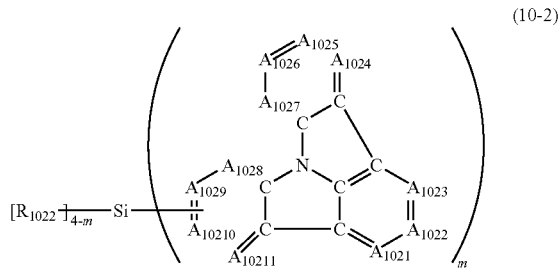

(10-2)

The formula (10-2) is described. Each of $A_{1021}$ to $A_{10211}$ independently represents a nitrogen atom or C—$R_{1021}$; $R_{1021}$ represents a hydrogen atom or a substituent; each $R_{1021}$ may be the same as or different from every other $R_{1021}$; $R_{1022}$ represents a hydrogen atom or a substituent; each $R_{1022}$ may be the same as or different from every other $R_{1022}$; m represents an integer of from 2 to 4; and a silicon linking group is linked to any one of C atoms in $A_{1021}$ to $A_{10211}$.

In the formula (10-2), $A_{1021}$ to $A_{10211}$ and $R_{1021}$ are respectively synonymous with $A_{1011}$ to $A_{10111}$ and $R_{1011}$ in the formula (10-1), and preferred ranges thereof are also the same.

$R_{1022}$ is synonymous with $R_{423}$ in the formula (4-2), and a preferred range thereof is also the same.

One of preferred embodiments as the compound represented by the formula (10-1) is concerned with a compound represented by the following formula (10-3).

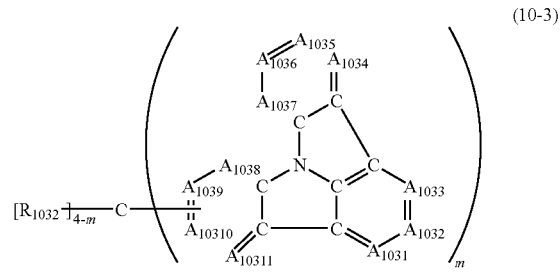

(10-3)

The formula (10-3) is described. Each of $A_{1031}$ to $A_{10311}$ independently represents a nitrogen atom or C—$R_{1031}$; $R_{1031}$ represents a hydrogen atom or a substituent; each $R_{1031}$ may be the same as or different from every other $R_{1031}$; $R_{1032}$ represents a hydrogen atom or a substituent; each $R_{1032}$ may be the same as or different from every other $R_{1032}$; m represents an integer of from 2 to 4; and a carbon linking group is linked to any one of C atoms in $A_{1031}$ to $A_{10311}$.

In the formula (10-3), $A_{1031}$ to $A_{10311}$ and $R_{1031}$ are respectively synonymous with $A_{1011}$ to $A_{10111}$ and $R_{1011}$ in the formula (10-1), and preferred ranges thereof are also the same.

$R_{1032}$ is synonymous with $R_{433}$ in the formula (4-3), and a preferred range thereof is also the same.

One of preferred embodiments as the compound represented by the formula (10-1) is concerned with a compound represented by the following formula (10-4).

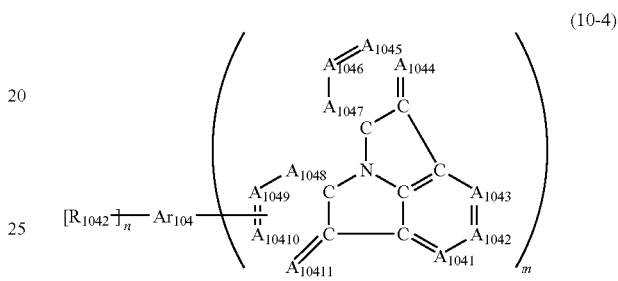

(10-4)

The formula (10-4) is described. Each of $A_{1041}$ to $A_{10411}$ independently represents a nitrogen atom or C—$R_{1041}$; $R_{1041}$ represents a hydrogen atom or a substituent; each $R_{1041}$ may be the same as or different from every other $R_{1041}$; $Ar_{104}$ represents an aromatic hydrocarbon ring or aromatic heterocyclic ring, and a size of the ring is from 5-membered to 6-membered ring; $Ar_{104}$ is linked to any one of C atoms in $A_{1041}$ to $A_{10411}$; $R_{1042}$ represents a hydrogen atom or a substituent; each $R_{1042}$ may be the same as or different from every other $R_{1042}$; m represents an integer of 2 or more; and n represents an integer of 0 or more.

In the formula (10-4), $A_{1041}$ to $A_{10411}$ and $R_{1041}$ are respectively synonymous with $A_{1011}$ to $A_{10111}$ and $R_{1011}$ in the formula (10-1), and preferred ranges thereof are also the same.

$R_{1042}$ is synonymous with $R_{443}$ in the formula (4-4), and a preferred range thereof is also the same.

$Ar_{104}$ represents a 5-membered to 6-membered aromatic hydrocarbon ring or aromatic heterocyclic ring. The 5-membered to 6-membered aromatic hydrocarbon ring or aromatic heterocyclic ring represented by $Ar_{104}$ is preferably a 6-membered ring.

Though the aromatic heterocyclic ring represented by $Ar_{104}$ is not particularly limited with respect to the hetero atom to be contained therein, it is preferably an aromatic heterocyclic ring containing nitrogen, oxygen, sulfur, selenium, silicon, germanium or phosphorus; more preferably an aromatic heterocyclic ring containing nitrogen, oxygen or sulfur; further more preferably an aromatic heterocyclic ring containing nitrogen or oxygen; and especially preferably an aromatic heterocyclic ring containing nitrogen. Though a number of the hetero atom which is contained in one aromatic heterocyclic ring represented by $Ar_{104}$ is not particularly limited, it is preferably from 1 to 3.

Specific examples of the 5-membered to 6-membered aromatic hydrocarbon ring or aromatic heterocyclic ring represented by $Ar_{104}$ include a benzene ring, a pyridine ring, a pyrazine ring, a pyrimidine ring, a triazine ring, a pyridazine ring, a pyrrole ring, a pyrazole ring, an imidazole ring, a triazole ring, an oxazole ring, an oxadiazole ring, a thiazole ring, a thiadiazole ring, a furan ring, a thiophene ring, a selenophene ring, a silole ring, a germole ring and a phosphole ring.

The aromatic hydrocarbon ring or aromatic heterocyclic ring formed from $Ar_{104}$ may have a substituent. As the substituent, those which are exemplified previously as the group A of substituent are applicable.

The 5-membered to 6-membered aromatic hydrocarbon ring or aromatic heterocyclic ring represented by $Ar_{104}$ is preferably a benzene ring, a pyridine ring, a pyrazine ring, a pyrimidine ring, a triazine ring, a pyrrole ring, a pyrazole ring, an imidazole ring, a triazole ring, an oxazole ring, a thiazole ring, a furan ring or a thiophene ring; more preferably a benzene ring, a pyridine ring, a pyrazine ring, a pyrrole ring, a pyrazole ring, an imidazole ring, an oxazole ring, a thiazole ring or a thiophene ring; further more preferably a benzene ring, a pyridine ring, a pyrazine ring, a pyrazole ring, an imidazole ring or a thiophene ring; and especially preferably a benzene ring, a pyridine ring or a pyrazine ring.

m represents an integer of 2 or more, preferably from 2 to 6, and more preferably from 2 to 4. n represents an integer of 0 or more, preferably from 0 to 4, and more preferably from 2 to 4.

One of preferred embodiments as the compound represented by the formula (10-1) is concerned with a compound represented by the following formula (10-5).

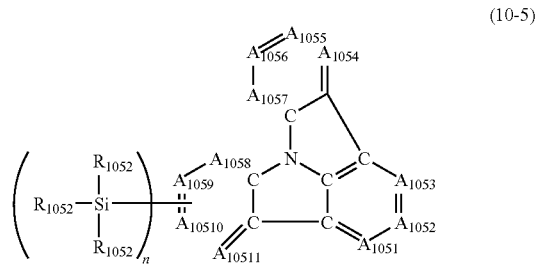

(10-5)

In the formula (10-5), each of $A_{1051}$ to $A_{10511}$ independently represents a nitrogen atom or C—$R_{1051}$; $R_{1051}$ represents a hydrogen atom or a substituent; each $R_{1051}$ may be the same as or different from every other $R_{1051}$; $R_{1052}$ represents a hydrogen atom or a substituent; each $R_{1052}$ may be the same as or different from every other $R_{1052}$; n represents an integer of 1 or more; and a silicon linking group is linked to any one of C atoms in $A_{1051}$ to $A_{10511}$.

$R_{1052}$ is preferably a hydrogen atom, an alkyl group, an aromatic hydrocarbon ring group, an amino group, an alkoxy group, an aryloxy group, an aromatic heterocyclic oxy group, an alkylthio group, an arylthio group, a heterocyclic thio group, a cyano group, an aromatic heterocyclic group, a silyl group or a silyloxy group; more preferably an alkyl group, an aromatic hydrocarbon ring group, an amino group, a cyano group or an aromatic heterocyclic group; further more preferably an alkyl group, an aromatic hydrocarbon ring group, a cyano group or an aromatic heterocyclic group; especially preferably an alkyl group, an aromatic hydrocarbon ring group or an aromatic heterocyclic group; especially preferably an alkyl group or a phenyl group; and most preferably a phenyl group.

n represents an integer of 0 or more, preferably from 0 to 4, and more preferably from 0 to 2.

In the invention, the compound represented by the formula (1) of the invention is not limited with respect to its applications and may be contained in any layer within the organic layer. As to the layer into which the compound represented by the formula (1) of the invention is introduced, the compound represented by the formula (1) of the invention is preferably contained in any one or a plurality of a light emitting layer, a hole injection layer, a hole transport layer, an electron transport layer, an electron injection layer, an exciton blocking layer and a charge blocking layer.

From the viewpoint of bearing the injection transport of a hole, the compound represented by the formula (1) of the invention is preferably contained in a light emitting layer, a hole injection layer or a hole transport layer.

From the viewpoint of stability of a material against the excitation state which is generated through recombination of an electron and a hole, it is especially preferable that the compound represented by any one of the formulae (1) to (10), (4-1) to (4-5) and (10-1) to (10-5) is contained in the light emitting layer.

In the light emitting layer, the compound represented by the formula (1) of the invention is contained in an amount of preferably from 10 to 99% by mass, more preferably from 40 to 99% by mass, and further more preferably from 60 to 99% by mass (In this specification, mass ratio is equal to weight ratio).

In the invention, the compound represented by the formula (1) is preferably contained in any one of the light emitting layer or a layer adjacent to the light emitting layer. In the case where the compound represented by the formula (1) is contained in a layer adjacent to the light emitting layer, it is preferable from the standpoint of uniformity of the film that the layer is constituted of the compound represented by the formula (1) singly.

It is preferable that a hole transport layer is provided between the light emitting layer and an anode and that the compound represented by any one of the formulae (1) to (10), (4-1) to (4-5) and (10-1) to (10-5) is contained in the hole transport layer.

Also, it is preferable that an electron transport layer is provided between the light emitting layer and a cathode and that the compound represented by any one of the formulae (1) to (10), (4-1) to (4-5) and (10-1) to (10-5) is contained in the electron transport layer. According to this, it is possible to efficiently inject an electron from the cathode.

The compound represented by the formula (1) may be contained in both of the light emitting layer and the adjacent layer thereto.

Also, in the case where the compound represented by the formula (1) of the invention is contained in the hole transport layer, the compound represented by the formula (1) of the invention is contained in an amount of preferably from 50 to 100% by mass, more preferably from 70 to 100% by mass, and further more preferably 100% by mass.

In the case where the compound represented by the formula (1) of the invention is contained the electron transport layer, the compound represented by the formula (1) of the invention is contained in an amount of preferably from 50 to 100% by mass, more preferably from 70 to 100% by mass, and further more preferably 100% by mass.

A degree of charge transfer of a host material which is contained in the light emitting layer is preferably $1 \times 10^{-6}$ cm$^2$/Vs or more and not more than $1 \times 10^{-1}$ cm$^2$/Vs, more preferably $5 \times 10^{-6}$ cm$^2$/Vs or more and not more than $1 \times 10^{-2}$ cm$^2$/Vs, further more preferably $1 \times 10^{-5}$ cm$^2$/Vs or more and not more than $1 \times 10^{-2}$ cm$^2$/Vs, and especially preferably $5 \times 10^{-5}$ cm$^2$/Vs or more and not more than $1 \times 10^{-2}$ cm$^2$/Vs.

A $T_1$ level (minimum excitation triplet energy level) of the compound represented by the formula (1) which is contained in the luminescence device of the invention is preferably 60 kcal/mole or more (251.4 kJ/mole or more) and not more than 95 kcal/mole (not more than 398.1 kJ/mole), more preferably 62 kcal/mole or more (259.78 kJ/mole or more) and not more than 85 kcal/mole (not more than 356.15 kJ/mole), and furthermore preferably 65 kcal/mole or more (272.35 kJ/mole or more) and not more than 80 kcal/mole (not more than 335.2 kJ/mole). What the minimum excitation triplet energy level falls within the foregoing range is preferable because a device with a short emission wavelength (for example, a blue device) may be efficiently emitted.

A $T_1$ level (minimum excitation triplet energy level) of the layer adjacent to the light emitting layer of the luminescence device of the invention is preferably 60 kcal/mole or more (251.4 kJ/mole or more) and not more than 95 kcal/mole (not more than 398.1 kJ/mole), more preferably 62 kcal/mole or more (259.78 kJ/mole or more) and not more than 85 kcal/mole (not more than 356.15 kJ/mole), and further more preferably 65 kcal/mole or more (272.35 kJ/mole or more) and not more than 80 kcal/mole (not more than 335.2 kJ/mole).

Next, examples of the compounds represented by the formulae (1) to (10), (4-1) to (4-5) and (10-1) to (10-5) which are used in the organic electroluminescence device of the invention are given below, but it should not be construed that the invention is limited thereto.

1
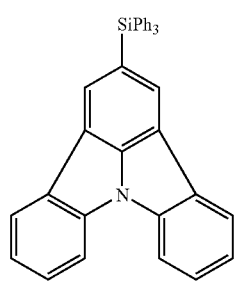

2
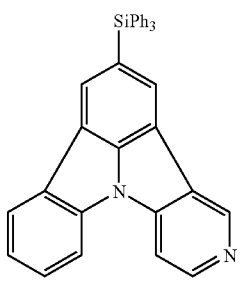

3
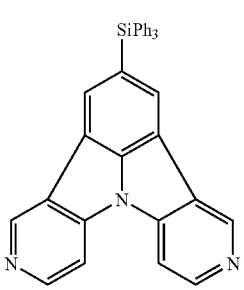

-continued

4
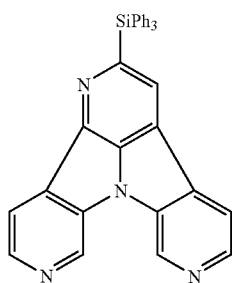

5
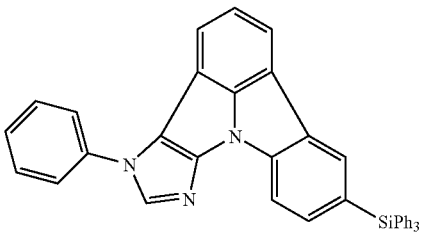

6
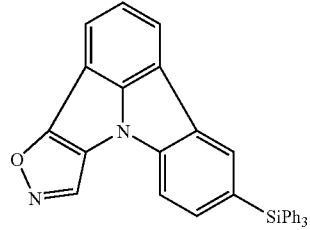

7
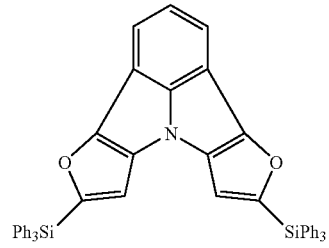

8
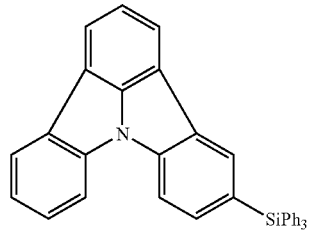

9
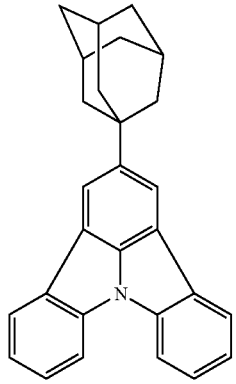

-continued
10
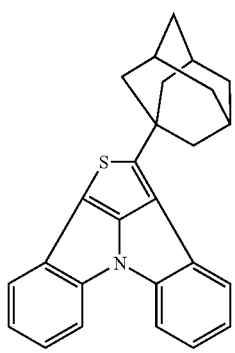
11
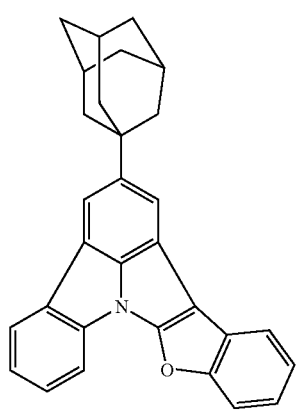
12
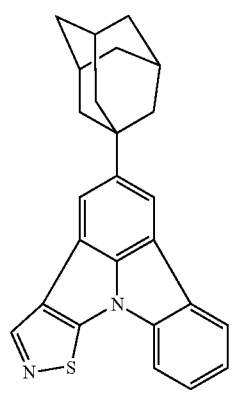
13
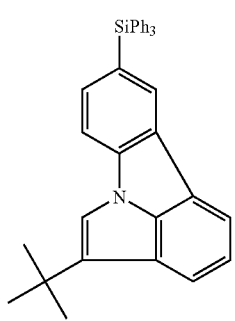
-continued
14
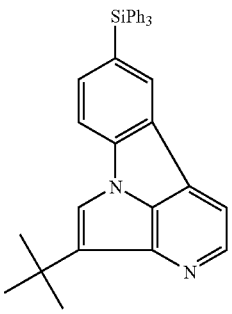
15
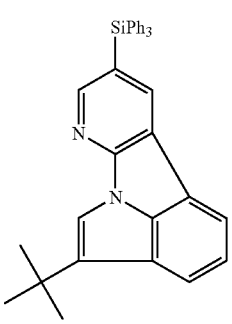
16
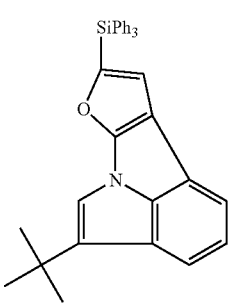
17
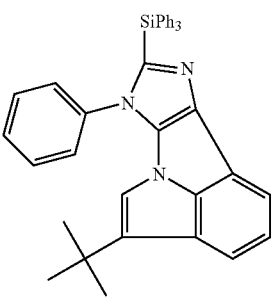
18
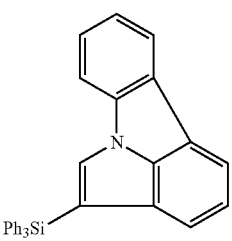

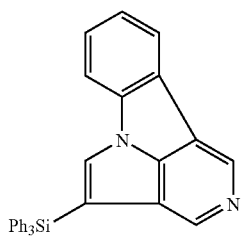
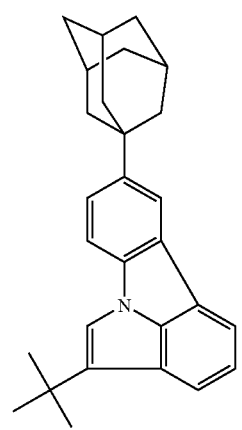
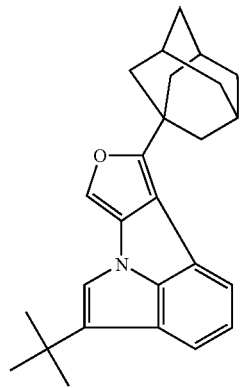
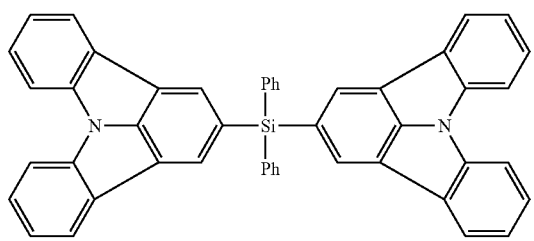
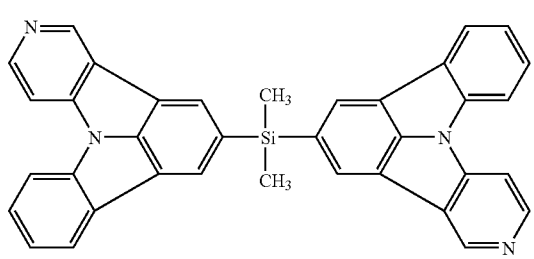
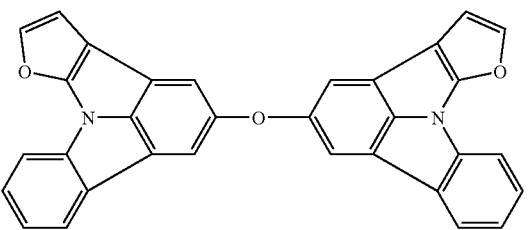
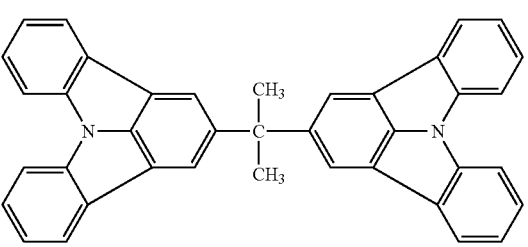
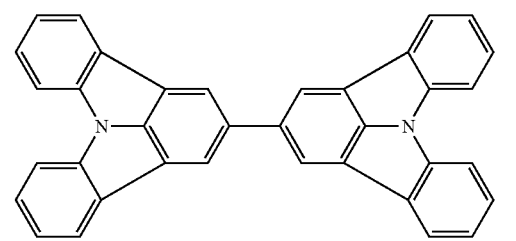
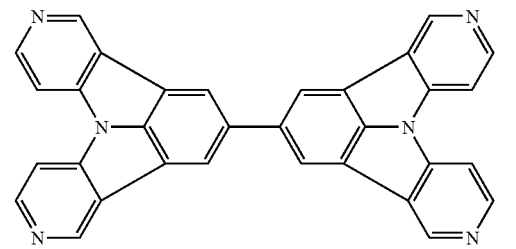
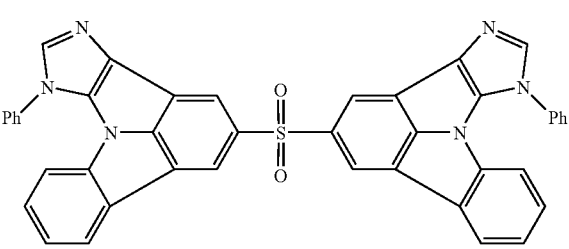
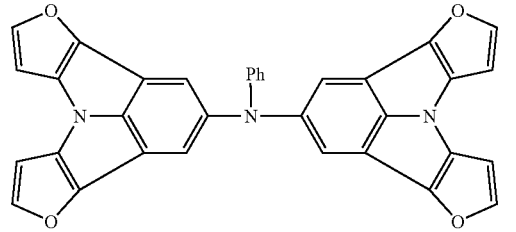

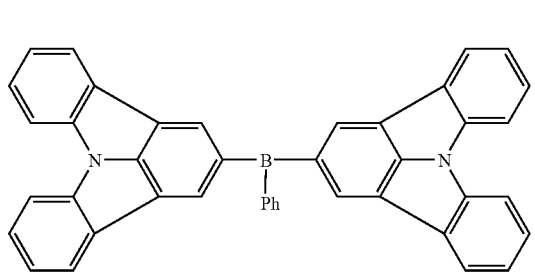
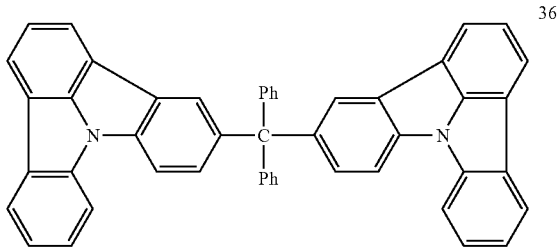
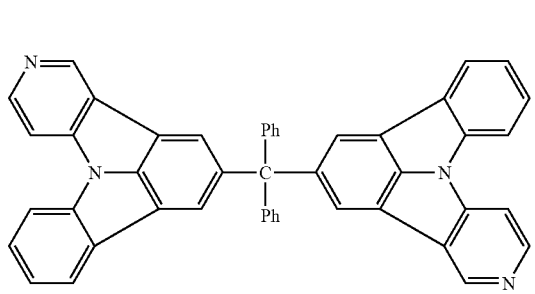
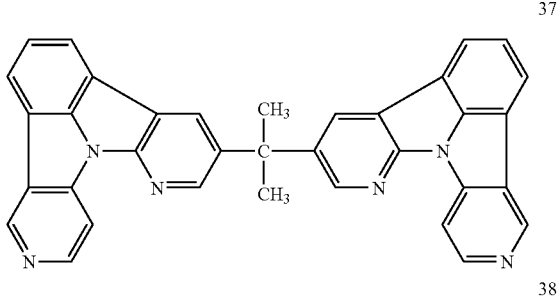
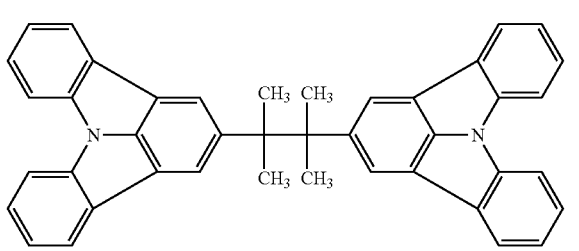
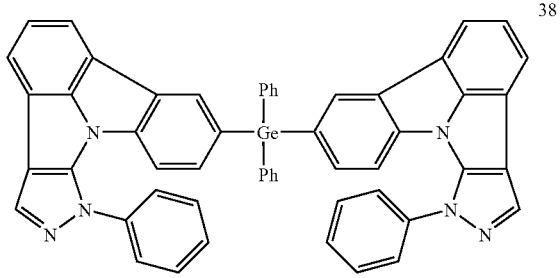
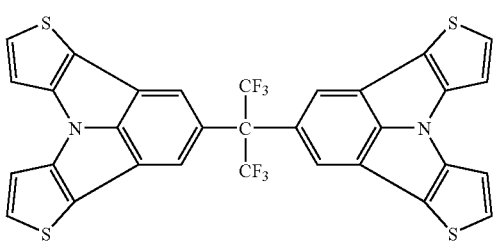
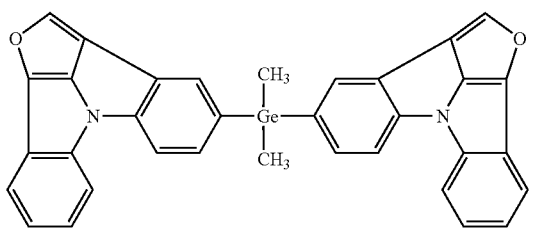
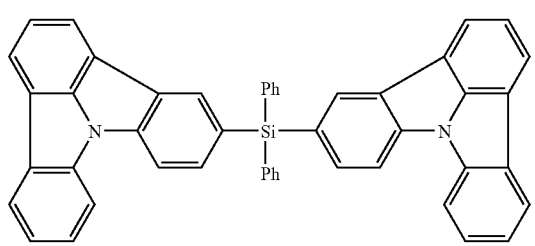
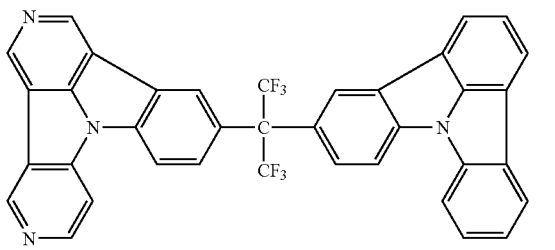
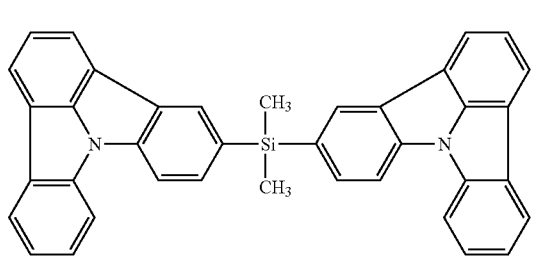
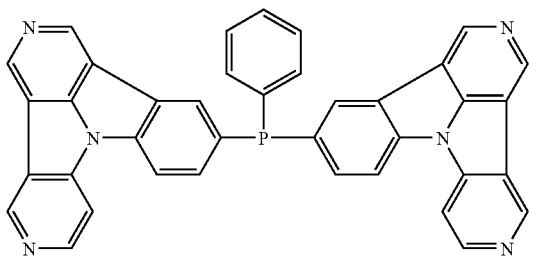

42
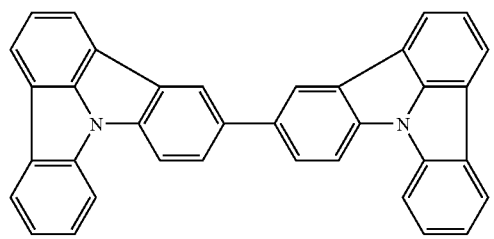
44
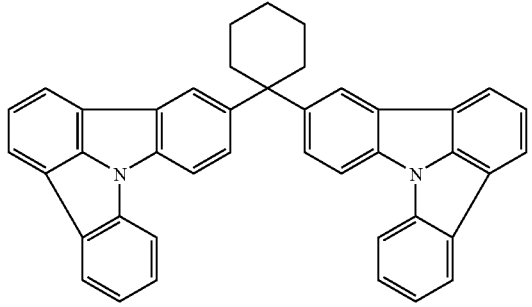
43
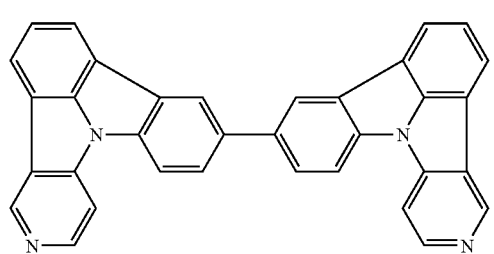
45
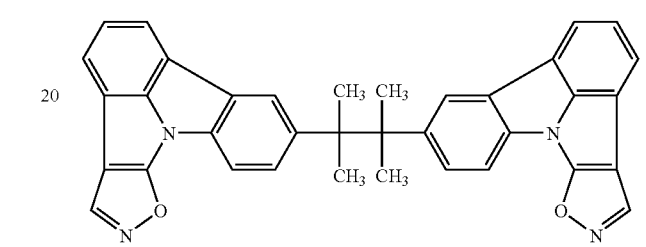
| Compound | Central skeleton | A |
|---|---|---|
| 46 | 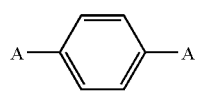 | 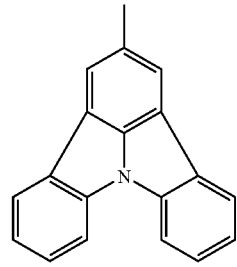 |
| 47 | 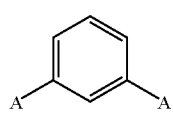 | 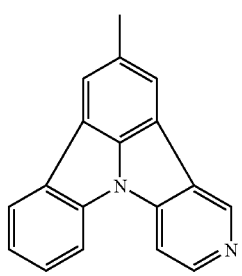 |
| 48 | 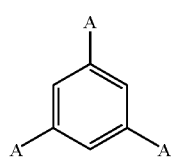 | 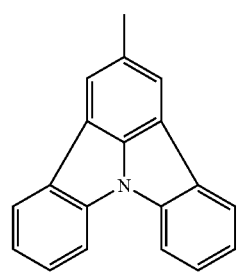 |

-continued

| Compound | Central skeleton | A |
|---|---|---|
| 49 | A—⟨benzene-1,4⟩—A | (structure) |
| 50 | A—⟨benzene-1,3⟩—A | (structure) |
| 51 | A—⟨benzene-1,3,5⟩—A | (structure) |
| 52 | A—⟨pyridine-2,5⟩—A | (structure) |
| 53 | A—⟨pyrazine-2,6⟩—A | (structure) |
| 54 | A—⟨pyridine-2,4,6⟩—A | (structure) |

-continued

| Compound | Central skeleton | A |
|---|---|---|
| 55 | (thiophene with two A substituents at 2,5) | (tricyclic fused structure with central N, two isoxazole rings, and a methyl-substituted benzene) |
| 56 | (furan with two A substituents at 2,5) | (fused polycyclic structure with central N, furan ring, and methyl-substituted benzene) |
| 57 | (N-phenyl pyrrole with A at 2,5) | (fused polycyclic structure with central N, thiophene ring, and methyl-substituted benzene) |
| 58 | A—Si(CH₃)—A with third A | (fused polycyclic structure with central N, two benzene rings, and methyl-substituted benzene) |
| 59 | A—Si(Ph)—A with third A | (fused polycyclic structure with central N, pyridine ring, benzene, and methyl-substituted benzene) |
| 60 | A—Ge(CH₃)—A with third A | (fused polycyclic structure with central N, two furan rings, and a methyl group) |

US 8,174,002 B2
45 46
-continued
| Compound | Central skeleton | A |
|---|---|---|
| 61 | 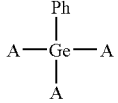 | 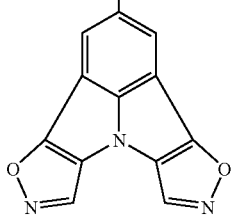 |
| 62 |  | 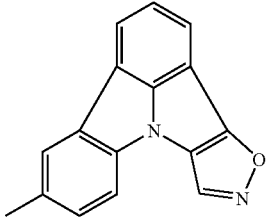 |
| 63 |  | 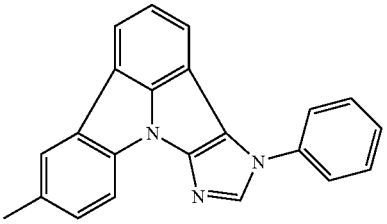 |
| 64 | 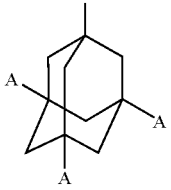 | 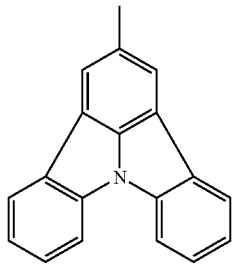 |
| 65 | 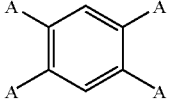 | 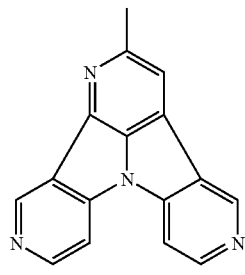 |
| 67 | 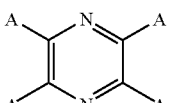 | 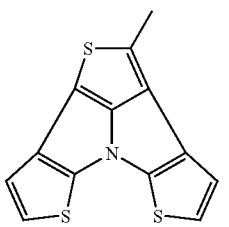 |

-continued

| Compound | Central skeleton | A |
|---|---|---|
| 68 | [trimethylsilyl skeleton] | [structure with two N-phenyl pyrazole fused rings and methyl group] |
| 69 | [trimethylgermyl skeleton] | [structure with carbazole fused isoxazole and methyl group] |
| 70 | [hexasubstituted benzene with A groups] | [structure with carbazole fused benzothiophene and methyl group] |

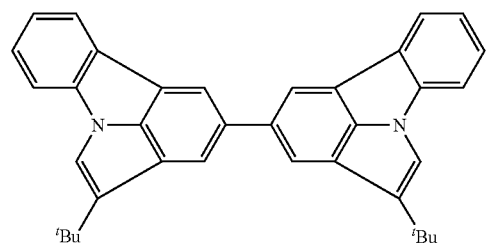
75
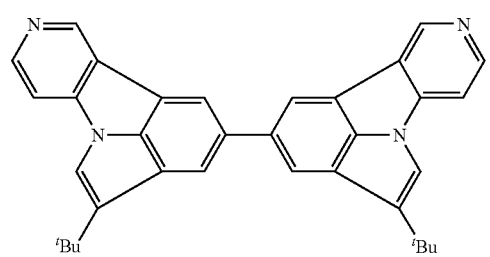
76
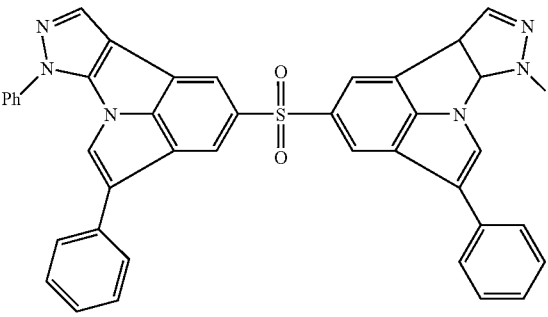
77
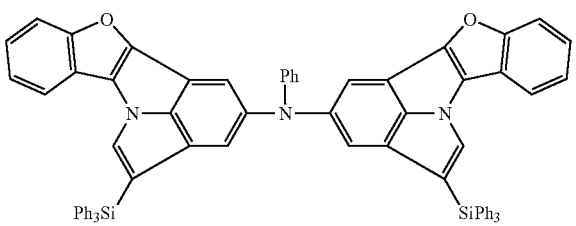
78
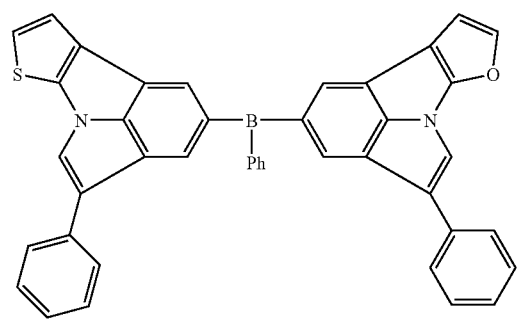
79
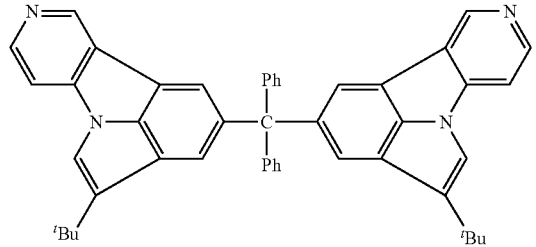
80
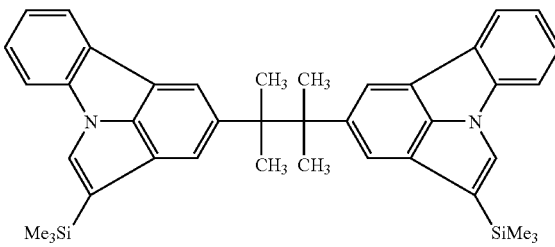
81
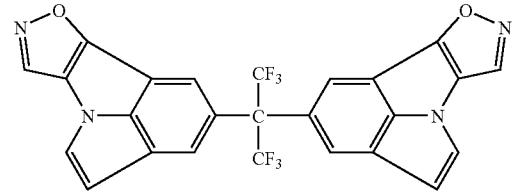
82
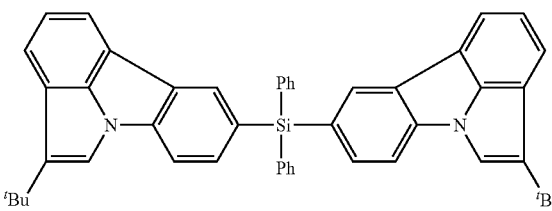
83
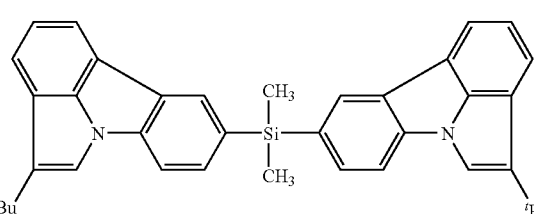
84
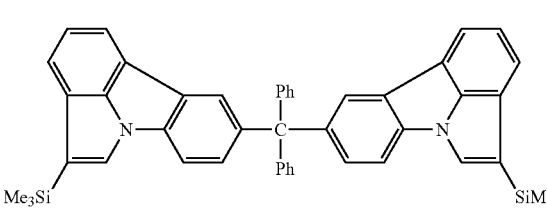
85
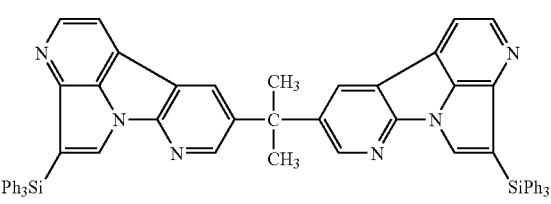
86

87
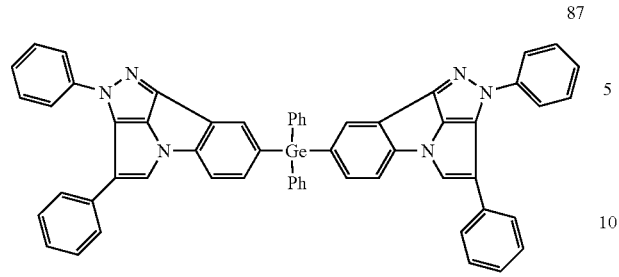
88
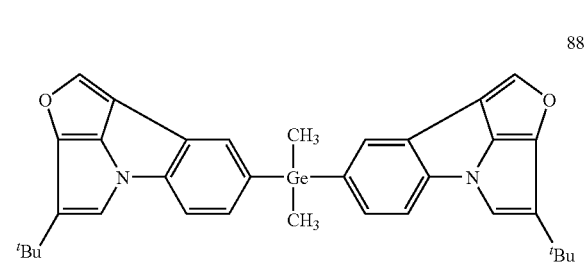
89
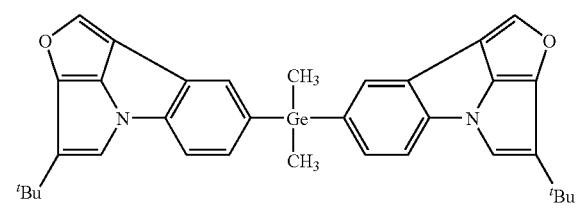
90
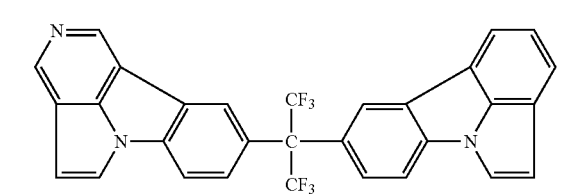
91
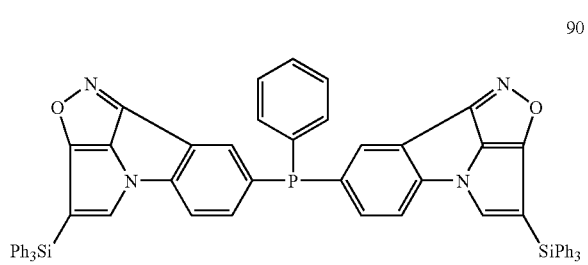
92
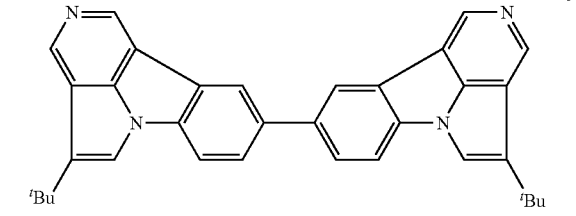
93
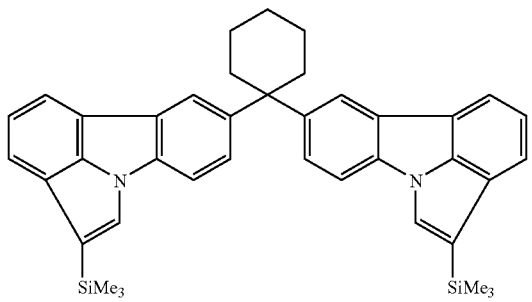
94
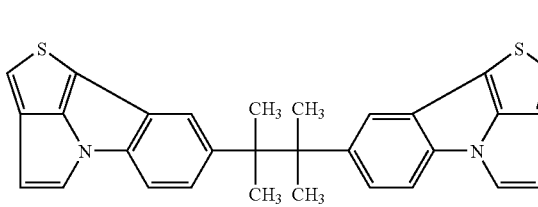
95
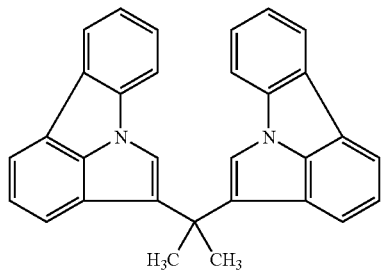
96
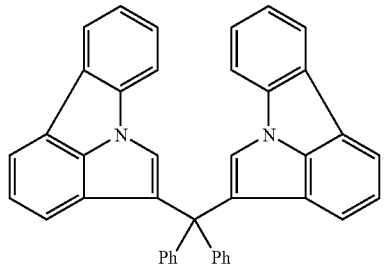
97
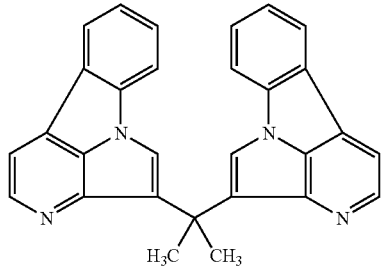
98
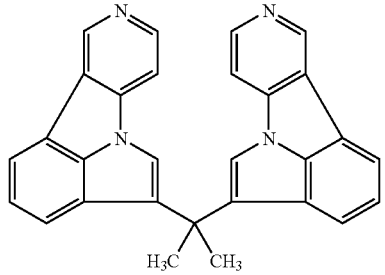

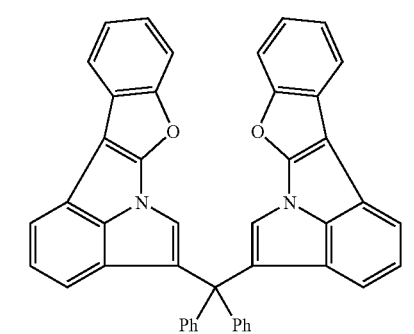
99
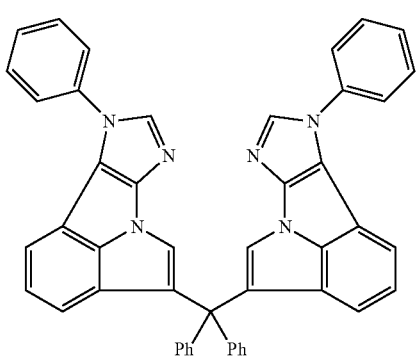
100
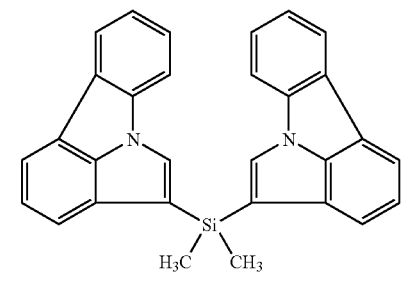
101
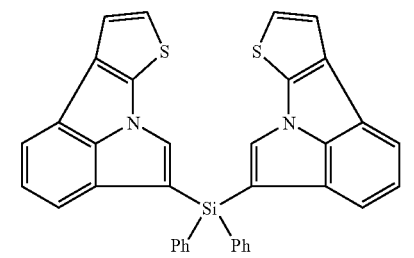
102
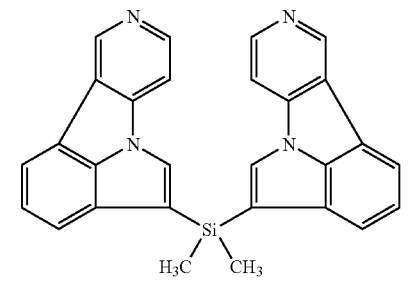
103
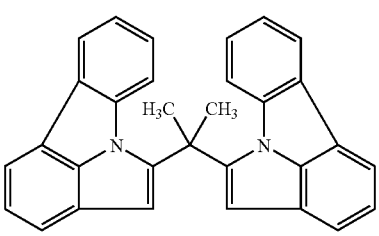
104
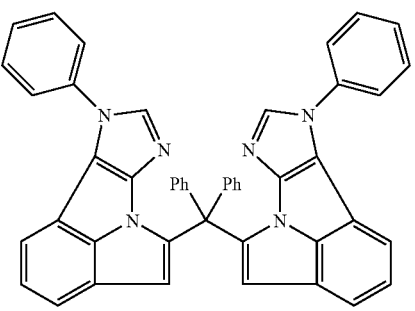
105
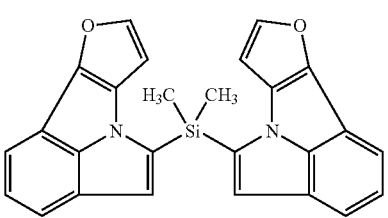
106
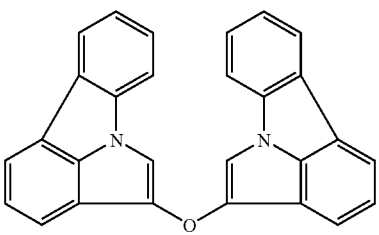
107
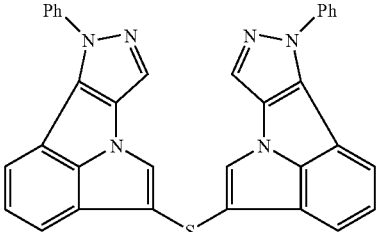
108
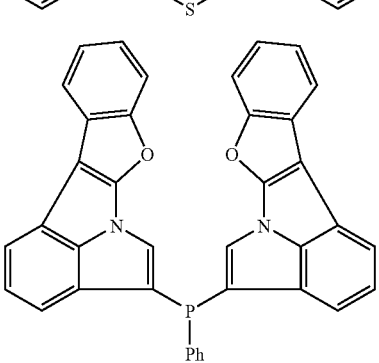
109

| Compound | Central skeleton | A |
|---|---|---|
| 110 |  | 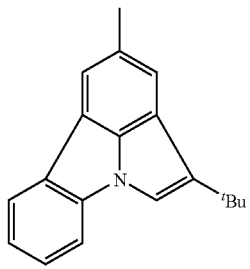 |
| 111 | 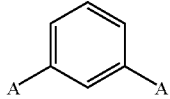 | 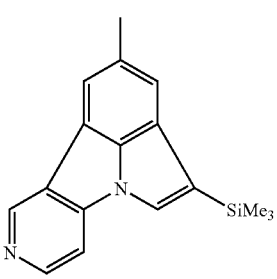 |
| 112 | 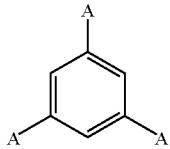 | 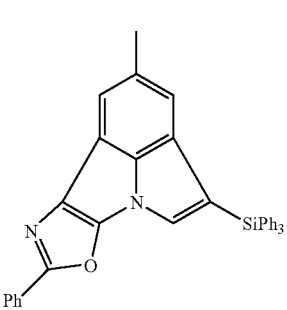 |
| 113 |  | 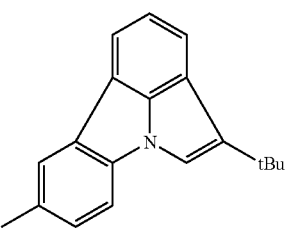 |
| 114 | 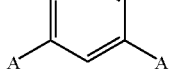 | 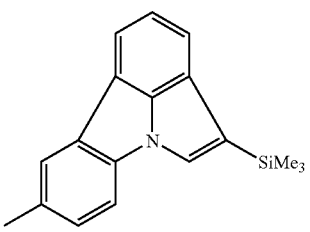 |
| 115 | 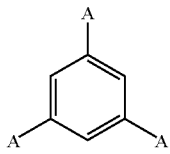 | 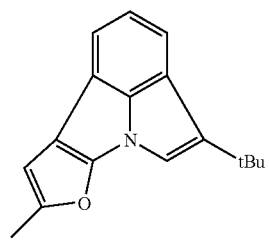 |

-continued

| Compound | Central skeleton | A |
|---|---|---|
| 116 | | |
| 117 | | |
| 118 | | |
| 119 | | |
| 120 | | |
| 121 | | |

-continued
| Compound | Central skeleton | A |
|---|---|---|
| 122 | 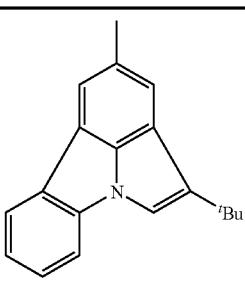 | 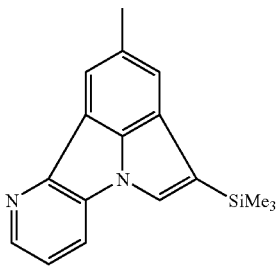 |
| 123 | 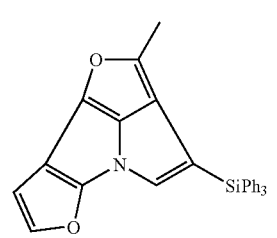 | 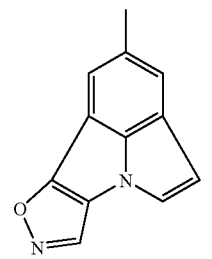 |
| 124 | 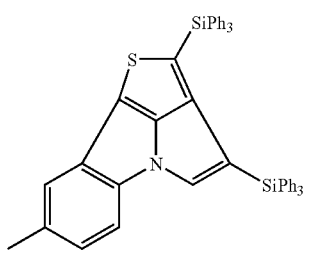 | 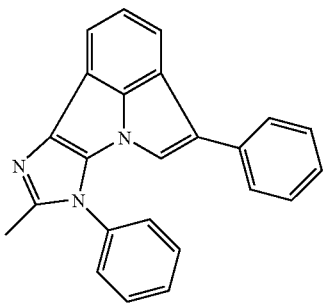 |
| 125 | | |
| 126 | | |
| 127 | | |

-continued

| Compound | Central skeleton | A |
|---|---|---|
| 128 | (adamantane with 4 A substituents) | (indolizine-fused tricyclic with methyl and tBu) |
| 129 | (benzene with 4 A substituents at 1,2,4,5) | (diaza tricyclic fused system with methyl and tBu) |
| 130 | (pyrazine with 4 A substituents) | (dithieno-fused tricyclic with methyl and SiMe₃) |
| 131 | (SiMe₄ center) | (pyrazole-fused tricyclic with N-phenyl, phenyl, and methyl) |
| 132 | (GeMe₄ center) | (furan-fused tricyclic with two SiMe₃ groups and methyl) |
| 133 | (benzene with 6 A substituents) | (indolizine tricyclic with methyl and tBu) |

The compounds represented by the formulae (1) to (10) may be synthesized by various known synthesis methods described in, for example, *J. Chem. Soc.*, pages 1945 to 1956 (1939), *J. Chem. Soc.*, pages 2750 to 2755 (1958), etc. The compounds represented by the formulae (4-1) to (4-5) and (10-1) to (10-5) may be synthesized using the foregoing intermediate D by various known synthesis methods described in, for example, *J. Org. Chem.*, 20, pages 73 to 78 (1955), *Org. Lett.*, 7, pages 2829 to 2832 (2005), *J. Am. Chem. Soc.*, 128, pages 8549 to 8558 (2006), *Chem. Lett.*, 36, pages 1156 to 1157 (2007), etc.

A glass transition temperature of the compound represented by the formula (1) is preferably 130° C. or higher and not higher than 450° C., more preferably 140° C. or higher and not higher than 450° C., and further more preferably 160° C. or higher and not higher than 450° C. What the glass transition temperature of the compound represented by the formula (1) falls within the foregoing range is preferable because heat resistance and durability of the device may be expected to be enhanced.

[Organic Electroluminescence Device]

The device of the invention includes a cathode and an anode on a substrate and includes an organic layer containing a light emitting layer between the both electrodes. In view of natures of the luminescence device, it is preferable that at least one electrode of the anode and the cathode is transparent.

In the invention, as to a form of lamination of the organic layers, an embodiment in which a hole transport layer, a light emitting layer and an electron transport layer are laminated in this order from the anode side is preferable. Furthermore, a hole injection layer is provided between the hole transport layer and the anode, and/or an electron transporting interlayer is provided between the light emitting layer and the electron transport layer. Also, a hole transporting interlayer may be provided between the light emitting layer and the hole transport layer, and an electron injection layer may be similarly provided between the cathode and the electron transport layer.

Each of the layers may be divided into plural secondary layers.

Each of the layers configuring the organic layer may be suitably fabricated by any method, for example, a dry fabrication process such as a vapor deposition process and a sputtering process, a transfer process, a printing process, a coating process, an inkjet process, a spraying process, etc.

Next, each of the elements configuring the organic EL device of the invention is described.

<Substrate>

It is preferable that the substrate is a substrate which does not scatter or decay light emitted from the organic compound layer. Specific examples thereof include inorganic materials such as yttria-stabilized zirconia (YSZ) and a glass; and organic materials such as polyesters (for example, polyethylene terephthalate, polybutylene phthalate, polyethylene naphthalate, etc.), polystyrenes, polycarbonates, polyethersulfones, polyarylates, polyimides, polycycloolefins, norbornene resins and poly(chlorotrifluoroethylene).

For example, in the case where a glass is used as the substrate, with respect to the material quality thereof, for the purpose of reducing the amount of eluted ions from the glass, it is preferred to use a no-alkali glass. Also, in the case of using a soda lime glass, it is preferred to use a glass to which barrier coating with silica, etc. has been applied. In the case of an organic material, it is preferable that the organic material is excellent in heat resistance, dimensional stability, solvent resistance, electrical insulating properties and processability.

The substrate is not particularly limited with respect to its shape, structure and size and so on and may be properly chosen depending upon the application and purpose and the like of the organic EL device. In general, the shape of the substrate is preferably a platy shape. The structure of the substrate may be a single layer structure or may be a laminate structure. Also, the substrate may be formed of a single component or may be formed of two or more components.

Though the substrate may be colorless transparent or may be colored transparent, it is preferably colorless transparent from the standpoint that it does not scatter or decay light emitted from the light emitting layer.

The substrate may be provided with a moisture permeation preventing layer (gas barrier layer) on the front or back surface thereof.

As a material of the moisture permeation preventing layer (gas barrier layer), an inorganic material such as silicon nitride and silicon oxide is suitably used. The moisture permeation preventing layer (gas barrier layer) may be fabricated by, for example, a high-frequency sputtering process, etc.

In the case of using a thermoplastic substrate, a hard coat layer, an undercoat layer or the like may be further provided as the need arises.

<Anode>

In general, the anode may have a function as an electrode for feeding a hole into the organic compound layer. The anode is not particularly limited with respect to its shape, structure and size and so on and may be properly chosen among known electrode materials depending upon the application and purpose of the organic EL device. As described previously, the anode is usually provided as a transparent anode.

Suitable examples of a material of the anode include metals, alloys, metal oxides, conductive compounds and mixtures thereof. Specific examples of the anode material include conductive metal oxides such as tin oxide doped with antimony, fluorine, etc. (for example, ATO, FTO, etc.), tin oxide, zinc oxide, indium oxide, indium tin oxide (ITO) and indium zinc oxide (IZO); metals such as gold, silver, chromium and nickel; mixtures or laminates of the foregoing metal and conductive metal oxide; inorganic conductive substances such as copper iodide and copper sulfide; organic conductive materials such as polyaniline, polythiophene and polypyrrole; and laminates thereof with ITO. Of these, conductive metal oxides are preferable; and ITO is especially preferable from the standpoints of productivity, high conductivity, transparency and so on.

The anode may be fabricated on the foregoing substrate according to a method properly chosen while taking into consideration the adaptability to the material constituting the anode among, for example, a wet system (for example, a printing system, a coating system, etc.), a physical system (for example, a vacuum vapor deposition process, a sputtering process, an ion plating process, etc.), a chemical system (for example, a CVD process, a plasma CVD process, etc.) and so on. For example, in the case where ITO is chosen as the material of the anode, the fabrication of the anode can be carried out according to a direct current or high-frequency sputtering process, a vacuum vapor deposition process, an ion plating process, etc.

In the organic EL device of the invention, though the fabrication position of the anode is not particularly limited and may be properly chosen depending upon the application and purpose of the organic EL device, it is preferable that the anode is fabricated on the substrate. In that case, the anode may be fabricated on the whole or a part of one surface of the substrate.

Patterning in fabricating the anode may be carried out by means of chemical etching such as photolithography or may be carried out by means of physical etching with a laser, etc. Also, patterning may be carried out by superimposing a mask and undergoing vacuum vapor deposition or sputtering or the like or may be carried out by a liftoff process or a printing process.

A thickness of the anode may be properly chosen depending upon the material constituting the anode and cannot be unequivocally defined. The thickness of the anode is usually from about 10 nm to 50 μm, and preferably from 50 nm to 20 μm.

A resistivity value of the anode is preferably not more than $10^3 \Omega/\square$. In the case where the anode is transparent, the anode may be colorless transparent or may be colored transparent. In order to collect light emission from the transparent anode side, its transmittance is preferably 60% or more, and more preferably 70% or more.

The transparent anode is described in detail in *New Developments of Transparent Conductive Films*, supervised by Yutaka Sawada (published by CMC Publishing Co., Ltd., 1999), and the matters described therein are applicable to the invention. In the case of using a plastic base material with low heat resistance, a transparent anode obtained by using ITO or IZO and fabricating it at a low temperature of not higher than 150° C. is preferable.

<Cathode>

In general, the cathode may have a function as an electrode for injecting an electron into the organic compound layer. The cathode is not particularly limited with respect to its shape, structure and size and so on and may be properly chosen among known electrode materials depending upon the application and purpose of the organic EL device.

Examples of a material constituting the cathode include metals, alloys, metal oxides, electrically conductive compounds and mixtures thereof. Specific examples of the cathode material include alkali metals (for example, Li, Na, K, Cs, etc.), alkaline earth metals (for example, Mg, Ca, etc.), gold, silver, lead, aluminum, a sodium-potassium alloy, a lithium-aluminum alloy, a magnesium-silver alloy, indium and rare earth metals (for example, ytterbium, etc.). Though such a material may be used singly, two or more kinds thereof may be suitably used jointly from the viewpoint of making both stability and electron injection properties compatible with each other.

Of these, alkali metals and alkaline earth metals are preferable as the material constituting the cathode from the standpoint of electron injection properties; and materials composed mainly of aluminum are preferable from the standpoint of excellent storage stability.

The material composed mainly of aluminum as referred to herein refers to a single substance of aluminum or an alloy of aluminum and from 0.01 to 10% by mass of an alkali metal or an alkaline earth metal or a mixture thereof (for example, a lithium-aluminum alloy, a magnesium-aluminum alloy, etc.).

The material of the cathode is disclosed in detail in JP-A-2-15595 and JP-A-5-121172, and materials disclosed in these patent documents are also applicable in the invention.

The method for fabricating the cathode is not particularly limited, and the fabrication of the cathode may be carried out according to a known method. The cathode may be fabricated according to a method properly chosen while taking into consideration the adaptability to the material constituting the cathode among, for example, a wet system (for example, a printing system, a coating system, etc.), a physical system (for example, a vacuum vapor deposition process, a sputtering process, an ion plating process, etc.), a chemical system (for example, a CVD process, a plasma CVD process, etc.) and so on. For example, in the case where a metal or the like is chosen as the material of the cathode, the cathode may be fabricated by a simultaneous or sequential sputtering process of one or two or more kinds thereof or the like.

Patterning in fabricating the cathode may be carried out by means of chemical etching such as photolithography or may be carried out by means of physical etching with a laser, etc. Also, patterning may be carried out by superimposing a mask and undergoing vacuum vapor deposition or sputtering or the like or may be carried out by a liftoff process or a printing process.

The fabrication position of the cathode is not particularly limited. The cathode may be fabricated on the whole or a part of the organic layer.

Also, a dielectric layer made of a fluoride or oxide of an alkali metal or an alkaline earth metal, etc. may be inserted in a thickness of from 0.1 to 5 nm between the cathode and the organic compound layer. This dielectric layer may also be considered as a sort of the electron injection layer. The dielectric layer may be fabricated by, for example, a vacuum vapor deposition process, a sputtering process, an ion plating process or the like.

A thickness of the cathode may be properly chosen depending upon the material constituting the cathode and cannot be unequivocally defined. The thickness of the cathode is usually from about 10 nm to 5 μm, and preferably from 50 nm to 1 μm.

Also, the cathode may be transparent or may be opaque. A transparent cathode may be fabricated by thinly fabricating the material of the cathode in a thickness of from 1 to 10 nm and further laminating a transparent conductive material such as ITO and IZO.

<Organic Layer>

The organic layer in the invention is described.

The organic EL device of the invention has at least one organic layer including the light emitting layer. As described previously, examples of other organic layers than the light emitting layer include respective layers such as a hole transport layer, an electron transport layer, a charge blocking layer, a hole injection layer and an electron injection layer.

In the organic EL device of the invention, the respective layers configuring the organic layer may be suitably fabricated by any of a dry fabrication process (for example, a vapor deposition process, a sputtering process, etc.), a wet coating system, a transfer process, a printing process, an inkjet system and so on.

—Light Emitting Layer—

The light emitting layer is a layer having functions such that at the time of impressing an electric field, it receives a hole from the anode, the hole injection layer or the hole transport layer, receives an electron from the cathode, the electron injection layer or the electron transport layer and provides a site of recombination of the hole and the electron, thereby achieving light emission.

Also, the light emitting layer may be configured of only a light emitting material or may be configured as a mixed layer of a host material and a light emitting material.

Also, the light emitting layer may be made of a single layer or two or more layers. The respective layers may emit light in a different luminescent color from each other.

<Light Emitting Material>

Though the light emitting material may be a fluorescent material or a phosphorescent material, it is more preferably a phosphorescent material. A dopant may be made of a single kind or two or more kinds.

It is preferable that the light emitting layer contains a phosphorescent material.

It is preferable that the host material is a charge transport material. The host material may be made of a single kind or two or more kinds. Examples thereof include a configuration in which an electron transporting host material and a hole transporting host material are mixed. Furthermore, the light emitting layer may contain a material which does not have charge transporting properties and which does not emit light.

<<Fluorescent Material>>

In general, examples of the fluorescent material include benzoxazole, benzimidazole, benzothiazole, styrylbenzene, polyphenyl, diphenylbutadiene, tetraphenylbutadiene, naphthalimide, coumarin, pyran, perinone, oxadiazole, aldazine, pyralizine, cyclopentadiene, bisstyrylanthracene, quinacridone, pyrolopyridine, thiadiazolopyridine, cyclopentadiene, styrylamine, aromatic dimethylidine compounds, condensed polycyclic aromatic compounds (for example, anthracene, phenanthroline, pyrene, perylene, rubrene, pentacene, etc.), various metal complexes (represented by metal complexes of 8-quinolinol, pyrromethene complexes and rare earth complexes), polymer compounds (for example, polythiophene, polyphenylene, polyphenylene vinylene), organic silanes and derivatives thereof.

<<Phosphorescent Material>>

In general, examples of the phosphorescent material include complexes containing a transition metal atom or a lanthanoid atom.

Though the transition metal atom is not particularly limited, preferred examples thereof include ruthenium, rhodium, palladium, tungsten, rhenium, osmium, iridium, gold, silver, copper and platinum. Of these, rhenium, iridium and platinum are more preferable; and iridium and platinum are further more preferable.

Examples of the lanthanoid atom include lanthanum, cerium, praseodymium, neodymium, samarium, europium, gadolinium, terbium, dysprosium, holmium, erbium, thulium, ytterbium and lutetium. Of these lanthanoid atoms, neodymium, europium and gadolinium are preferable.

Examples of a ligand of the complex include ligands described in, for example, G. Wilkinson, et al., *Comprehensive Coordination Chemistry*, published by Pergamon Press, 1987; H. Yersin, *Photochemistry and Photophysics of Coordination Compounds*, published by Springer-Verlag, 1987; and YAMAMOTO, Akio, *Organometallic Chemistry—Principles and Applications*, published by Shokabo Publishing Co., Ltd., 1982.

Specifically, as the ligand, halogen ligands (preferably a chlorine ligand), aromatic carbocyclic ligands (preferably aromatic carbocyclic ligands having from 5 to 30 carbon atoms, more preferably from 6 to 30 carbon atoms, further more preferably from 6 to 20 carbon atoms, and especially preferably from 6 to 12 carbon atoms; for example, a cyclopentadienyl anion, a benzene anion, a naphthyl anion, etc.), nitrogen-containing heterocyclic ligands (preferably nitrogen-containing heterocyclic ligands having from 5 to 30 carbon atoms, more preferably from 6 to 30 carbon atoms, further more preferably from 6 to 20 carbon atoms, and especially preferably from 6 to 12 carbon atoms; for example, phenylpyridine, benzoquinoline, quinolinol, bipyridyl, phenanthroline, etc.), diketone ligands (for example, acetylacetone, etc.), carboxylic acid ligands (preferably carboxylic acid ligands having from 2 to 30 carbon atoms, more preferably from 2 to 20 carbon atoms, and further more preferably from 2 to 16 carbon atoms; for example, an acetic acid ligand, etc.), alcoholate ligands (preferably alcoholate ligands having from 1 to 30 carbon atoms, more preferably from 1 to 20 carbon atoms, and further more preferably from 6 to 20 carbon atoms; for example, a phenolate ligand, etc.), silyloxy ligands (preferably silyloxy ligands having from 3 to 40 carbon atoms, more preferably from 3 to 30 carbon atoms, and further more preferably from 3 to 20 carbon atoms; for example, a trimethylsilyloxy ligand, a dimethyl-tert-butylsilyloxy ligand, a triphenylsilyloxy ligand, etc.), a carbon monoxide ligand, an isonitrile ligand, a cyano ligand, phosphorus ligands (preferably phosphorus ligands having from 3 to 40 carbon atoms, more preferably from 3 to 30 carbon atoms, further more preferably from 3 to 20 carbon atoms, and especially preferably from 6 to 20 carbon atoms; for example, a triphenylphosphine ligand, etc.), thiolate ligands (preferably thiolate ligands having from 1 to 30 carbon atoms, more preferably from 1 to 20 carbon atoms, and further more preferably from 6 to 20 carbon atoms; for example, a phenylthiolate ligand, etc.) and phosphine oxide ligands (preferably phosphine oxide ligands having from 3 to 30 carbon atoms, more preferably from 8 to 30 carbon atoms, and further more preferably from 18 to 30 carbon atoms; for example, a triphenylphosphine oxide ligand, etc.), with nitrogen-containing heterocyclic ligands being more preferable.

The complex may contain one transition metal atom in the compound thereof, or may be a so-called polynuclear complex containing two or more transition metal atoms therein. The complex may contain metal atoms of a different kind at the same time.

Among them, specific examples of the light emitting material include, for example, U.S. Pat. No. 6,303,238B1, U.S. Pat. No. 6,097,147, WO 00/57676, WO 00/70655, WO 01/08230, WO 01/39234A2, WO 01/41512A1, WO 02/02714A2, WO 02/15645A1, WO 02/44189A1, WO 05/19373A2, JP-A-2001-247859, JP-A-2002-302671, JP-A-2002-117978, JP-A-2003-133074, JP-A-2002-235076, JP-A-2003-123982, JP-A-2002-170684, EP1211257, JP-A-2002-226495, JP-A-2002-234894, JP-A-2001-247859, JP-A-2001-298470, JP-A-2002-173674, JP-A-2002-203678, JP-A-2002-203679, JP-A-2004-357791, JP-A-2006-256999, JP-A-2007-19462, JP-A-2007-84635, JP-A-2007-96259, etc. Above all, more preferred examples of the light emitting material include Ir complexes, Pt complexes, Cu complexes, Re complexes, W complexes, Rh complexes, Ru complexes, Pd complexes, Os complexes, Eu complexes, Tb complexes, Gd complexes, Dy complexes and Ce complexes. In particular, Ir complexes, Pt complexes and Re complexes are preferable; and Ir complexes, Pt complexes and Re complexes containing at least one coordination mode of a metal-carbon bond, a metal-nitrogen bond, a metal-oxygen bond and a metal-sulfur bond are more preferable. Furthermore, from the viewpoints of luminous efficiency, driving durability, chromaticity, etc., Ir complexes, Pt complexes and Re complexes each containing a tridentate or multidentate ligand are especially preferable, with Ir complexes and Pt complexes being the most preferable. Above all, Pt complexes containing a tetradentate ligand are especially preferable.

Though the light emitting material is not particularly limited, it is preferred to use a phosphorescent material; it is more preferred to use an iridium complex phosphorescent material or a platinum complex phosphorescent material; and it is especially preferred to use a platinum complex phosphorescent material having a tetradentate ligand. Other phosphorescent material may be used jointly.

Examples of the complex phosphorescent material include compounds described in *Coordination Chemistry Reviews*, 250 (2006), pages 2093 to 2126.

Examples of the iridium complex phosphorescent material include compounds disclosed in WO 00/70655, WO 01/41512, WO 02/5645, JPA-2002-117978, WO 04/085450, WO 06/121811, WO 05/019373 and WO 05/113704.

Examples of the platinum complex phosphorescent material include compounds disclosed in WO 00/57676.

More specifically, as the platinum complex (phosphorescent) material having a tetradentate ligand, compounds disclosed in U.S. Pat. No. 6,653,654, WO 2004/099339, WO 04/108857, JP-A-2005-310733, JP-A-2005-317516, JP-A-2006-261623, JP-A-2006-93542, JP-A-2006-256999, WO 06/098505, JP-A-2007-19462, JP-A-2007-96255, JP-A-2007-96259, WO 05/042444, JP-A-2006-232784 and WO 05/042550 are preferable.

The platinum complex (phosphorescent) materials having tetradentate ligands are preferably those containing 2-arylpyridine derivatives, 2-(1-pyrazolyl)pyridine derivatives or 1-arylpyrazole derivatives as partial structures of their respective ligands, more preferably those containing 2-arylpyridine derivatives or 2-(1-pyrazolyl)pyridine derivatives as partial structures of their respective ligands, especially preferably those containing 2-arylpyridine derivatives as partial structures of their respective ligands.

Also, the partial structures of ligands (for example, 2-arylpyridine derivatives, 2-(1-pyrazolyl)pyridine derivatives, 1-arylpyrazole derivatives, etc.) are linked together at their appropriate sites and form a tetradentate ligand.

In the case of containing 2-arylpyridine derivatives as partial structures of a ligand, it is preferable that the linking site of each derivative is the 6-position of the pyridine ring or the aryl carbon in the position meta to the pyridine ring; it is more preferable that their pyridine rings are linked at the 6-position each other or their aryl carbons in the positions meta to the pyridine rings are linked; and it is especially preferable that their pyridine rings are linked at the 6-position each other.

In the case of containing 2-(1-pyrazolyl)pyridine derivatives as partial structures of a ligand, it is preferable that the linking site of each derivative is the 6-position of the pyridine ring or the 4-position of the 1-pyrazolyl group; it is more preferable that their pyridine rings are linked at the 6-position each other or their 1-pyrazolyl groups are linked at the 4-position each other; and it is especially preferable that their pyridine rings are linked at the 6-position each other.

In the case of containing 1-arylpyrazole derivatives as partial structures of a ligand, it is preferable that the linking site of each derivative is the 3-position of the pyrazole ring or the aryl carbon in the position meta to the pyrazole ring; it is more preferable that their pyrazole rings are linked at the 3-position each other or their aryl carbons in the positions meta to the pyrazole rings are linked; and it is especially preferable that their pyrazole rings are linked at the 3-position each other.

Though a structure for linking the foregoing partial structure of the ligand may be either a single bond or a divalent linking group, it is preferably a divalent linking group. As the divalent linking group, for example, a methylene linkage, an ethylene linkage, a phenylene linkage, a nitrogen atom linkage, an oxygen atom linkage, a sulfur atom linkage and a silicon atom linkage are preferable; a methylene linkage, a nitrogen atom linkage and a silicon atom linkage are more preferable; and a methylene linkage is especially preferred. Specific examples of the methylene linking group include a methylene group (—$CH_2$—), a methylmethylene group (—CHMe—), a fluoromethylmethylene group (—CFMe—), a dimethylmethylene group (—$CMe_2$-), a methylphenylmethylene group (—CMePh-), a diphenylmethylene group (—$CPh_2$-), a 9,9-fluorenediyl group, a 1,1-cyclopentadiyl group and a 1,1-cyclohexanediyl group. Of these, a dimethylmethylene group, a diphenylmethylene group, a 9,9-fluorenediyl group, a 1,1-cyclopentanediyl group and a 1,1-cyclohexanediyl group are preferable; a dimethylmethylene group, a diphenylmethylene group and a 1,1-cyclohexanediyl group are more preferable; and a dimethylmethylene group is especially preferable.

Also, one of complexes which are more preferable as the platinum complex (phosphorescent) material having a tetradentate ligand is a Pt complex represented by the following formula (A).

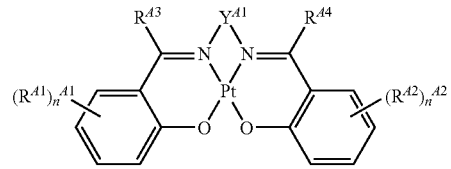

Formula (A)

In the formula (A), each of $R^{43}$ and $R^{44}$ independently represents a hydrogen atom or a substituent; and each of $R^{41}$ and $R^{42}$ independently represents a substituent. In the case of containing a plurality of each of $R^{41}$ and $R^{42}$, each $R^{41}$ may be the same as or different from every other $R^{41}$ and may be linked to each other to form a ring; and each $R^{42}$ may be the same as or different from every other $R^{42}$ and may be linked to each other to form a ring. Each of $n^{41}$ and $n^{42}$ independently represents an integer of from 0 to 4. $Y^{41}$ represents a linking group.

The substituent represented by each of $R^{41}$, $R^{42}$, $R^{43}$ and $R^{44}$ may be arbitrarily chosen among those which are exemplified previously as the group A of substituent.

The linking group represented by $Y^{41}$ may be arbitrarily chosen among those which are exemplified below as the following group A of linking group.

(Group A of Linking Group)

Examples of the group A of linking group include an alkylene group (for example, methylene, ethylene, propylene, etc.), an arylene group (for example, phenylene, naphthalenediyl, etc.), a heteroarylene group (for example, pyridinediyl, thiophenediyl, etc.), an imino group (—NR—) (for example, a phenylimino group, etc.), an oxy group (—O—), a thio group (—S—), a phosphinidene group (—PR—) (for example, a phenylphosphinidene group, etc.), a silylene group (—SiRR'—) (for example, a dimethylsilylene group, a diphenylsilylene group, etc.) and a combination thereof. Each of these linking groups may further have a substituent.

As the substituent represented by each of $R^{41}$, $R^{42}$, $R^{43}$ and $R^{44}$, an alkyl group, an aryl group and a heterocyclic group are preferable; an aryl group and a heterocyclic group are more preferable; and an aryl group is especially preferable.

The linking group represented by $Y^{41}$ is preferably a vinyl group substituted at the 1- and 2-positions, a phenylene ring, a pyridine ring, a pyrazine ring, a pyrimidine ring or an alkylene group having from 1 to 8 carbon atoms; more preferably a vinyl group substituted at the 1- and 2-positions, a phenylene ring or an alkylene group having from 1 to 6 carbon atoms; and especially preferably a phenylene ring.

The substituent represented by each of $R^{43}$ and $R^{44}$ may be linked to the linking group represented by $Y^{41}$ to form a ring. For example, in the case of a phenylene ring in which $Y^{41}$ is linked at the 1- and 2-positions, $R^{43}$ and $R^{44}$ may be linked at the 3- and 6-positions, respectively to form a 1,10-phenanthroline ring, which may further have a substituent.

One of complexes which are more preferable as the platinum complex (phosphorescent) material having a tetradentate ligand is a Pt complex represented by the following formula (B).

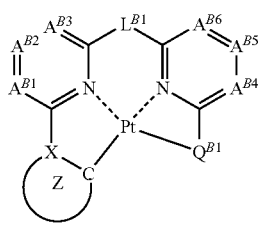

Formula (B)

In the formula (B), each of $A^{B1}$ and $A^{B6}$ independently represents C—R or N. R represents a hydrogen atom or a substituent. $L^{B1}$ represents a single bond or a divalent linking group. X represents C or N. Z represents a 5-membered or 6-membered aromatic ring or aromatic heterocyclic ring which is formed together with X—C in the formula. $Q^{B1}$ represents an anionic group which is bound to Pt.

The formula (B) is described.

Each of $A^{B1}$ to $A^{B6}$ independently represents C—R or N. R represents a hydrogen atom or a substituent. The substituent represented by R is synonymous with that exemplified previously as the group A of substituent, and a preferred range is also the same.

Each of $A^{B1}$ to $A^{B6}$ is preferably C—R, and Rs may be linked to each other to form a ring. In the case where each of $A^{B1}$ to $A^{B6}$ is C—R, R in each of $A^{B2}$ and $A^{B5}$ is preferably a hydrogen atom, an alkyl group, an aryl group, an amino group, an alkoxy group, an aryloxy group, a fluorine group or a cyano group, more preferably a hydrogen atom, an amino group, an alkoxy group, an aryloxy group or a fluorine group, and especially preferably a hydrogen atom or a fluorine group; and R in each of $A^{B1}$, $A^{B3}$, $A^{B4}$ and $A^{B6}$ is a hydrogen atom, an alkyl group, an aryl group, an amino group, an alkoxy group, an aryloxy group, a fluorine group or a cyano group, more preferably a hydrogen atom, an amino group, an alkoxy group, an aryloxy group or a fluorine group, and especially preferably a hydrogen atom.

$L^{B1}$ represents a single bond or a divalent linking group.

Examples of the divalent linking group represented by $L^{B1}$ include an alkylene group (for example, methylene, ethylene, propylene, etc.), an arylene group (for example, phenylene, naphthalenediyl, etc.), a heteroarylene group (for example, pyridinediyl, thiophenediyl, etc.), an imino group (—NR—) (for example, a phenylimino group, etc.), an oxy group (—O—), a thio group (—S—), a phosphinidene group (—PR—) (for example, a phenylphosphinidene group, etc.), a silylene group (—SiRR'—) (for example, a dimethylsilylene group, a diphenylsilylene group, etc.) and a combination thereof. Each of these linking groups may further have a substituent.

$L^{B1}$ is preferably a single bond, an alkylene group, an arylene group, a heteroarylene group, an imino group, an oxy group, a thio group or a silylene group; more preferably a single bond, an alkylene group, an arylene group or an imino group; further more preferably an alkylene group; still further more preferably a methylene group; even further more preferably a disubstituted methylene group; even still further more preferably a dimethylmethylene group, a diethylmethylene group, a diisobutylmethylene group, a dibenzylmethylene group, an ethylmethylmethylene group, a methylpropylmethylene group, an isobutylmethylmethylene group, a diphenylmethylene group, a methylphenylmethylene group, a cyclohexanediyl group, a cyclopentanediyl group, a fluorenediyl group or a fluoromethylmethylene group; and especially preferably a dimethylmethylene group, a diphenylmethylene group or a cyclohexanediyl group.

X represents C or N. Z represents a 5-membered or 6-membered aromatic hydrocarbon ring or aromatic heterocyclic ring formed together with X—C in the formula. Examples of the aromatic hydrocarbon ring or aromatic heterocyclic ring represented by Z include a benzene ring, a naphthalene ring, an anthracene ring, a pyrene ring, a phenanthrene ring, a perylene ring, a pyridine ring, a quinoline ring, an isoquinoline ring, a phenanthridine ring, a pyrimidine ring, a pyrazine ring, a pyridazine ring, a triazine ring, a cinnoline ring, an acridine ring, a phthalazine ring, a quinazoline ring, a quinoxaline ring, a naphthyridine ring, a pteridine ring, a pyrrole ring, a pyrazole ring, a triazole ring, an indole ring, a carbazole ring, an indazole ring, a benzimidazole ring, an oxazole ring, a thiazole ring, an oxadiazole ring, a thiadiazole ring, a benzoxazole ring, a benzothiazole ring, an imidazopyridine ring, a thiophene ring, a benzothiophene ring, a furan ring, a benzofuran ring, a phosphole ring, a phosphinine ring and a silole ring. Z may have a substituent. As the substituent, those which are exemplified previously as the group A of substituent are applicable. Also, Z may form a condensed ring together with other ring.

Z is preferably a benzene ring, a naphthalene ring, a pyrazole ring, an imidazole ring, a triazole ring, a pyridine ring, an indole ring or a thiophene ring, and more preferably a benzene ring, a pyrazole ring or a pyridine ring.

$Q^{B1}$ represents an anionic group which is bound to Pt. Examples of the anionic group represented by $Q^{B1}$ include a vinyl ligand, an aromatic hydrocarbon ring ligand (for example, a benzene ligand, a naphthalene ligand, an anthracene ligand, a phenanthracene ligand, etc.) and a heterocyclic ligand (for example, a furan ligand, a thiophene ligand, a pyridine ligand, a pyrazine ligand, a pyrimidine ligand, a pyridazine ligand, a triazine ligand, a thiazole ligand, an oxazole ligand, a pyrrole ligand, an imidazole ligand, a pyrazole ligand, a triazole ligand and a condensed ring ligand containing the foregoing ligand (for example, a quinoline ligand, a benzothiazole ligand, etc.), etc.). Herein, the bond between $Q^{B1}$ and Pt may be any of a covalent bond, an ionic bond or a coordinate bond. The atom bound to Pt in $Q^{B1}$ is preferably a carbon atom, a nitrogen atom, an oxygen atom, a sulfur atom or a phosphorus atom, more preferably a carbon atom, an oxygen atom or a nitrogen atom, and further more preferably a carbon atom.

The group represented by $Q^{B1}$ is preferably an aromatic hydrocarbon ring ligand which is bound to Pt via its carbon atom, an aromatic heterocyclic ligand which is bound to Pt via its carbon atom, a nitrogen-containing aromatic heterocyclic ligand which is bound to Pt via its nitrogen atom or an acyloxy ligand; and more preferably an aromatic hydrocarbon ring ligand which is bound to Pt via its carbon atom or an aromatic heterocyclic ligand which is bound to Pt via its carbon atom. It is especially preferable that the group represented by $Q^{B1}$ is the same group as that in the ring Z formed together with C—X in the formula (B).

The Pt complex represented by the formula (B) is more preferably a Pt complex represented by the following formula (C).

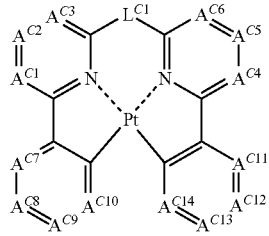

Formula (C)

In the formula (C), each of $A^{C1}$ to $A^{C14}$ independently represents C—R or N. R represents a hydrogen atom or a substituent. $L^{C1}$ represents a single bond or a divalent linking group.

The formula (C) is described.

Each of $A^{C1}$ to $A^{C14}$ independently represents C—R or N. R represents a hydrogen atom or a substituent. $A^{C1}$ to $A^{C6}$ are respectively synonymous with $A^{B1}$ to $A^{B6}$ in the foregoing formula (B), and preferred ranges thereof are also the same.

As to $A^{C7}$ to $A^{C14}$, a number of Ns (nitrogen atoms) in each of $A^{C7}$ to $A^{C10}$ and $A^{C11}$ to $A^{C14}$ is preferably from 0 to 2, and more preferably from 0 or 1. The ring constituent N is chosen preferably among $A^{C8}$ to $A^{C10}$ and $A^{C12}$ to $A^{C14}$, more preferably among $A^{C8}$, $A^{C9}$, $A^{C12}$ and $A^{C13}$, and especially preferably from $A^{C8}$ or $A^{C12}$.

When each of $A^{C7}$ to $A^{C14}$ represents C—R, R of each of $A^{C8}$ and $A^{C12}$ is preferably a hydrogen atom, an alkyl group, a polyfluoroalkyl group, an aryl group, an amino group, an alkoxy group, an aryloxy group, a fluorine group or a cyano group, more preferably a hydrogen atom, a polyfluoroalkyl group, an alkyl group, an aryl group, a fluorine group or a cyano group, and especially preferably a hydrogen atom, a polyfluoroalkyl group or a cyano group. R of each of $A^{C7}$, $A^{C9}$, $A^{C11}$ and $A^{C13}$ is preferably a hydrogen atom, an alkyl group, a polyfluoroalkyl group, an aryl group, an amino group, an alkoxy group, an aryloxy group, a fluorine group or a cyano group, more preferably a hydrogen atom, a polyfluoroalkyl group, a fluorine group or a cyano group, and especially preferably a hydrogen atom or a fluorine group. R of each of $A^{C10}$ and $A^{C14}$ is preferably a hydrogen atom or a fluorine group, and more preferably a hydrogen atom. When any one of $A^{C7}$ to $A^{C9}$ or $A^{C11}$ to $A^{C13}$ represents C—R, Rs may be linked to each other to form a ring.

The linking group represented by $L^{C1}$ is synonymous with the liking group represented by $L^{B1}$ in the foregoing formula (B), and a preferred range thereof is also the same.

The Pt complex represented by the formula (B) is further more preferably a Pt complex represented by the following formula (D).

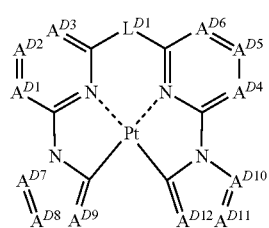

Formula (D)

In the formula (D), each of $A^{D1}$ to $A^{D12}$ independently represents C—R or N. R represents a hydrogen atom or a substituent. $L^{D1}$ represents a single bond or a divalent linking group.

The formula (D) is described.

Each of $A^{D1}$ to $A^{D12}$ independently represents C—R or N. R represents a hydrogen atom or a substituent.

$A^{D1}$ to $A^{D6}$ are respectively synonymous with $A^{B1}$ to $A^{B6}$ in the foregoing formula (B), and preferred ranges thereof are also the same.

As to $A^{D7}$ to $A^{D12}$, a number of Ns (nitrogen atoms) in each of $A^{D7}$ to $A^{D9}$ and $A^{D10}$ to $A^{D12}$ is preferably from 0 to 2, more preferably from 0 or 1, and especially preferably 1. The ring constituent N is chosen preferably among $A^{D7}$ to $A^{D9}$ and $A^{D10}$ to $A^{D12}$, more preferably among $A^{D7}$, $A^{D9}$, $A^{D10}$ and $A^{D12}$, and especially preferably from $A^{D7}$ or $A^{D10}$.

When each of $A^{D7}$ to $A^{D12}$ represents C—R, R of each of $A^{D8}$ and $A^{D11}$ is preferably a hydrogen atom, an alkyl group, a polyfluoroalkyl group, an aryl group, an amino group, an alkoxy group, an aryloxy group, a fluorine group or a cyano group, more preferably a hydrogen atom, a polyfluoroalkyl group, an alkyl group, an aryl group, a fluorine group or a cyano group, and especially preferably a polyfluoroalkyl group (for example, a trifluoromethyl group, a perfluoroethyl group, etc.) or a cyano group. R of each of $A^{D7}$, $A^{D9}$, $A^{D10}$ and $A^{D12}$ is preferably a hydrogen atom, an alkyl group, a polyfluoroalkyl group, an aryl group, an amino group, an alkoxy group, an aryloxy group, a fluorine group or a cyano group, and more preferably a hydrogen atom or a fluorine group. When any one of $A^{D7}$ to $A^{D12}$ represents C—R, Rs may be linked to each other to form a ring.

The linking group represented by $L^{D1}$ is synonymous with the linking group represented by $L^{B1}$ in the foregoing formula (B), and a preferred range thereof is also the same.

One of complexes which are more preferable as the platinum complex (phosphorescent) material having a tetradentate ligand is a Pt complex represented by the following formula (E).

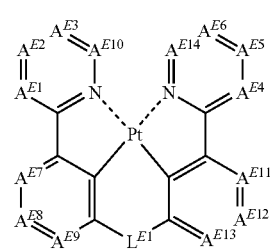

Formula (E)

In the formula (E), each of $A^{E1}$ to $A^{E14}$ independently represents C—R or N. R represents a hydrogen atom or a substituent. $L^{E1}$ represents a single bond or a divalent linking group.

The formula (E) is described. Each of $A^{E1}$ to $A^{E14}$ independently represents C—R or N. R represents a hydrogen atom or a substituent. $A^{E1}$ to $A^{E6}$ are respectively synonymous with $A^{B1}$ to $A^{B6}$ in the foregoing formula (B), and preferred ranges thereof are also the same. $A^{E7}$ to $A^{E14}$ are respectively synonymous with $A^{C7}$ to $A^{C14}$ in the foregoing formula (C), and preferred ranges thereof are also the same.

The linking group represented by $L^{E1}$ is synonymous with the linking group represented by $L^{B1}$ in the foregoing formula (B), and a preferred range thereof is also the same.

$L^{E1}$ is preferably a single bond, an alkylene group, an arylene group, a heteroarylene group, an imino group, an oxy group, a thio group or a silylene group; more preferably an alkylene group, an imino group, an oxy group, a thio group or a silylene group; further more preferably an alkylene group; even further more preferably a methylene group; even further more preferably a disubstituted methylene group; even still further more preferably a dimethylmethylene group, a diethylmethylene group, a diisobutylmethylene group, a dibenzylmethylene group, an ethylmethylmethylene group, a methylpropylmethylene group, an isobutylmethylmethylene group, a diphenylmethylene group, a methylphenylmethylene group, a cyclohexanediyl group, a cyclopentanediyl group, a fluorenediyl group or a fluoromethylmethylene group; and especially preferably a dimethylmethylene group, a diphenylmethylene group or a cyclohexanediyl group.

One of complexes which are more preferable as the platinum complex (phosphorescent) material having a tetradentate ligand is a Pt complex represented by the following formula (F).

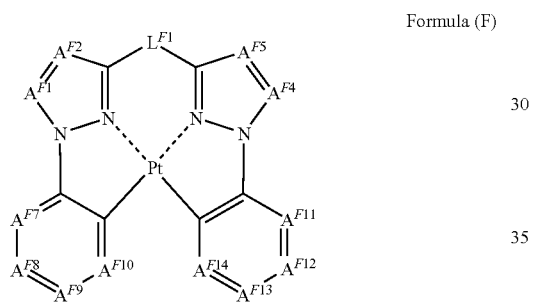

Formula (F)

In the formula (F), each of $A^{F1}$ to $A^{F14}$ independently represents C—R or N. R represents a hydrogen atom or a substituent. $L^{F1}$ represents a single bond or a divalent linking group.

The formula (F) is described.

Each of $A^{F1}$ to $A^{F14}$ independently represents C—R or N. R represents a hydrogen atom or a substituent. $A^{F1}$ to $A^{F5}$ are respectively synonymous with $A^{B1}$ to $A^{B5}$ in the foregoing formula (B). Each of $A^{F1}$ to $A^{F5}$ is preferably C—R, and Rs may be linked to each other to form a ring. When each of $A^{F1}$ to $A^{F5}$ is C—R, R of each of $A^{F1}$ to $A^{F5}$ is preferably a hydrogen atom, an alkyl group, an aryl group, an amino group, an alkoxy group, an aryloxy group, a fluorine group or a cyano group, more preferably a hydrogen atom, an aryl group, a fluorine group or a cyano group, and especially preferably a hydrogen atom.

$A^{F7}$ to $A^{F14}$ are respectively synonymous with $A^{C7}$ to $A^{C14}$ in the foregoing formula (C), and preferred ranges thereof are also the same. In particular, when any one of $A^{F7}$ to $A^{F9}$ or $A^{F11}$ to $A^{F13}$ represents C—R, Rs may be linked to each other to form a ring. The ring structure formed when Rs are linked to each other is preferably a furan ring, a benzofuran ring, a pyrrole ring, a benzopyrrole ring, a thiophene ring, a benzothiophene ring or a fluorene ring. Each of these rings may further have a substituent.

The linking group represented by $L^{F1}$ is synonymous with the linking group represented by $L^{B1}$ in the foregoing formula (B), and a preferred range thereof is also the same.

Specific examples of the light emitting material are given below, but it should not be construed that the invention is limited thereto.

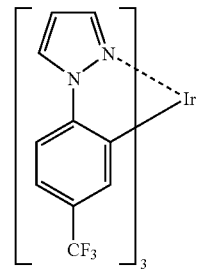

D-1

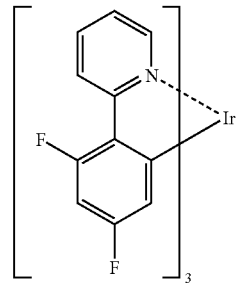

D-2

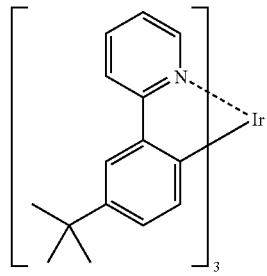

D-3

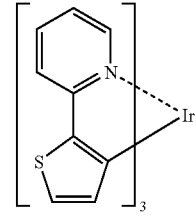

D-4

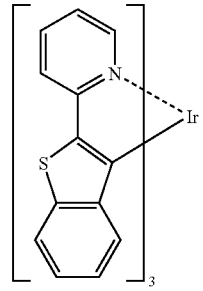

D-5

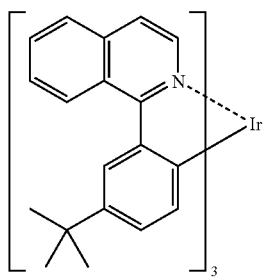 D-6
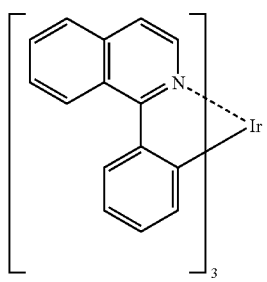 D-7
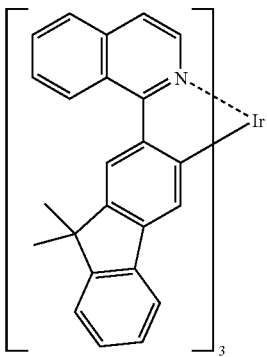 D-8
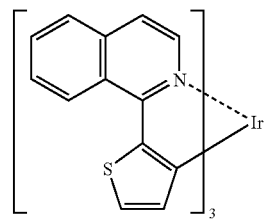 D9
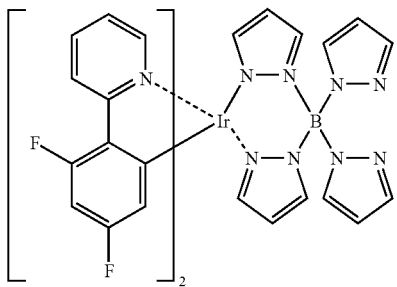 D-10
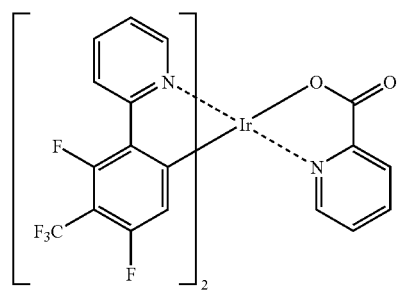 D-11
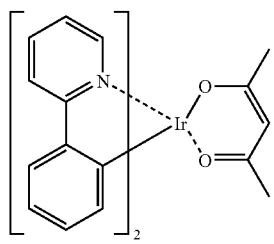 D-12
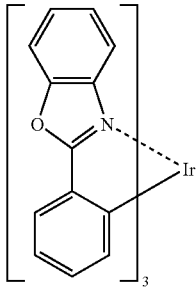 D-13
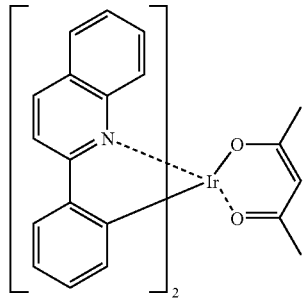 D-14
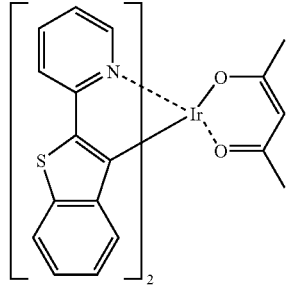 D-15

D-16
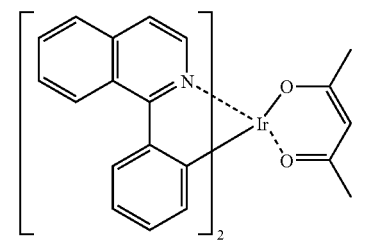
D-17
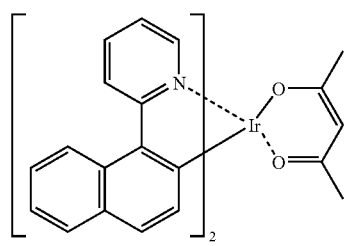
D-18
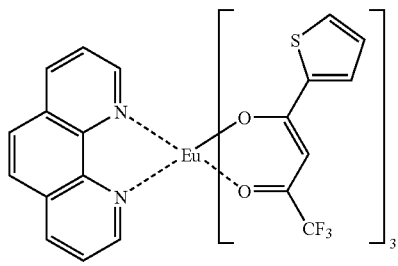
D-19
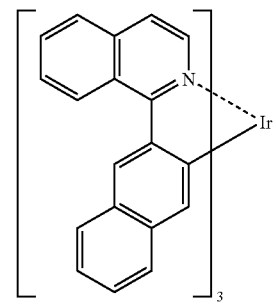
D-20
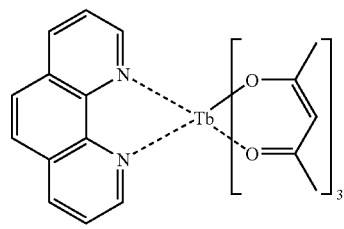
D-21
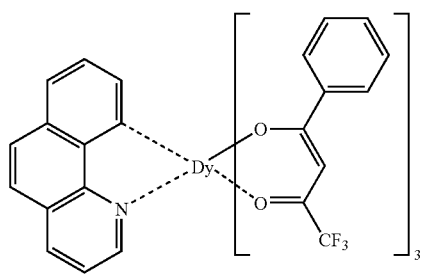
D-22
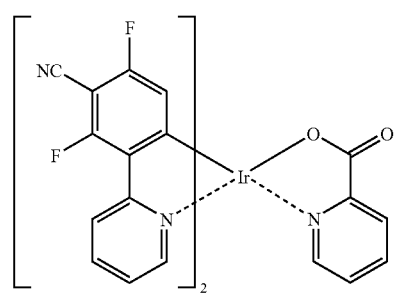
D-23
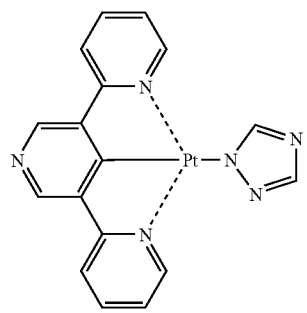
D-24
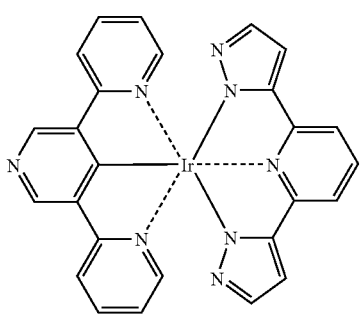
D-25
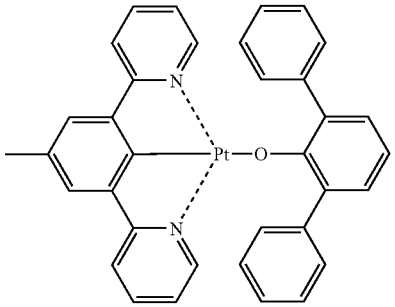
D-26
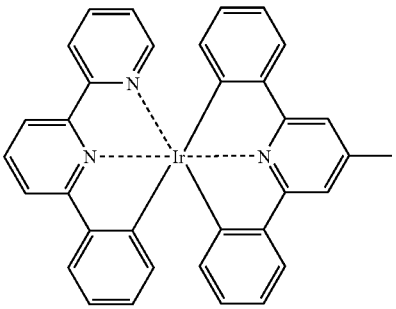

-continued
D-27
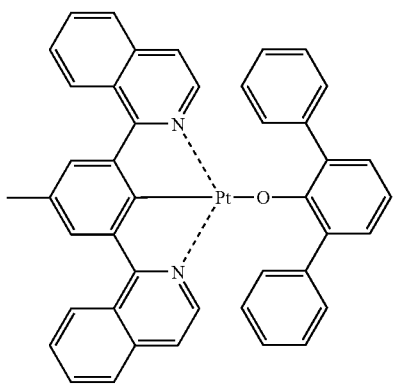
D-28
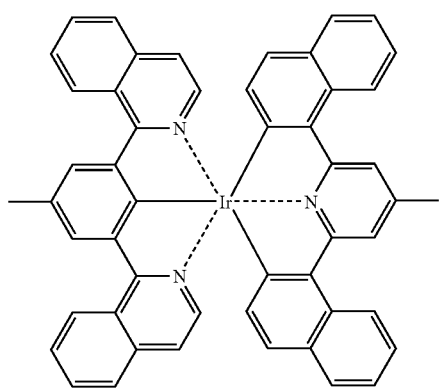
D-29
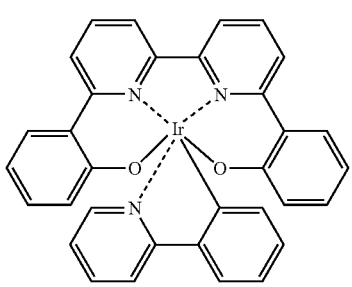
D-30
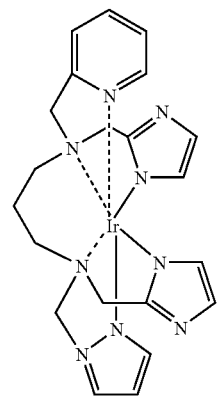
-continued
D-31
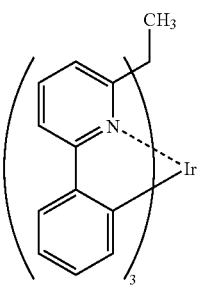
D-32
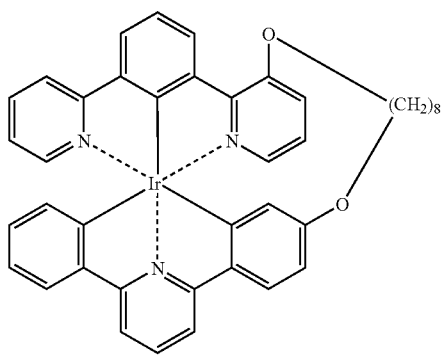
D-33
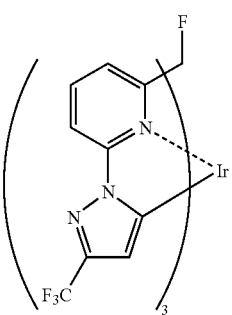
D-34
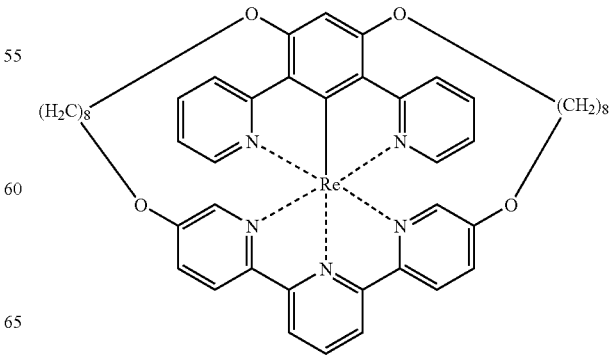

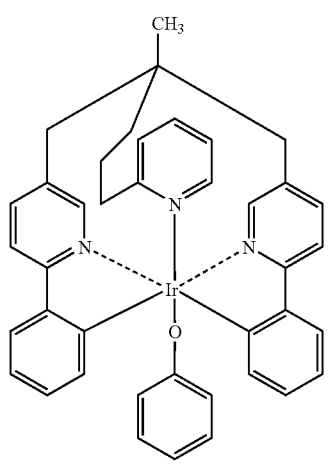
D-35
Also, examples of the platinum complex phosphorescent material having a tetradentate ligand are given below, but it should not be construed that the invention is limited thereto.
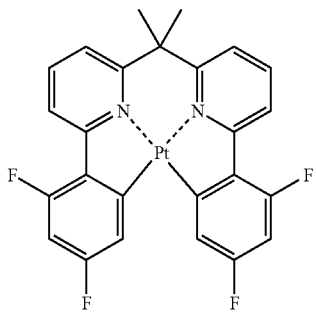
2-2
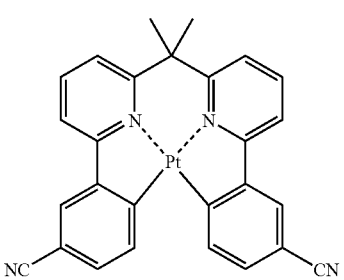
2-3
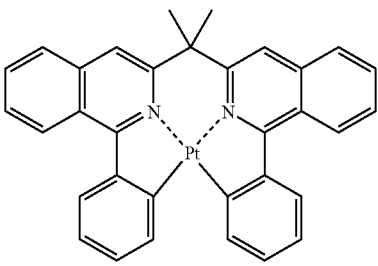
2-4
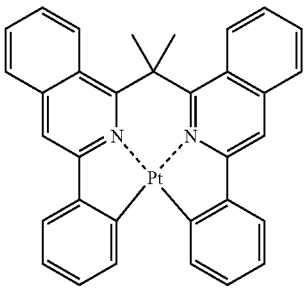
2-5
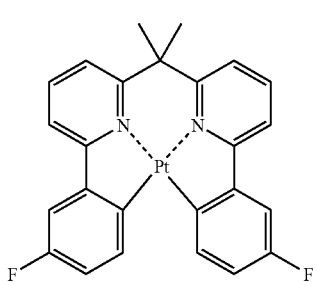
2-6

-continued
2-7
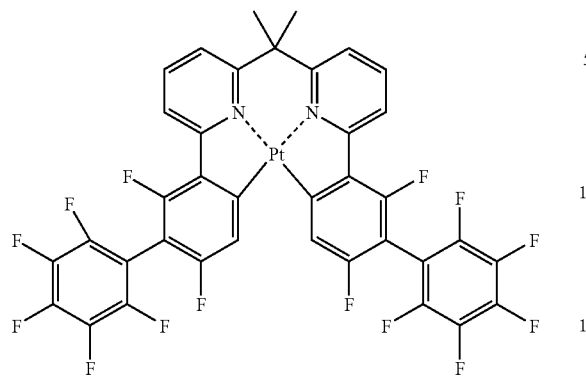
2-8
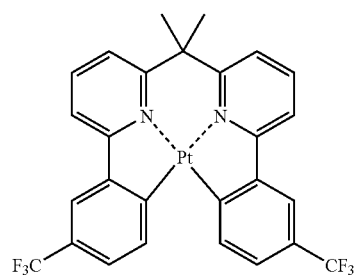
2-9
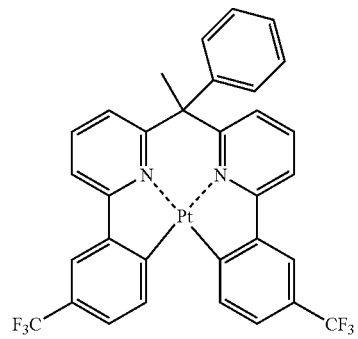
2-10
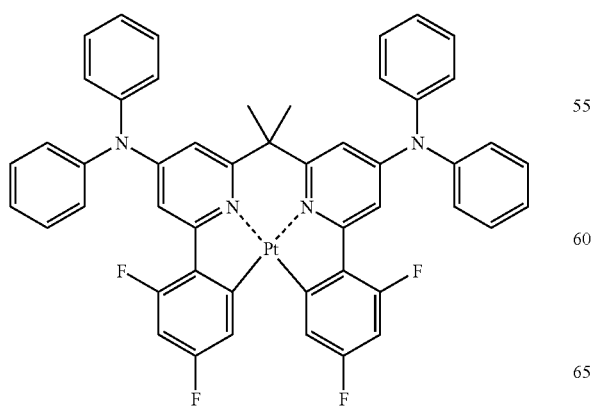
-continued
2-11
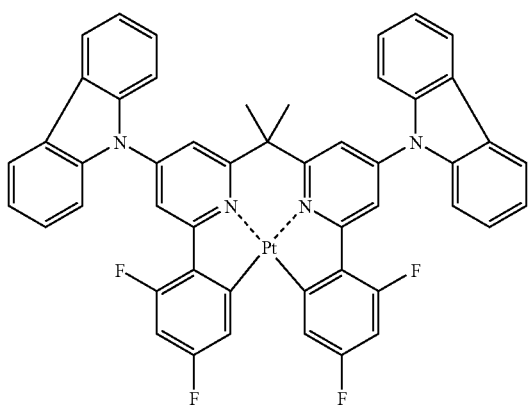
2-12
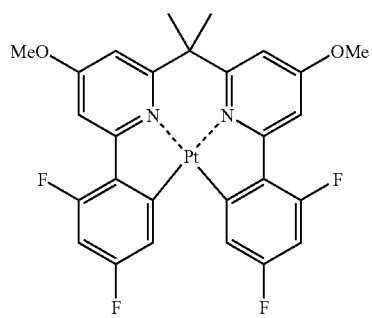
2-13
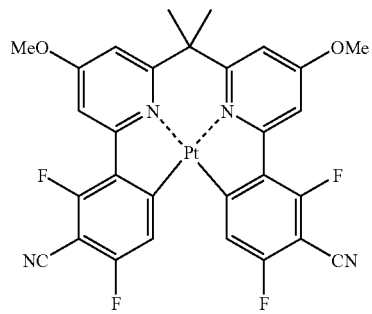
3-1
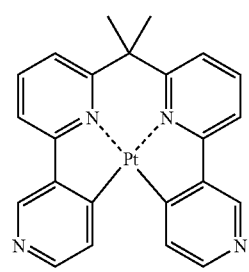
3-2
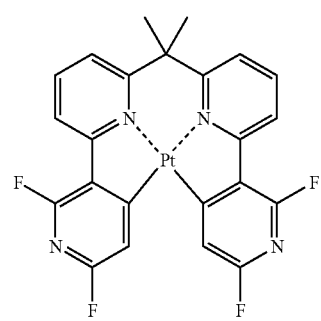

-continued
3-3
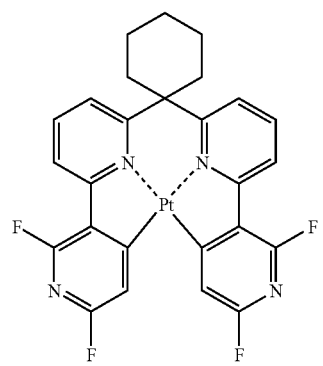
3-4
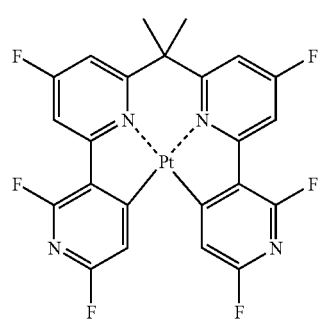
3-5
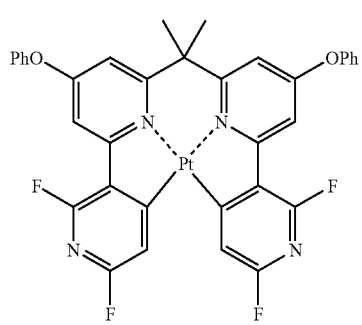
4-1
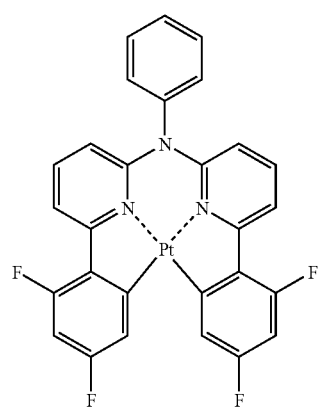
-continued
4-2
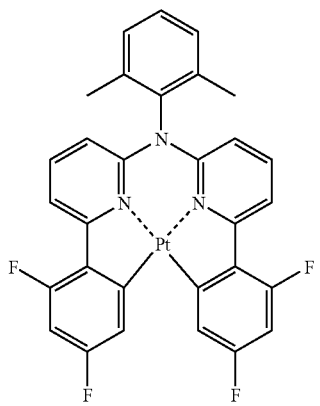
4-3
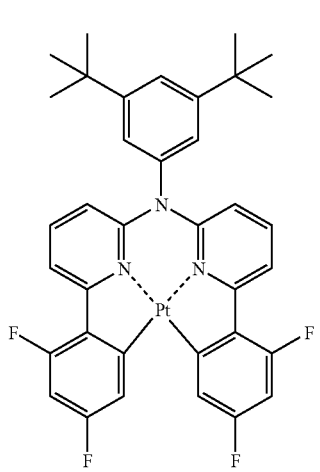
4-4
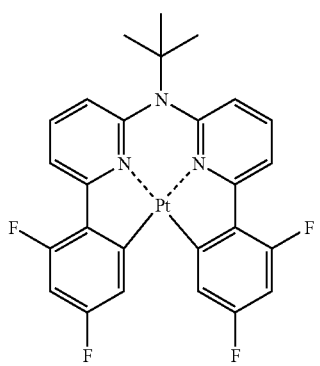
4-5
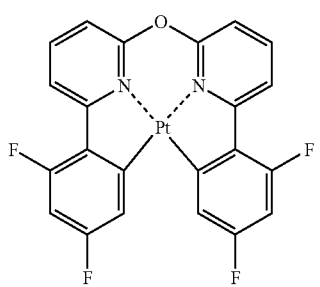

-continued
5-1
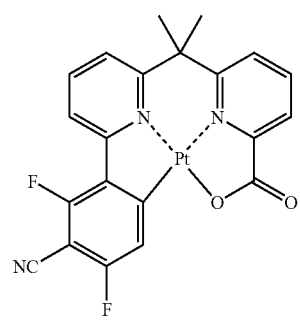
5-2
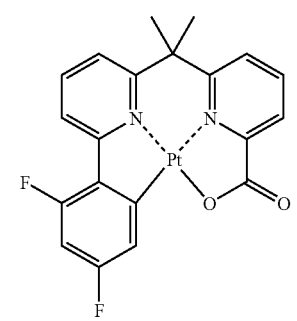
5-3
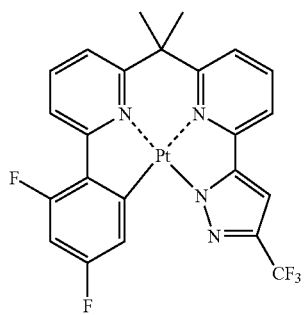
5-4
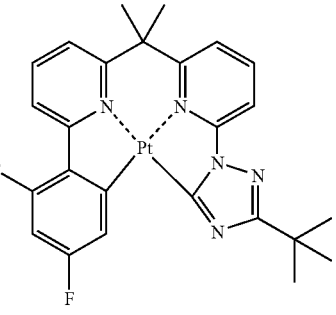
6-1
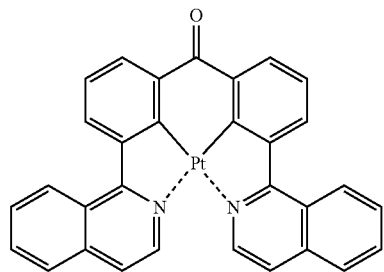
-continued
6-2
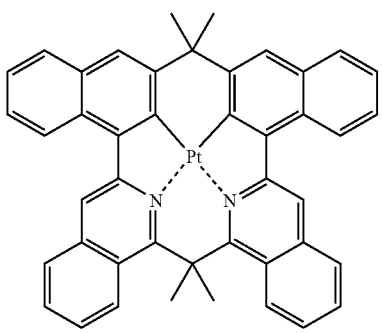
6-3
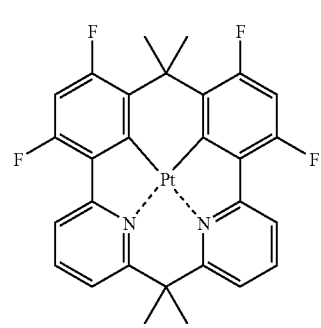
6-4
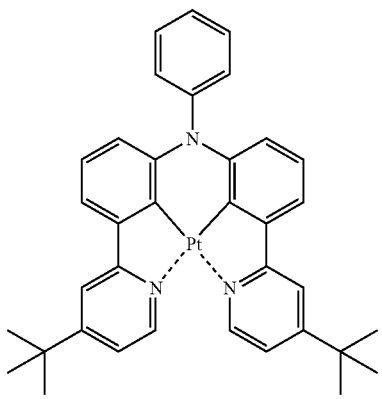
6-5
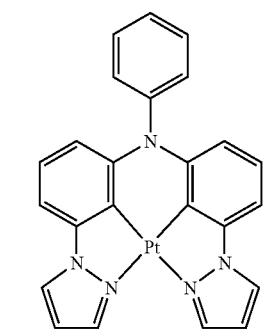

-continued
7-1 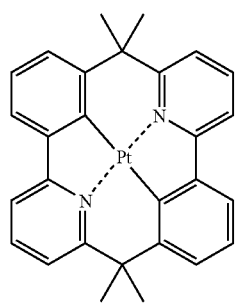
7-2 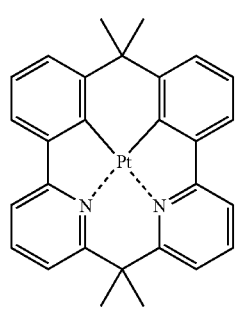
7-3 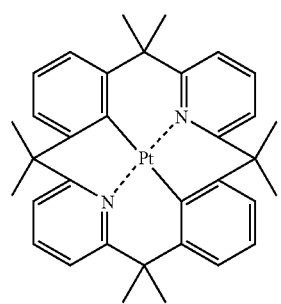
7-4 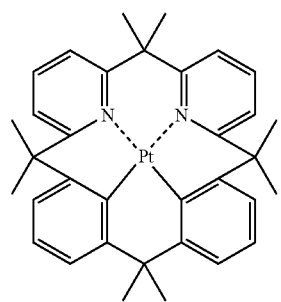
7-5 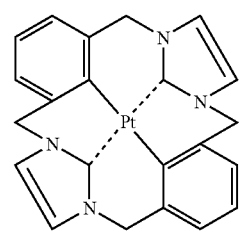
-continued
8-1 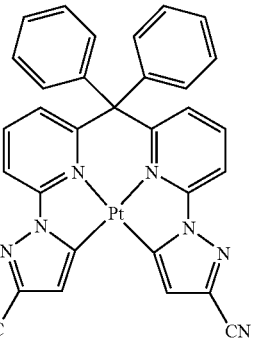
8-2 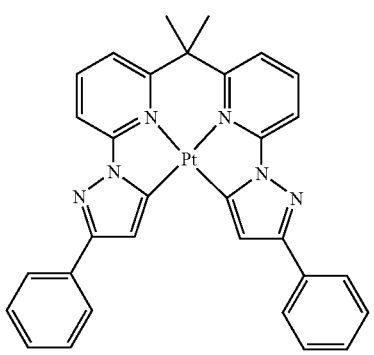
8-3 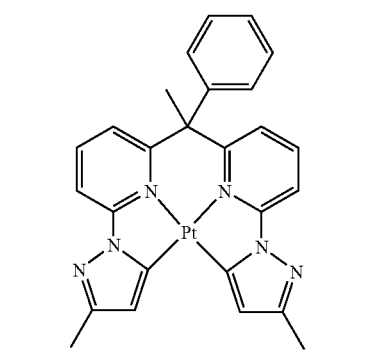
8-4 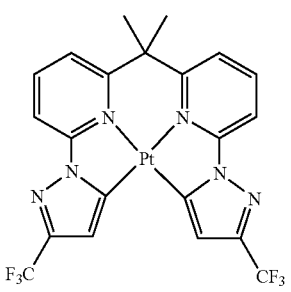
8-5 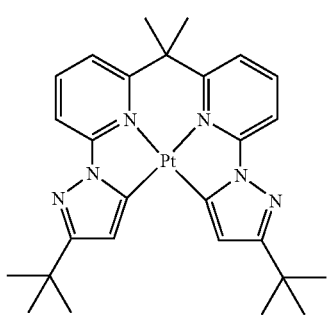

8-6 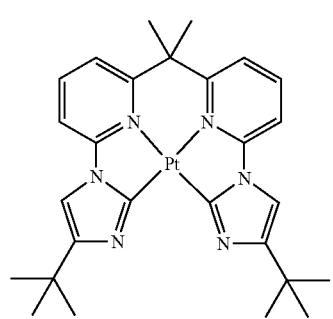
8-7 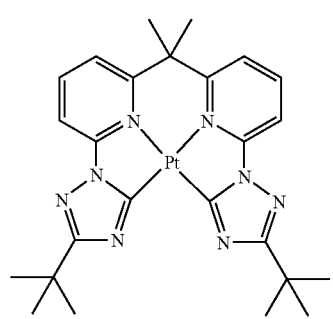
8-8 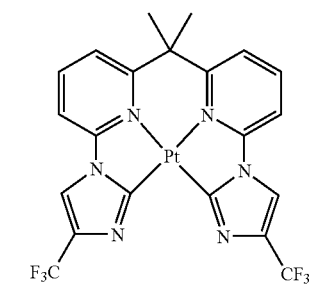
8-9 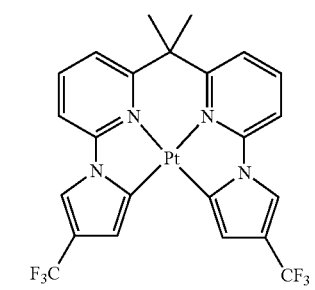
8-10 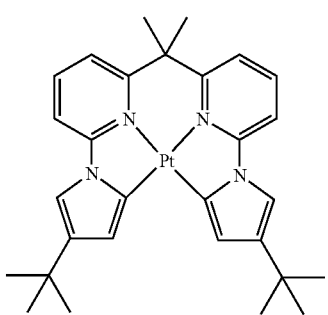
9-1 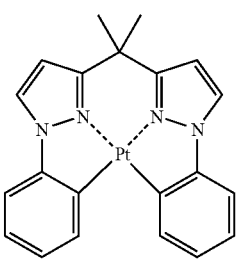
9-2 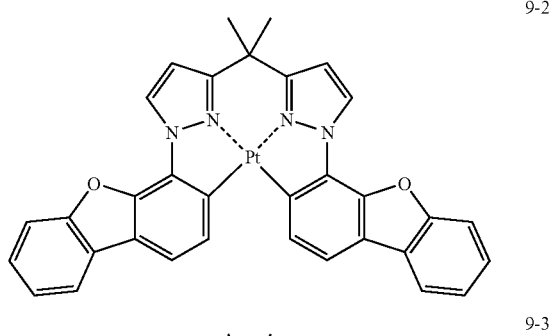
9-3 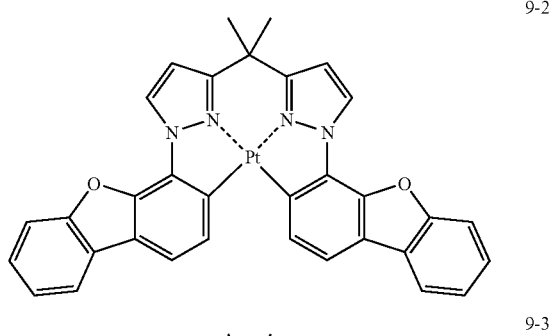
9-4 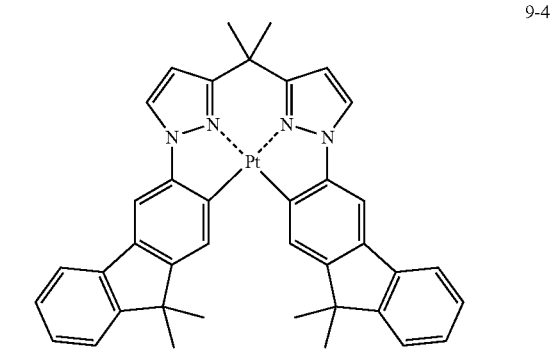
9-5 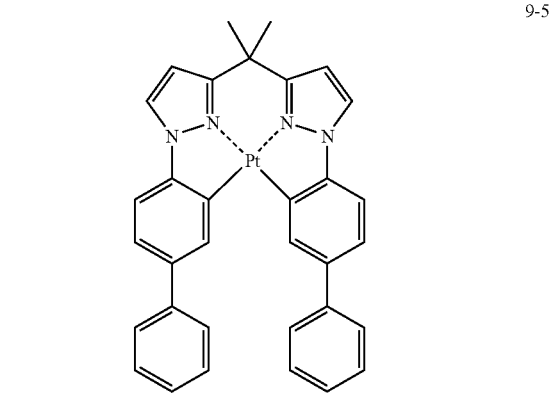

9-6
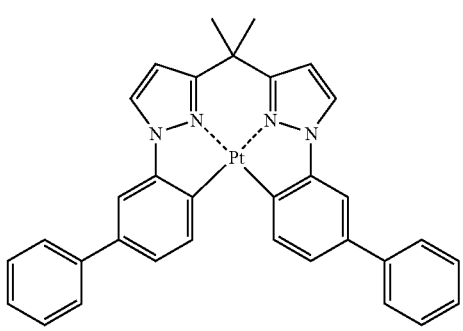

9-7
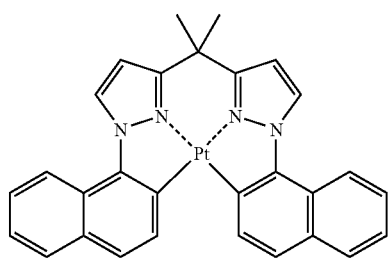

9-8
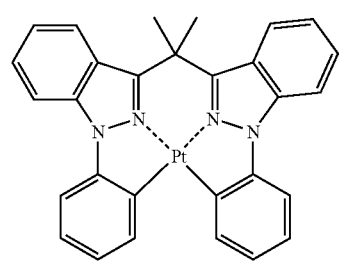

9-9
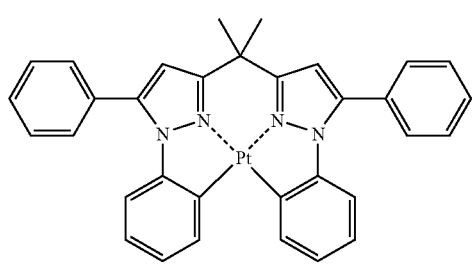

9-10
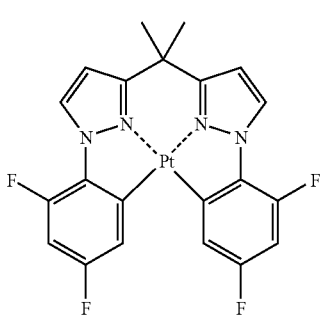

9-11
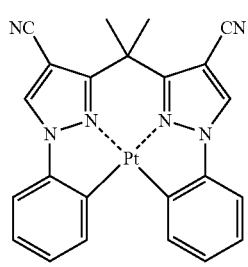

9-12
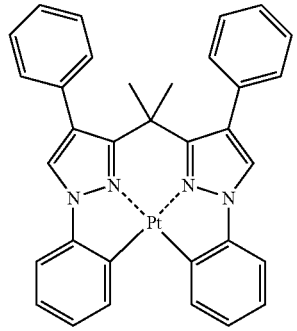

9-13
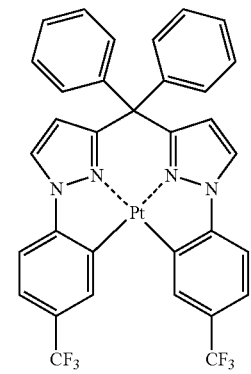

9-14
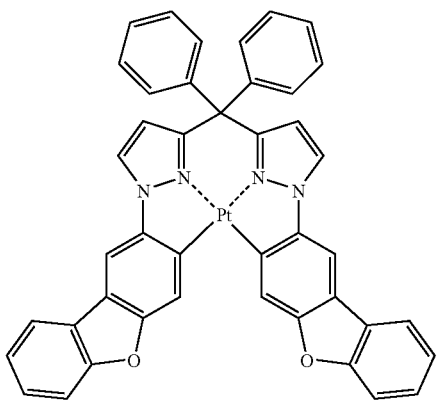

The light emitting material is generally contained in an amount of from 0.1% by mass to 50% by mass relative to the mass of all the compounds capable for forming the light emitting layer. From the viewpoints of durability and external quantum efficiency, a content of the light emitting material is preferably from 1% by mass to 50% by mass, and more preferably from 2% by mass to 40% by mass.

<<Host Material>>

Examples of the host material which is contained in the light emitting layer include, in addition to the compound of the invention, a material having a carbazole skeleton, a material having an azacarbazole skeleton, a material having an indole skeleton, a material having an azaindole skeleton, a material having a diarylamine skeleton, a material having a pyridine skeleton, a material having a pyrazine skeleton, a material having a triazine skeleton, a material having an arylsilane skeleton and materials exemplified in the sections of a hole injection layer, a hole transport layer, an electron injection layer and an electron transport layer as described later.

Though a content of the host material is not particularly limited, it is preferably from 50 to 99% by mass, more preferably from 70 to 95% by mass, and especially preferably from 85 to 90% by mass relative to the whole mass of the materials to be contained in the light emitting layer.

The thickness of the light emitting layer is not particularly limited. In general, the thickness of the light emitting layer is preferably from 1 nm to 500 nm, more preferably from 5 nm to 200 nm, and further preferably from 10 nm to 100 nm.

—Hole Injection Layer and Hole Transport Layer—

Each of the hole injection layer and the hole transport layer is a layer having a function to accept a hole from the anode or the anode side to transport it into the cathode side. Specifically, each of the hole injection layer and the hole transport layer is preferably a layer containing, in addition to the compound of the invention, a carbazole derivative, an azacarbazole derivative, an indole derivative, an azaindole derivative, a triazole derivative, an oxazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic dimethylidine based compound, a porphyrin based compound, an organic silane derivative, carbon or the like.

The thickness of each of the hole injection layer and the hole transport layer is preferably not more than 500 nm from the viewpoint of lowering the driving voltage.

The thickness of the hole transport layer is preferably from 1 nm to 500 nm, more preferably from 5 nm to 200 nm, and further preferably from 10 nm to 100 nm. Also, the thickness of the hole injection layer is preferably from 0.1 nm to 200 nm, more preferably from 0.5 nm to 100 nm, and further preferably from 1 nm to 100 nm.

Each of the hole injection layer and the hole transport layer may be of a single layer structure composed of one or two or more kinds of the foregoing materials or may be of a multi-layer structure composed of a plurality of layers of the same or different compositions.

—Electron Injection Layer and Electron Transport Layer—

Each of the electron injection layer and the electron transport layer is a layer having a function to accept an electron from the cathode or the cathode side and to transport it into the anode side. Specifically, each of the electron injection layer and the electron transport layer is preferably a layer containing, in addition to the compounds of the present invention, a triazole derivative, an oxazole derivative, an oxadiazole derivative, an imidazole derivative, a fluorenone derivative, an anthraquinodimethane derivative, an anthrone derivative, a diphenylquinone derivative, a thiopyrandioxide derivative, a carbodiimide derivative, a fluorenylidenemethane derivative, a distyrylpyrazine derivative, an aromatic tetracarboxylic acid anhydride of naphthalene, perylene, etc., a phthalocyanine derivative, a metal complex of every sort represented by metal complexes of an 8-quinolinol derivative and metal complexes containing, as a ligand, metal phthalocyanine, benzoxazole or benzothiazole, an organic silane derivative, or the like.

The thickness of each of the electron injection layer and the electron transport layer is preferably not more than 500 nm from the viewpoint of lowering the driving voltage.

The thickness of the electron transport layer is preferably from 1 nm to 500 nm, more preferably from 5 nm to 200 nm, and further preferably from 10 nm to 100 nm. Also, the thickness of the electron injection layer is preferably from 0.1 nm to 200 nm, more preferably from 0.2 nm to 100 nm, and further preferably from 0.5 nm to 50 nm.

Each of the electron injection layer and the electron transport layer may be of a single layer structure composed of one or two or more kinds of the foregoing materials or may be of a multilayer structure composed of a plurality of layers of the same or different compositions.

—Hole Blocking Layer—

The hole blocking layer is a layer having a function to prevent permeation of the hole having been transported from the anode side to the light emitting layer into the cathode side. In the invention, the hole blocking layer can be provided as an organic compound layer adjacent to the light emitting layer on the cathode side.

Examples of the organic compound constituting the hole blocking layer include, in addition to the compound of the invention, aluminum complexes such as BAlq, triazole derivatives and phenanthroline derivatives such as BCP.

The thickness of the hole blocking layer is preferably from 1 nm to 500 nm, more preferably from 5 nm to 200 nm, and further preferably from 10 nm to 100 nm.

The hole blocking layer may be of a single layer structure composed of one or two or more kinds of the foregoing materials or may be of a multilayer structure composed of a plurality of layers of the same or different compositions.

—Electron Blocking Layer—

The electron blocking layer is a layer having a function of preventing passage of an electron, which has been transported to the light emitting layer from the cathode side, to the anode side. In the invention, the electron blocking layer may be provided as an organic layer adjacent to the light emitting layer on the anode side.

Examples of the compound constituting the electron blocking layer include those exemplified previously as the hole transporting material.

A thickness of the electron blocking layer is preferably from 1 nm to 500 nm, more preferably from 5 nm to 200 nm, and further more preferably from 10 nm to 100 nm.

The electron blocking layer may be of a single-layered structure composed of one or two or more kinds of the foregoing materials or a multilayered structure composed of a plurality of layers having the same composition or a different composition from each other.

<Protective Layer>

The whole of the organic EL device may be protected by a protective layer.

As a material to be contained in the protective layer, any material having a function to inhibit the incorporation of a substance promoting the deterioration of the device, such as moisture and oxygen, into the device is useful.

Specific examples thereof include metals (for example, In, Sn, Pb, Au, Cu, Ag, Al, Ti, Ni, etc.), metal oxides (for example, MgO, SiO, $SiO_2$, $Al_2O_3$, GeO, NiO, CaO, BaO, $Fe_2O_3$, $Y_2O_3$, $TiO_2$, etc.), metal nitrides (for example, $SiN_x$, $SiN_xO_y$, etc.), metal fluorides (for example, $MgF_2$, LiF, $AlF_3$, $CaF_2$, etc.), polyethylene, polypropylene, polymethyl methacrylate, polyimides, polyureas, polytetrafluoroethylene, polychlorotrifluoroethylene, polydichlorodifluoroethylene, copolymers of chlorotrifluoroethylene and dichlorodifluoroethylene, copolymers obtained by copolymerizing a monomer mixture containing tetrafluoroethylene and at least one comonomer, fluorine-containing copolymers having a cyclic structure in a copolymer main chain thereof, water-absorbing substances having a water absorption factor of 1% or more and moisture-proof substances having a water absorption factor of not more than 0.1%.

A method for forming the protective layer is not particularly limited. For example, a vacuum vapor deposition process, a sputtering process, a reactive sputtering process, an MBE (molecular beam epitaxy) process, a cluster ion beam process, an ion plating process, a plasma polymerization process (high-frequency exciting ion plating process), a plasma CVD process, a laser CVD process, a thermal CVD process, a gas source CVD process, a coating process, a printing process and a transfer process can be adopted.

<Sealing Vessel>

Further, the organic EL device of the invention may be prepared by sealing the whole of the device using a sealing vessel. In addition, a moisture absorber or an inert liquid may be charged in a space between the sealing vessel and the organic EL device. Though the moisture absorber is not particularly limited, examples thereof include barium oxide, sodium oxide, potassium oxide, calcium oxide, sodium sulfate, calcium sulfate, magnesium sulfate, phosphorus pentoxide, calcium chloride, magnesium chloride, copper chloride, cesium fluoride, niobium fluoride, calcium bromide, vanadium bromide, molecular sieve, zeolite and magnesium oxide. Though the inert liquid is not particularly limited, examples thereof include paraffins, liquid paraffins, fluorine based solvents such as perfluoroalkanes, perfluoroamines and perfluoroethers, chlorine based solvents and silicon oils.

Also, a method for sealing with a resin sealing layer as described below is suitably adopted.

(Resin Sealing Layer)

It is preferred to suppress deterioration of performances of the functional device of the invention, which is caused due to contact with oxygen or moisture in the atmosphere by a resin sealing layer.

(Material)

A resin material for the resin sealing layer is not particularly limited, and acrylic resins, epoxy resins, fluorine based resins, silicon based resins, rubber based resins, ester based resins and so on are useful. Of these, epoxy resins are preferable from the standpoint of a moisture preventive function thereof. Of the epoxy resins, thermosetting epoxy resins and photocurable epoxy resins are preferable.

(Preparation Method)

A method for preparing a resin sealing layer is not particularly limited, and examples thereof include a method for coating a resin solution, a method for press bonding or hot press bonding of a resin sheet and a method for dry polymerization by vapor deposition, sputtering or the like.

(Film Thickness)

A thickness of the resin sealing layer is preferably 1 μm or more and not more than 1 mm, more preferably 5 μm or more and not more than 100 μm, and most preferably 10 μm or more and not more than 50 μm. When the thickness of the resin sealing layer is thinner than the foregoing range, there is a concern that the inorganic film is damaged at the time of mounting a second substrate. On the other hand, when the thickness of the resin sealing layer is thicker than the foregoing range, a thickness of the electroluminescence device itself becomes thick, thereby impairing characteristic features of the organic electroluminescence device, that is, thin film properties.

(Sealing Adhesive)

A sealing adhesive which is used in the invention has a function of preventing intrusion of moisture or oxygen from the edge.

(Material)

As a material for the sealing adhesive, the same materials as those used for the resin sealing layer are useful. Of these, epoxy based adhesives are preferable from the standpoint of preventing intrusion of moisture, and photocurable adhesives or thermosetting adhesives are especially preferable.

Also, it is preferred to add a filler to the foregoing material.

The filler which is added to the sealing agent is preferably an inorganic material such as $SiO_2$, SiO (silicon oxide), SiON (silicon oxynitride) and SiN (silicon nitride). The addition of the filler increases a viscosity of the sealing agent, thereby enhancing processing adaptability and enhancing humidity resistance.

(Drying Agent)

The sealing adhesive may contain a drying agent. The drying agent is preferably barium oxide, calcium oxide or strontium oxide.

The addition amount of the drying agent is preferably 0.01% by mass or more and not more than 20% by mass, and more preferably 0.05% by mass or more and not more than 15% by mass relative to the sealing adhesive. When the addition amount of the drying agent is less than the foregoing range, addition effects of the drying agent become insufficient. On the other hand, what the addition amount of the drying agent exceeds the foregoing range is not preferable because it is difficult to uniformly disperse the drying agent in the sealing adhesive.

(Formulation of Sealing Adhesive)

Polymer Composition and Concentration:

The sealing adhesive is not particularly limited, and those described previously are useful. Examples of the photocurable epoxy adhesive include XNR5516, manufactured by Nagase Chemtex Corporation. The sealing adhesive may be prepared by adding the drying agent directly to the sealing adhesive and then dispersing the resulting mixture.

Thickness:

A coating thickness of the sealing adhesive is preferably 1 μm or more and not more than 1 mm. What the coating thickness of the sealing adhesive is thinner than the foregoing range is not preferable because the sealing adhesive cannot be uniformly coated. On the other hand, what the coating thickness of the sealing adhesive exceeds the foregoing range is not preferable, too because a moisture intrusion path becomes wide.

(Sealing Method)

In the invention, the functional device is able to be obtained by coating an arbitrary amount of the sealing adhesive having the drying agent incorporated therein by using a disperser or the like, then superimposing a second substrate thereon and thereafter curing the stack.

[Driving]

According to the organic EL device of the invention, light emission can be obtained by applying a voltage of direct current (optionally containing an alternating current component) (usually from 2 volts to 15 volts) or a current of direct current between the anode and the cathode.

As to the driving method of the organic EL device of the invention, driving methods disclosed in JP-A-2-148687, JP-A-6-301355, JP-A-5-29080, JP-A-7-134558, JP-A-8-234685, JP-A-8-241047, Japanese Patent No. 2784615 and U.S. Pat. Nos. 5,828,429 and 6,023,308 can be applied.

[Application of the Present Invention]

The organic electroluminescence device of the invention can be suitably utilized for display devices, displays, backlights, electrophotography (xerography), illumination light sources, recording light sources, exposure light sources, read light sources, markers, signboards, interiors, optical communications and so on.

EXAMPLES

The invention is hereunder described in detail with reference to the following Examples, but it should not be construed that the invention is limited thereto.

Synthesis Example 1

Synthesis of Illustrative Compound 1

Illustrative Compound 1 may be synthesized according to the following scheme.

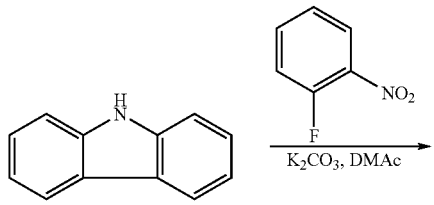

Compound A was obtained in a yield of 82% by heat refluxing carbazole and 1-fluoro-2-nitrobenzene in the coexistence of potassium carbonate for 4 hours. The Compound A was reduced with a tin powder and converted into Compound B in a yield of 89%. The Compound B was allowed to react with sodium nitrite in a solvent of sulfuric acid (concentration: 18% by volume) and acetic acid (concentration: 82% by volume) at 0° C. and then condensed by means of heat decomposition, thereby obtaining Compound C in a yield of 62%. The Compound C was brominated in chloroform to obtain Compound D in a yield of 56%. The Compound D was allowed to react with normal butyllithium in a THF solvent. Triphenylchlorosilane was added thereto, and the mixture was allowed to react at room temperature for one hour. The reaction mixture was hydrolyzed with a sodium hydrogencarbonate aqueous solution, thereby obtaining Illustrative Compound 1 in a yield of 27%.

$^1$H-NMR data of Illustrative Compound 1: (400 MHz, CDCl$_3$): δ/ppm 8.24 (s, 2H), 8.07 (d, J=7.5 Hz, 2H), 7.92 (d, J=8.05 Hz, 2H), 7.72 to 7.75 (m, 6H), 7.58 to 7.52 (m, 2H), 7.49 to 7.38 (m, 9H), 7.36 to 7.30 (m, 2H)

Preparation of Organic Electroluminescence Device

Comparative Example 1-1

A washed ITO substrate was put into a vapor deposition apparatus; copper phthalocyanine was vapor deposited thereon in a thickness of 10 nm; and NPD ((N,N'-di-α-naphthyl-N,N'-diphenyl)-benzidine) was further vapor deposited thereon in a thickness of 40 nm. Compound A-1 and Compound B were vapor deposited thereon at a ratio of 12/88 (mass ratio) in a thickness of 30 nm (light emitting layer); BAlq [bis-(2-methyl-8-quinolinolate)-4-(phenylphenolate) aluminum][bis(6-hydroxyquinoline)-4-(phenyl-phenol) Al complex salt] was further vapor deposited thereon in a thickness of 30 nm; and Alq (tris(8-hydroxyquinoline)aluminum complex) was then additionally vapor deposited thereon in a thickness of 10 nm (electron transport layer). After vapor depositing thereon lithium fluoride in a thickness of 3 nm, aluminum was vapor deposited in a thickness of 60 nm. The resultant was put into a glove box purged with an argon gas without being brought into contact with the air and sealed in a sealing can made of stainless steel with a UV-curable adhesive (XNR5516HV, manufactured by Nagase-Ciba Ltd.) to obtain an organic electroluminescence device of Comparative Example 1. The EL device was subjected to light emission upon being impressed with a direct current constant voltage using a source measure unit MODEL 2400, manufactured by Toyo Corporation. As a result, phosphorescence derived from the Compound A-1 was obtained. A vapor deposition rate was regulated to be 0.2 nm/sec.

Also, a film thickness was calculated from a vapor deposition rate measured by a quartz crystal deposition controller CRTM-9000, manufactured by ULVAC, Inc. and a calibration curve prepared on the basis of film thickness values obtained by a DEKTAK type stylus film thickness measurer.

Examples 1-1 to 1-55 and Comparative Examples 1-2 to 1-15

Devices were prepared in the same manner as in Comparative Example 1-1, except for changing the compound used in the light emitting layer to a compound shown in Table 1 and then evaluated. As a result, phosphorescence derived from each of the used light emitting materials was obtained. The obtained results are summarized in Table 1.

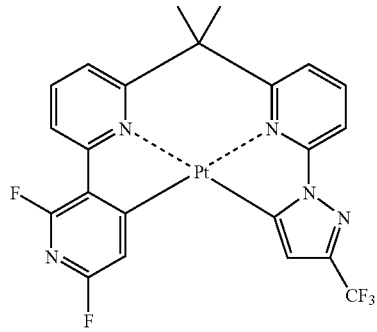

A-3

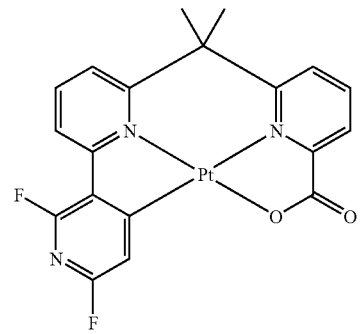

A-4

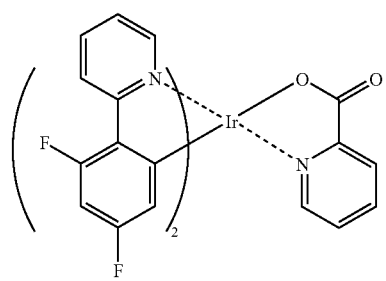

A-1

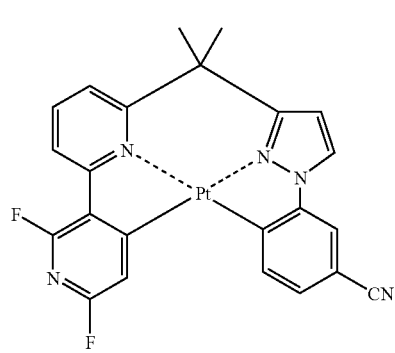

A-5

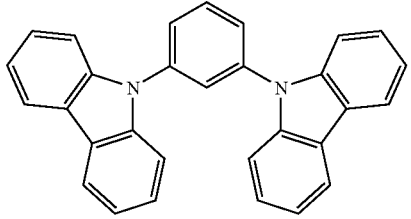

B

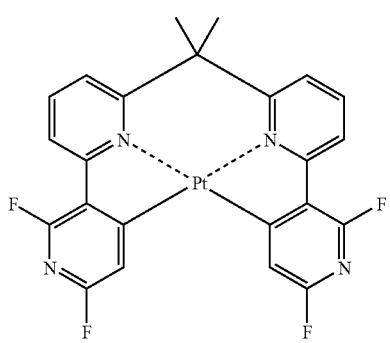

A-2

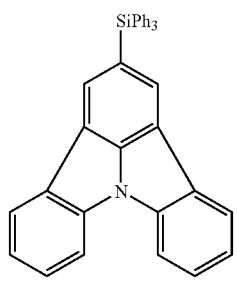

C-1

-continued
C-2
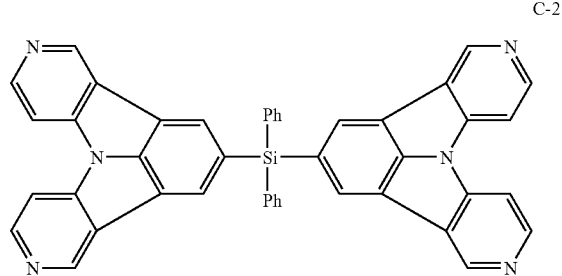
C-3
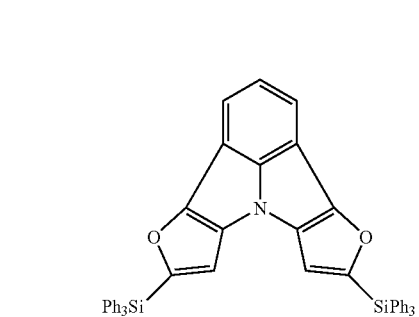
C-4
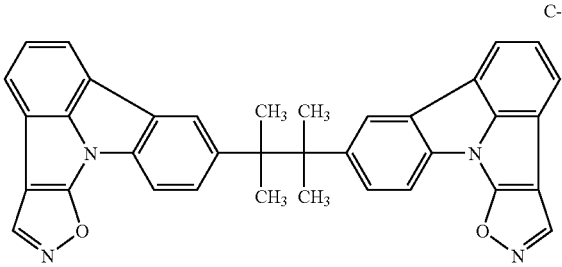
C-5
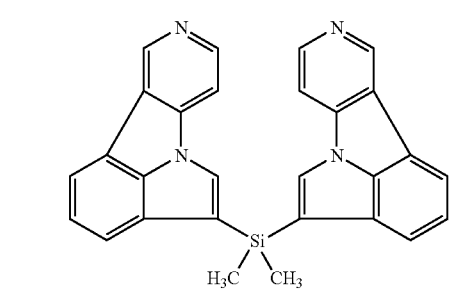
C-6
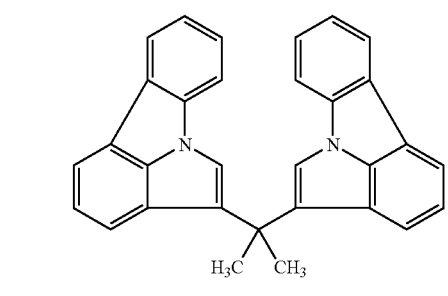
-continued
C-7
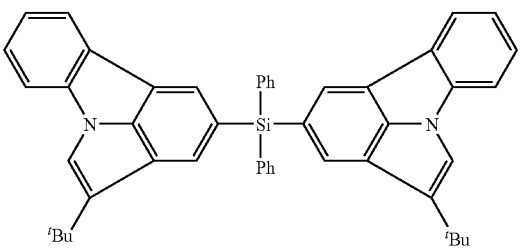
C-8
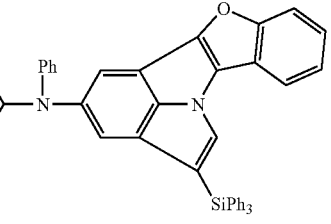
C-9
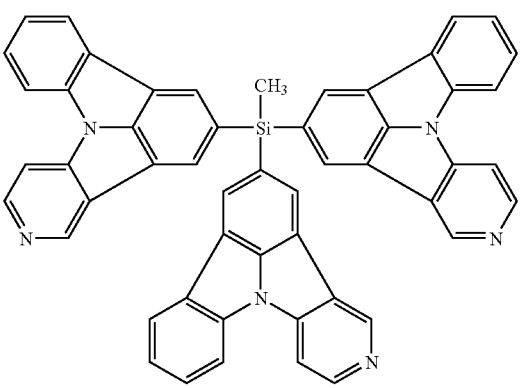
C-10
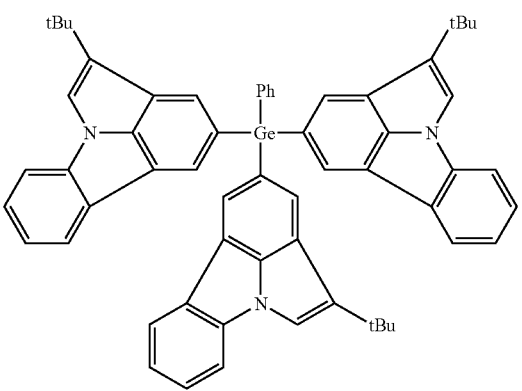

-continued

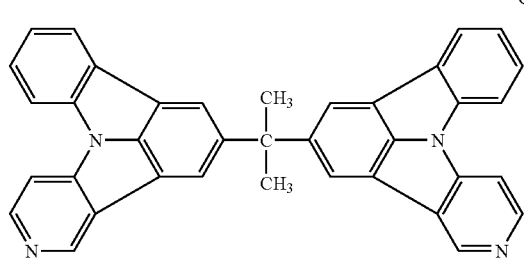

C-11

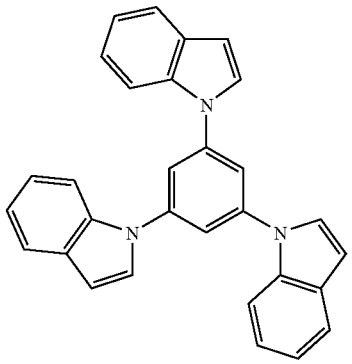

D-2

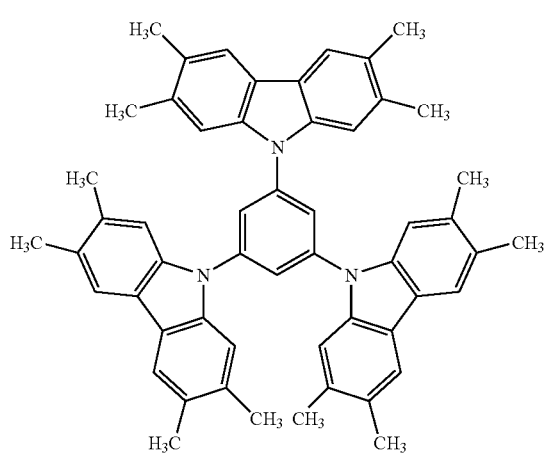

D-1

[Evaluation of Performances of Organic Electroluminescence Device]

(a) External Quantum Efficiency:

Each of the devices was subjected to light emission upon being impressed with a direct current using a source measure unit MODEL 2400, manufactured by Toyo Corporation. Its brightness was measured using BM-8, manufactured by Topcon Corporation. An emission spectrum and an emission wavelength were measured using a spectral analyzer PMA-11, manufactured by Hamamatsu Photonics K.K. An external quantum efficiency at a brightness in the vicinity of 1,000 cd/m² was calculated based on these measured values according to a brightness conversion method, and a relative value thereof was determined (b) Driving Voltage:

Each of the devices was subjected to light emission upon being impressed with a direct current such that the brightness was 1,000 cd/m². At that time, an impressed voltage was defined as an index for the evaluation of driving voltage.

TABLE 1

| | | Light emitting layer | External quantum efficiency (relative value) | Difference in driving voltage from Comparative Example 1-1 (ΔV) |
|---|---|---|---|---|
| Comparative Example 1-1 | A-1 | B | 1.00 | — |
| Example 1-1 | A-1 | C-1 | 1.53 | −0.89 |
| Example 1-2 | A-1 | C-2 | 1.44 | −1.33 |
| Example 1-3 | A-1 | C-3 | 1.32 | −0.85 |
| Example 1-4 | A-1 | C-4 | 1.29 | −0.93 |
| Example 1-5 | A-1 | C-5 | 1.41 | −1.15 |
| Example 1-6 | A-1 | C-6 | 1.63 | −1.01 |
| Example 1-7 | A-1 | C-7 | 1.49 | −1.13 |
| Example 1-8 | A-1 | C-8 | 1.39 | −0.78 |
| Example 1-9 | A-1 | C-9 | 1.43 | −0.82 |
| Example 1-10 | A-1 | C-10 | 1.55 | −0.97 |
| Example 1-11 | A-1 | C-11 | 1.38 | −1.18 |
| Comparative Example 1-2 | A-1 | Illustrative Compound 9 of JP-A-2004-171808 | 1.12 | −0.55 |
| Comparative Example 1-3 | A-1 | Illustrative Compound A-4 of JP-A-2002-100467 | 1.22 | −0.68 |

TABLE 1-continued

| | | Light emitting layer | External quantum efficiency (relative value) | Difference in driving voltage from Comparative Example 1-1 (ΔV) |
|---|---|---|---|---|
| Comparative Example 1-4 | A-2 | B | 1.13 | −0.66 |
| Example 1-12 | A-2 | C-1 | 1.73 | −1.32 |
| Example 1-13 | A-2 | C-2 | 1.66 | −1.92 |
| Example 1-14 | A-2 | C-3 | 1.58 | −1.29 |
| Example 1-15 | A-2 | C-4 | 1.46 | −1.27 |
| Example 1-16 | A-2 | C-5 | 1.61 | −1.28 |
| Example 1-17 | A-2 | C-6 | 1.79 | −1.75 |
| Example 1-18 | A-2 | C-7 | 1.53 | −1.71 |
| Example 1-19 | A-2 | C-8 | 1.48 | −1.74 |
| Example 1-20 | A-2 | C-9 | 1.62 | −1.54 |
| Example 1-21 | A-2 | C-10 | 1.68 | −1.66 |
| Example 1-22 | A-2 | C-2 | 1.58 | −1.84 |
| Comparative Example 1-5 | A-2 | D-1 | 1.23 | −0.72 |
| Comparative Example 1-6 | A-2 | D-2 | 1.28 | −0.88 |
| Example 1-23 | A-3 | C-1 | 1.86 | −1.36 |
| Example 1-24 | A-3 | C-2 | 1.75 | −1.97 |
| Example 1-25 | A-3 | C-3 | 1.70 | −1.33 |
| Example 1-26 | A-3 | C-4 | 1.53 | −1.34 |
| Example 1-27 | A-3 | C-5 | 1.74 | −1.33 |
| Example 1-28 | A-3 | C-6 | 1.90 | −1.80 |
| Example 1-29 | A-3 | C-7 | 1.61 | −1.73 |
| Example 1-30 | A-3 | C-8 | 1.56 | −1.77 |
| Example 1-31 | A-3 | C-9 | 1.71 | −1.92 |
| Example 1-32 | A-3 | C-10 | 1.73 | −1.45 |
| Example 1-33 | A-3 | C-11 | 1.66 | −1.86 |
| Comparative Example 1-7 | A-3 | B | 1.22 | −0.71 |
| Comparative Example 1-8 | A-3 | D-1 | 1.26 | −0.72 |
| Comparative Example 1-9 | A-3 | D-2 | 1.30 | −0.87 |
| Example 1-34 | A-4 | C-1 | 1.77 | −1.33 |
| Example 1-35 | A-4 | C-2 | 1.71 | −1.90 |
| Example 1-36 | A-4 | C-3 | 1.66 | −1.28 |
| Example 1-37 | A-4 | C-4 | 1.44 | −1.20 |
| Example 1-38 | A-4 | C-5 | 1.69 | −1.29 |
| Example 1-39 | A-4 | C-6 | 1.80 | −1.71 |
| Example 1-40 | A-4 | C-7 | 1.55 | −1.67 |
| Example 1-41 | A-4 | C-8 | 1.52 | −1.62 |
| Example 1-42 | A-4 | C-9 | 1.66 | −1.79 |
| Example 1-43 | A-4 | C-10 | 1.73 | −1.36 |
| Example 1-44 | A-4 | C-11 | 1.64 | −1.84 |
| Comparative Example 1-10 | A-4 | B | 1.17 | −0.66 |
| Comparative Example 1-11 | A-4 | D-1 | 1.21 | −0.68 |
| Comparative Example 1-12 | A-4 | D-2 | 1.23 | −0.87 |
| Example 1-45 | A-5 | C-1 | 1.91 | −1.42 |
| Example 1-46 | A-5 | C-2 | 1.79 | −2.05 |
| Example 1-47 | A-5 | C-3 | 1.73 | −1.38 |
| Example 1-48 | A-5 | C-4 | 1.57 | −1.37 |
| Example 1-49 | A-5 | C-5 | 1.81 | −1.35 |
| Example 1-50 | A-5 | C-6 | 1.94 | −1.91 |
| Example 1-51 | A-5 | C-7 | 1.68 | −1.77 |
| Example 1-52 | A-5 | C-8 | 1.63 | −1.83 |
| Example 1-53 | A-5 | C-9 | 1.82 | −1.98 |
| Example 1-54 | A-5 | C-10 | 1.83 | −1.44 |
| Example 1-55 | A-5 | C-11 | 1.72 | −1.98 |
| Comparative Example 1-13 | A-5 | B | 1.23 | −0.73 |
| Comparative Example 1-14 | A-5 | D-1 | 1.25 | −0.75 |
| Comparative Example 1-15 | A-5 | D-2 | 1.32 | −0.85 |

As is clear from the foregoing results, the devices of the invention are high in the external quantum efficiency and low in the driving voltage as compared with the comparative devices.

Comparative Example 2-1

Similar to Comparative Example 1-1, a washed ITO substrate was put into a vapor deposition apparatus; copper phthalocyanine was vapor deposited thereon in a thickness of 10 nm; and NPD ((N,N'-di-α-naphthyl-N,N'-diphenyl)-benzidine) was further vapor deposited thereon in a thickness of 40 nm. Compound A-6 and Compound B were vapor deposited thereon at a ratio of 12/88 (mass ratio) in a thickness of 20 nm, thereby fabricating a light emitting layer. BAlq [bis-(2-methyl-8-quinolinolate)-4-(phenylphenolate)aluminum][bis(6-hydroxyquinoline)-4-(phenyl-phenol) Al complex salt] was further vapor deposited thereon in a thickness of 40 nm (electron transport layer). After vapor depositing thereon lithium fluoride in a thickness of 3 nm, aluminum was vapor deposited in a thickness of 60 nm to prepare a device. The EL device was subjected to light emission upon being impressed with a direct current constant voltage using a source measure unit MODEL 2400, manufactured by Toyo Corporation. As a result, phosphorescence derived from the Compound A-6 was obtained.

Examples 2-1 to 2-16 and Comparative Examples 2-2 to 2-6

Devices were prepared in the same manner as in Comparative Example 2-1, except for changing the compound used in the light emitting layer to a compound shown in Table 2 and then evaluated. As a result, phosphorescence derived from each of the used light emitting materials was obtained. The obtained results are summarized in Table 2.

TABLE 2

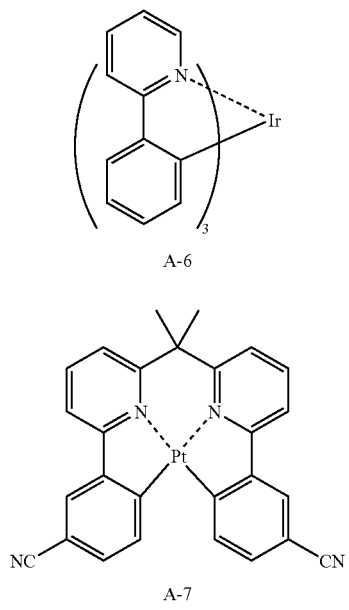

| | Light emitting layer | | External quantum efficiency (relative value) | Difference in driving voltage from Comparative Example 2-1 (ΔV) |
|---|---|---|---|---|
| Comparative Example 2-1 | A-6 | B | 1.00 | — |
| Example 2-1 | A-6 | C-1 | 1.32 | −1.54 |

| | | | | |
|---|---|---|---|---|
| Example 2-2 | A-6 | C-3 | 1.24 | −1.33 |
| Example 2-3 | A-6 | C-5 | 1.37 | −1.69 |
| Example 2-4 | A-6 | C-6 | 1.41 | −1.58 |
| Example 2-5 | A-6 | C-12 | 1.47 | −1.72 |
| Example 2-6 | A-6 | C-13 | 1.44 | −1.60 |
| Example 2-7 | A-6 | C-14 | 1.52 | −1.66 |
| Example 2-8 | A-6 | C-15 | 1.39 | −1.71 |
| Comparative Example 2-2 | A-6 | D-1 | 0.98 | −0.88 |
| Comparative Example 2-3 | A-6 | D-2 | 1.09 | −0.95 |
| Comparative Example 2-4 | A-7 | B | 0.98 | −0.12 |
| Example 2-9 | A-7 | C-1 | 1.42 | −1.81 |
| Example 2-10 | A-7 | C-3 | 1.39 | −1.57 |
| Example 2-11 | A-7 | C-5 | 1.45 | −1.73 |
| Example 2-12 | A-7 | C-6 | 1.44 | −1.64 |
| Example 2-13 | A-7 | C-12 | 1.54 | −1.78 |
| Example 2-14 | A-7 | C-13 | 1.59 | −1.75 |
| Example 2-15 | A-7 | C-14 | 1.61 | −1.74 |
| Example 2-16 | A-7 | C-15 | 1.63 | −1.65 |
| Comparative Example 2-5 | A-7 | D-1 | 1.03 | −0.85 |
| Comparative Example 2-6 | A-7 | D-2 | 1.08 | −1.07 |

As is clear from the foregoing results, the devices of the invention are high in the external quantum efficiency and low in the driving voltage as compared with the comparative devices.

Comparative Example 3-1

A washed ITO substrate was put into a vapor deposition apparatus; copper phthalocyanine was vapor deposited thereon in a thickness of 10 nm; and NPD ((N,N'-di-α-naphthyl-N,N'-diphenyl)-benzidine) was further vapor deposited thereon in a thickness of 40 nm. Compound A-8 and CBP (4,4'-di(9-carbazoyl)biphenyl) were vapor deposited thereon at a ratio of 12/88 (mass ratio) in a thickness of 15 nm, thereby fabricating a light emitting layer. BAlq [bis-(2-methyl-8-quinolinolate)-4-(phenylphenolate)aluminum][bis(6-hydroxyquinoline)-4-(phenyl-phenol) Al complex salt] was further vapor deposited thereon in a thickness of 40 nm (electron transport layer). After vapor depositing thereon lithium fluoride in a thickness of 3 nm, aluminum was vapor deposited in a thickness of 60 nm to prepare a device. The EL device was subjected to light emission upon being impressed with a direct current constant voltage using a source measure unit MODEL 2400, manufactured by Toyo Corporation. As a result, phosphorescence derived from the Compound A-8 was obtained.

Examples 3-1 to 3-6 and Comparative Examples 3-2 to 3-3

Devices were prepared in the same manner as in Comparative Example 3-1, except for changing the compound used in the light emitting layer to a compound shown in Table 3 and then evaluated. As a result, phosphorescence derived from each of the used light emitting materials was obtained. The obtained results are summarized in Table 3.

TABLE 3

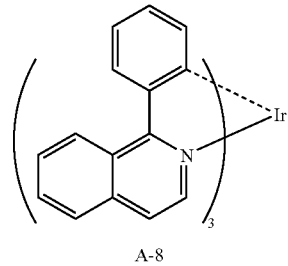

A-8

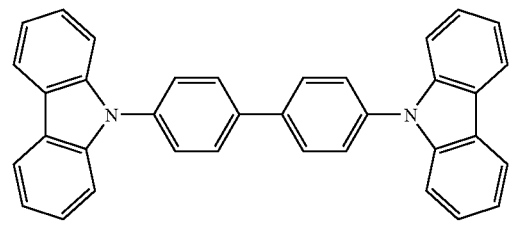

CBP

| Light emitting layer | | | External quantum efficiency (relative value) | Difference in driving voltage from Comparative Example 3-1 (ΔV) |
|---|---|---|---|---|
| Comparative Example 3-1 | A-8 | CBP | 1.00 | — |
| Example 3-1 | A-8 | C-1 | 1.25 | −1.33 |
| Example 3-2 | A-8 | C-3 | 1.21 | −1.28 |
| Example 3-3 | A-8 | C-5 | 1.39 | −1.66 |
| Example 3-4 | A-8 | C-6 | 1.38 | −1.55 |
| Example 3-5 | A-8 | C-9 | 1.50 | −1.67 |
| Example 3-6 | A-8 | C-10 | 1.42 | −1.51 |
| Comparative Example 3-2 | A-8 | D-1 | 1.04 | −0.78 |
| Comparative Example 3-3 | A-8 | D-2 | 1.09 | −0.84 |

As is clear from the foregoing results, the devices of the invention are high in the external quantum efficiency and low in the driving voltage as compared with the comparative devices.

Comparative Example 4-1

A washed ITO substrate was put into a vapor deposition apparatus; copper phthalocyanine was vapor deposited thereon in a thickness of 10 nm; and NPD ((N,N'-di-α-naphthyl-N,N'-diphenyl)-benzidine) was further vapor deposited thereon in a thickness of 40 nm. Rubrene and Compound D-1 were vapor deposited thereon at a ratio of 3/97 (mass ratio) in a thickness of 10 nm, thereby fabricating a light emitting layer. BAlq [bis-(2-methyl-8-quinolinolate)-4-(phenylphenolate)aluminum][bis(6-hydroxyquinoline)-4-(phenyl-phenol) Al complex salt] was further vapor deposited thereon in a thickness of 40 nm (electron transport layer). After vapor depositing thereon lithium fluoride in a thickness of 3 nm, aluminum was vapor deposited in a thickness of 60 nm to prepare a device. The EL device was subjected to light emission upon being impressed with a direct current constant voltage using a source measure unit MODEL 2400, manufactured by Toyo Corporation. As a result, phosphorescence derived from rubrene was obtained.

Examples 4-1 to 4-3

Devices were prepared in the same manner as in Comparative Example 4-1, except for changing the compound used in the light emitting layer to a compound shown in Table 4 and then evaluated. As a result, phosphorescence derived from each of the used light emitting materials was obtained. The obtained results are summarized in Table 4.

TABLE 4

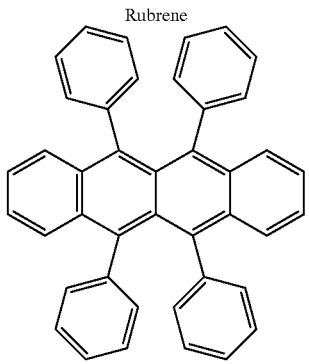

Rubrene

| | Light emitting layer | External quantum efficiency (relative value) | Difference in driving voltage from Comparative Example 4-1 (ΔV) |
|---|---|---|---|
| Comparative Example 4-1 | Rubrene D-1 | 1.00 | — |
| Example 4-1 | Rubrene C-10 | 1.56 | −1.56 |
| Example 4-2 | Rubrene C-9 | 1.77 | −1.63 |
| Example 4-3 | Rubrene C-1 | 1.65 | −1.86 |

As is clear from the foregoing results, the devices of the invention are high in the external quantum efficiency and low in the driving voltage as compared with the comparative devices.

Comparative Example 5-1

Similar to Comparative Example 1-1, a washed ITO substrate was put into a vapor deposition apparatus; copper phthalocyanine was vapor deposited thereon in a thickness of 10 nm; and NPD ((N,N'-di-α-naphthyl-N,N'-diphenyl)-benzidine) was further vapor deposited thereon in a thickness of 37 nm. Compound D-1 was vapor deposited thereon in a thickness of 3 mm. Compound A-1 and Compound B were vapor deposited thereon at a ratio of 12/88 (mass ratio) in a thickness of 20 nm, thereby fabricating a light emitting layer. BAlq [bis-(2-methyl-8-quinolinolate)-4-(phenylphenolate) aluminum][bis(6-hydroxyquinoline)-4-(phenyl-phenol) Al complex salt] was further vapor deposited thereon in a thickness of 40 nm (electron transport layer). After vapor depositing thereon lithium fluoride in a thickness of 3 nm, aluminum was vapor deposited in a thickness of 60 nm to prepare a device. The EL device was subjected to light emission upon being impressed with a direct current constant voltage using a source measure unit MODEL 2400, manufactured by Toyo Corporation. As a result, phosphorescence derived from the Compound A-1 was obtained.

Examples 5-1 to 5-3

Devices were prepared in the same manner as in Comparative Example 5-1, except for changing the compound used in the light emitting layer to a compound shown in Table 5 and then evaluated. As a result, phosphorescence derived from each of the used light emitting materials was obtained. The obtained results are summarized in Table 5.

TABLE 5

| | Hole transport layer | Light emitting layer | | External quantum efficiency (relative value) | Difference in driving voltage from Comparative Example 5-1 (ΔV) |
|---|---|---|---|---|---|
| Comparative Example 5-1 | D-1 | A-1 | B | 1.00 | — |
| Example 5-1 | C-1 | A-1 | B | 1.05 | −0.52 |
| Example 5-2 | C-9 | A-1 | B | 1.22 | −1.38 |
| Example 5-3 | C-10 | A-1 | B | 1.23 | −0.96 |

As is clear from the foregoing Examples, it was noted that the devices of the invention containing the compound represented by the formula (1) in the layer (hole transport layer) adjacent to the light emitting layer on the side close to the anode are able to enhance the external quantum efficiency of the electroluminescence device and to achieve low-voltage driving.

Comparative Example 6-1

Similar to Comparative Example 1-1, a washed ITO substrate was put into a vapor deposition apparatus; copper phthalocyanine was vapor deposited thereon in a thickness of 10 nm; and NPD ((N,N'-di-α-naphthyl-N,N'-diphenyl)-benzidine) was further vapor deposited thereon in a thickness of 40 nm. Compound A-1 and Compound B were vapor deposited thereon at a ratio of 12/88 (mass ratio) in a thickness of 20 nm, thereby fabricating a light emitting layer. Compound D-2 was vapor deposited thereon in a thickness of 10 nm. BAlq [bis-(2-methyl-8-quinolinolate)-4-(phenylphenolate)aluminum][bis(6-hydroxyquinoline)-4-(phenyl-phenol) Al complex salt] was further vapor deposited thereon in a thickness of 30 nm (electron transport layer). After vapor depositing thereon lithium fluoride in a thickness of 3 nm, aluminum was vapor deposited in a thickness of 60 nm to prepare a device. The EL device was subjected to light emission upon being impressed with a direct current constant voltage using a source measure unit MODEL 2400, manufactured by Toyo Corporation. As a result, phosphorescence derived from the Compound A-1 was obtained.

Examples 6-1 to 6-3

Devices were prepared in the same manner as in Comparative Example 6-1, except for changing the compound used in the light emitting layer to a compound shown in Table 6 and then evaluated. As a result, phosphorescence derived from each of the used light emitting materials was obtained. The obtained results are summarized in Table 6.

TABLE 6

| | Light emitting layer | Electron transport layer | External quantum efficiency (relative value) | Difference in driving voltage from Comparative Example 6-1 (ΔV) |
|---|---|---|---|---|
| Comparative Example 6-1 | A-1 | B D-1 | 1.00 | — |
| Example 6-1 | A-1 | B C-5 | 1.14 | −0.89 |
| Example 6-2 | A-1 | B C-6 | 1.28 | −1.21 |
| Example 6-3 | A-1 | B C-10 | 1.19 | −1.07 |

As is clear from the foregoing Examples, it was noted that the devices of the invention containing the compound represented by the formula (1) in the layer (electron transport layer) adjacent to the light emitting layer on the side close to the cathode are able to enhance the external quantum efficiency of the electroluminescence device and to achieve low-voltage driving.

The organic electroluminescence device of the invention is characterized in that at least one of the compounds represented by the formula (1) is contained in the organic compound layer. According to this, an organic electroluminescence device (synonymous with the "device of the invention" in this specification) having high luminous efficiency (for example, external quantum efficiency) and capable of being driven at a low voltage may be provided.

The entire disclosure of each and every foreign patent application from which the benefit of foreign priority has been claimed in the present application is incorporated herein by reference, as if fully set forth.

What is claimed is:

1. An organic electroluminescence device, comprising:
a pair of electrodes; and
at least one organic layer including a light emitting layer, the light emitting layer being provided between the pair of electrodes,
wherein at least one layer of the at least one organic layer contains a compound represented by formula (1):

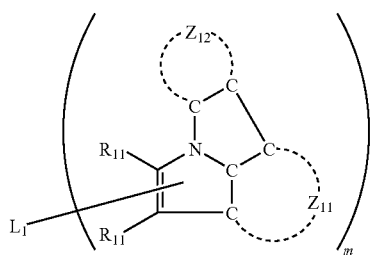

(1)

wherein each of $Z_{11}$ and $Z_{12}$ independently represents an aromatic heterocyclic ring or an aromatic hydrocarbon ring;

$R_{11}$ represents a hydrogen atom or a substituent, provided that a plurality of $R_{11}$s are the same or different;

m represents an integer of 1 or more; and $L_1$ represents a single bond or an m-valent linking group and is linked to any one of C atoms in $R_{11}$, $Z_{11}$ and $Z_{12}$, provided that when m is 1, $L_1$ does not exist.

2. The organic electroluminescence device according to claim 1,
wherein the compound represented by formula (1) is a compound represented by formula (2):

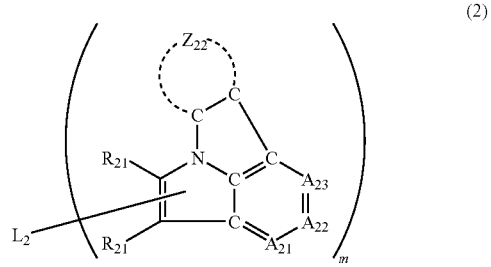

(2)

wherein $Z_{22}$ represents an aromatic heterocyclic ring or an aromatic hydrocarbon ring;

$R_{21}$ represents a hydrogen atom or a substituent, provided that a plurality of $R_{21}$s are the same or different;

each of $A_{21}$ to $A_{23}$ independently represents a nitrogen atom or C—$R_{22}$;

$R_{22}$ represents a hydrogen atom or a substituent, provided that a plurality of $R_{22}$s are the same or different;

m represents an integer of 1 or more; and $L_2$ represents a single bond or an m-valent linking group and is linked to any one of C atoms in $R_{21}$, $Z_{22}$ and $A_{21}$ to $A_{23}$, provided that when m is 1, $L_2$ does not exist.

3. The organic electroluminescence device according to claim 1,
wherein the compound represented by formula (1) is a compound represented by formula (3):

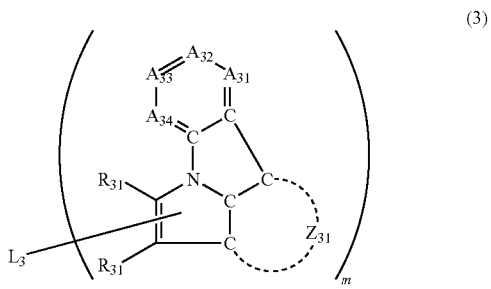

(3)

wherein $Z_{31}$ represents an aromatic heterocyclic ring or an aromatic hydrocarbon ring;

$R_{31}$ represents a hydrogen atom or a substituent, provided that a plurality of $R_{31}$s are the same or different;

each of $A_{31}$ to $A_{34}$ independently represents a nitrogen atom or C—$R_{32}$;

$R_{32}$ represents a hydrogen atom or a substituent, provided that a plurality of $R_{32}$s are the same or different;

m represents an integer of 1 or more; and $L_3$ represents a single bond or an m-valent linking group and is linked to any one of C atoms in $R_{31}$, $Z_{31}$ and $A_{31}$ to $A_{34}$, provided that when m is 1, $L_3$ does not exist.

4. The organic electroluminescence device according to claim 2,
wherein the compound represented by formula (2) is a compound represented by formula (4):

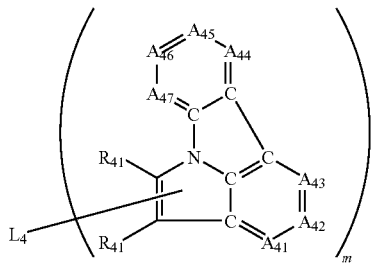
(4)

wherein $R_{41}$ represents a hydrogen atom or a substituent, provided that a plurality of $R_{41}$s are the same or different;
each of $A_{41}$ to $A_{47}$ independently represents a nitrogen atom or C—$R_{42}$;
$R_{42}$ represents a hydrogen atom or a substituent, provided that a plurality of $R_{42}$s are the same or different;
m represents an integer of 1 or more; and
$L_4$ represents a single bond or an m-valent linking group and is linked to any one of C atoms in $R_{41}$ and $A_{41}$ to $A_{47}$, provided that when m is 1, $L_4$ does not exist.

5. The organic electroluminescence device according to claim 1,
wherein the compound represented by formula (1) is a compound represented by formula (5):

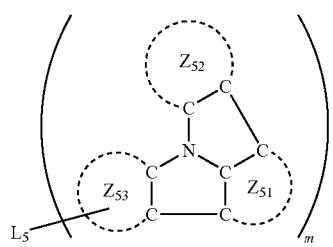
(5)

wherein each of $Z_{51}$ to $Z_{53}$ independently represents an aromatic heterocyclic ring or an aromatic hydrocarbon ring;
m represents an integer of 1 or more; and
$L_5$ represents a single bond or an m-valent linking group and is linked to any one of C atoms in $Z_{51}$ to $Z_{53}$, provided that when m is 1, $L_5$ does not exist.

6. The organic electroluminescence device according to claim 5,
wherein the compound represented by the formula (5) is a compound represented by formula (6):

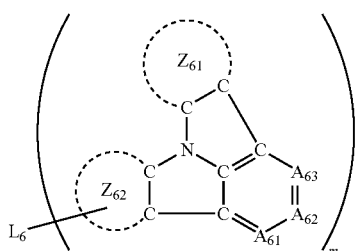
(6)

wherein each of $Z_{61}$ and $Z_{62}$ independently represents an aromatic heterocyclic ring or an aromatic hydrocarbon ring;
each of $A_{61}$ to $A_{63}$ independently represents a nitrogen atom or C—$R_{61}$;
$R_{61}$ represents a hydrogen atom or a substituent, provided that a plurality of $R_{61}$s are the same or different;
m represents an integer of 1 or more; and
$L_6$ represents a single bond or an m-valent linking group and is linked to any one of C atoms in $Z_{61}$, $Z_{62}$ and $A_{61}$ to $A_{63}$, provided that when m is 1, $L_6$ does not exist.

7. The organic electroluminescence device according to claim 6, wherein the compound represented by the formula (6) is a compound represented by formula (8):

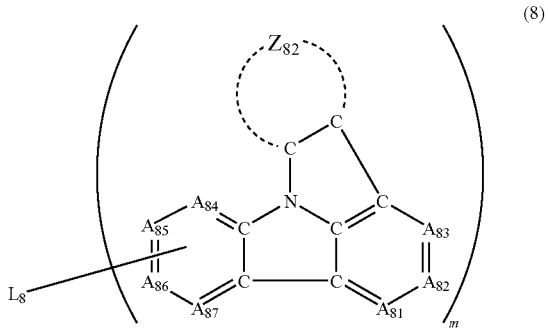
(8)

wherein $Z_{82}$ represents an aromatic heterocyclic ring or an aromatic hydrocarbon ring;
each of $A_{81}$ to $A_{87}$ independently represents a nitrogen atom or C—$R_{81}$;
$R_{81}$ represents a hydrogen atom or a substituent, provided that a plurality of $R_{81}$s are the same or different;
m represents an integer of 1 or more; and
$L_8$ represents a single bond or an m-valent linking group and is linked to any one of C atoms in $Z_{82}$ and $A_{81}$ to $A_{87}$, provided that when m is 1, $L_8$ does not exist.

8. The organic electroluminescence device according to claim 7,
wherein the compound represented by the formula (8) is a compound represented by formula (10):

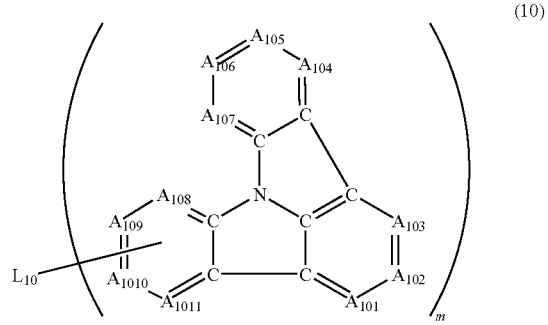
(10)

wherein each of $A_{101}$ to $A_{1011}$ independently represents a nitrogen atom or C—$R_{101}$;
$R_{101}$ represents a hydrogen atom or a substituent, provided that a plurality of $R_{101}$s are the same or different;
m represents an integer of 1 or more; and
$L_{10}$ represents a single bond or an m-valent linking group and is linked to any one of C atoms in $A_{101}$ to $A_{1011}$, provided that when m is 1, $L_{10}$ does not exist.

9. The organic electroluminescence device according to claim 5,
wherein the compound represented by formula (5) is a compound represented by formula (7):

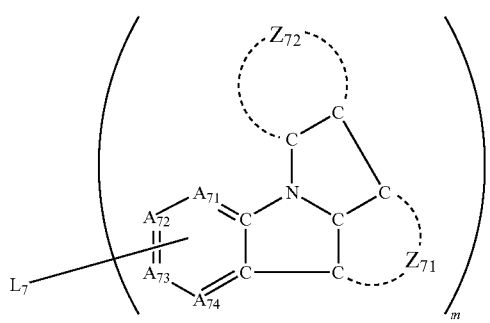

(7)

wherein each of $Z_{71}$ and $Z_{72}$ independently represents an aromatic heterocyclic ring or an aromatic hydrocarbon ring;
each of $A_{71}$ to $A_{74}$ independently represents a nitrogen atom or C—$R_{71}$;
$R_{71}$ represents a hydrogen atom or a substituent, provided that a plurality of $R_{71}$s are the same or different;
m represents an integer of 1 or more; and
$L_7$ represents a single bond or an m-valent linking group and is linked to any one of C atoms in $Z_{71}$, $Z_{72}$ and $A_{71}$ to $A_{74}$, provided that when m is 1, $L_7$ does not exist.

10. The organic electroluminescence device according to claim 9,
wherein the compound represented by the formula (7) is a compound represented by formula (9):

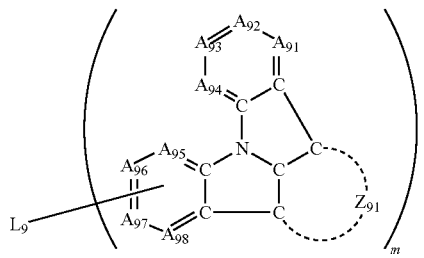

(9)

wherein $Z_{91}$ represents an aromatic heterocyclic ring or an aromatic hydrocarbon ring;
each of $A_{91}$ to $A_{98}$ independently represents a nitrogen atom or C—$R_{91}$;
$R_{91}$ represents a hydrogen atom or a substituent, provided that a plurality of $R_{91}$s are the same or different;
m represents an integer of 1 or more; and
$L_9$ represents a single bond or an m-valent linking group and is linked to any one of C atoms in $Z_{91}$ and $A_{91}$ to $A_{98}$, provided that when m is 1, $L_9$ does not exist.

11. The organic electroluminescence device according to claim 1,
wherein the light emitting layer contains the compound represented by formula (1).

12. The organic electroluminescence device according to claim 1,
wherein the pair of electrodes includes an anode,
a hole transport layer is provided between the light emitting layer and the anode, and
the hole transport layer contains the compound represented by formula (1).

13. The organic electroluminescence device according to claim 1,
wherein the pair of electrodes includes a cathode,
an electron transport layer is provided between the light emitting layer and the cathode, and
the electron transport layer contains the compound represented by formula (1).

14. The organic electroluminescence device according to claim 1,
wherein a glass transition temperature of the compound represented by formula (1) is 130° C. or higher and not higher than 450° C.

15. The organic electroluminescence device according to claim 1,
wherein a minimum excitation triplet energy level of the compound represented by formula (1) is 60 kcal/mole (251.4 kJ/mole) or more and not more than 95 kcal/mole (398.1 kJ/mole).

16. A compound represented by formula (4-1):

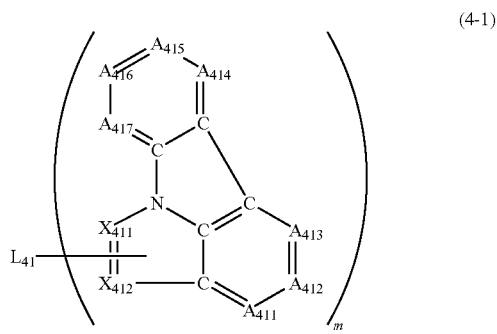

(4-1)

wherein each of $X_{411}$ and $X_{412}$ independently represents C—$R_{411}$;
$R_{411}$ represents a hydrogen atom or a substituent, provided that a plurality of $R_{412}$s are the same or different;
each of $A_{411}$ to $A_{417}$ independently represents a nitrogen atom or C—$R_{412}$;
$R_{412}$ represents a hydrogen atom or a substituent, provided that a plurality of $R_{412}$s are the same or different;
$L_{41}$ represents a single bond or an m-valent linking group and is linked to any one of C atoms in $X_{411}$, $X_{412}$ and $A_{411}$ to $A_{417}$;
when the linking group as $L_{41}$ is an aromatic hydrocarbon ring group or an aromatic heterocyclic group, a size of the ring is from a 5-membered to 6-membered ring; and
m represents an integer of 2 or more.

17. The compound according to claim 16, which is a compound represented by formula (4-2):

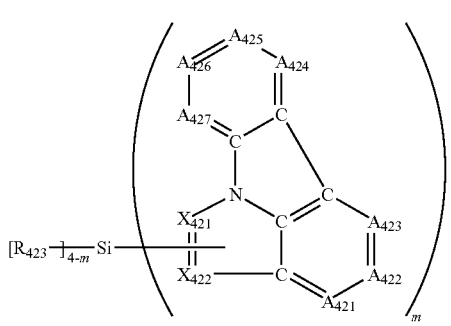

(4-2)

wherein each of $X_{421}$ and $X_{422}$ independently represents C—$R_{421}$;

$R_{421}$ represents a hydrogen atom or a substituent, provided that a plurality of $R_{421}$s are the same or different;

each of $A_{421}$ to $A_{427}$ independently represents a nitrogen atom or C—$R_{422}$;

$R_{422}$ represents a hydrogen atom or a substituent, provided that a plurality of $R_{422}$s are the same or different;

$R_{423}$ represents a hydrogen atom or a substituent, provided that a plurality of $R_{423}$s are the same or different;

m represents an integer of from 2 to 4; and the silicon linking group is linked to any one of C atoms in $X_{421}$, $X_{422}$ and $A_{421}$ to $A_{427}$.

18. The compound according to claim 16, which is a compound represented by formula (4-3):

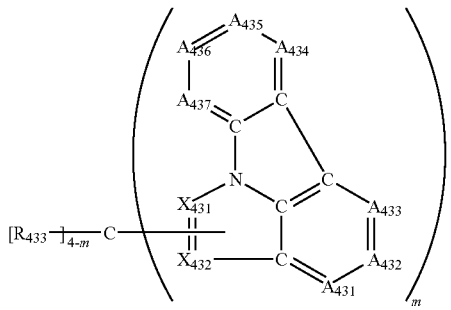

(4-3)

wherein each of $X_{431}$ and $X_{432}$ independently represents C—$R_{431}$;

$R_{431}$ represents a hydrogen atom or a substituent, provided that a plurality of $R_{431}$s are the same or different;

each of $A_{431}$ to $A_{437}$ independently represents a nitrogen atom or C—$R_{432}$;

$R_{432}$ represents a hydrogen atom or a substituent, provided that a plurality of $R_{432}$s are the same or different;

$R_{433}$ represents a hydrogen atom or a substituent, provided that a plurality of $R_{433}$s are the same or different;

m represents an integer of from 2 to 4; and the carbon linking group is linked to any one of C atoms in $X_{431}$, $X_{432}$ and $A_{431}$ to $A_{437}$.

19. The compound according to claim 16, which is a compound represented by formula (4-4):

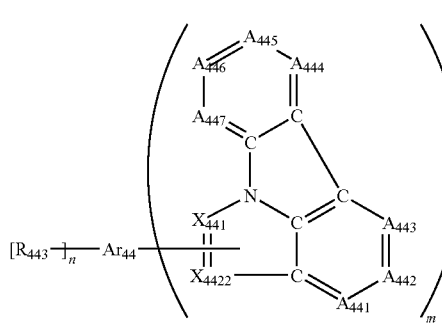

(4-4)

wherein each of $X_{441}$ and $X_{442}$ independently represents C—$R_{441}$;

$R_{441}$ represents a hydrogen atom or a substituent, provided that a plurality of $R_{441}$s are the same or different;

each of $A_{441}$ to $A_{447}$ independently represents a nitrogen atom or C—$R_{442}$;

$R_{442}$ represents a hydrogen atom or a substituent, provided that a plurality of $R_{442}$s are the same or different;

$Ar_{44}$ represents an aromatic hydrocarbon ring or an aromatic heterocyclic ring, and a size of the ring is from 5-membered to 6-membered ring;

$Ar_{44}$ is linked to any one of C atoms in $X_{441}$, $X_{442}$ and $A_{441}$ to $A_{447}$;

$R_{443}$ represents a hydrogen atom or a substituent, provided that a plurality of $R_{443}$s are the same or different;

m represents an integer of 2 or more; and n represents an integer of 0 or more.

20. The compound according to claim 16, which is a compound represented by formula (10-1):

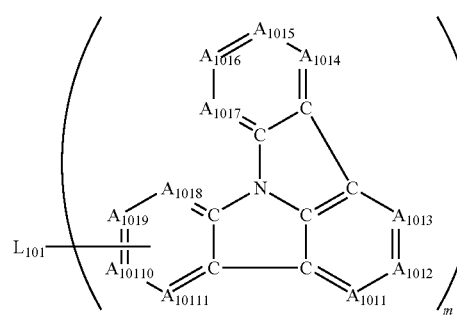

(10-1)

wherein each of $A_{1011}$ to $A_{10111}$ independently represents a nitrogen atom or C—$R_{1011}$;

$R_{1011}$ represents a hydrogen atom or a substituent, provided that a plurality of $R_{1011}$ are the same or different;

$L_{101}$ represents a single bond or an m-valent linking group and is linked to any one of C atoms in $A_{1011}$ to $A_{10111}$;

when the linking group as $L_{101}$ is an aromatic hydrocarbon ring group or an aromatic heterocyclic group, a size of the ring is from a 5-membered to 6-membered ring; and m represents an integer of 2 or more.

21. The compound according to claim 20, which is a compound represented by formula (10-2):

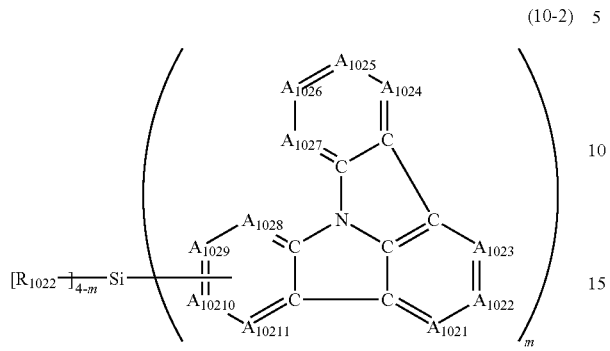

(10-2)

wherein each of $A_{1021}$ to $A_{1021}$ independently represents a nitrogen atom or C—$R_{1021}$;
$R_{1021}$ represents a hydrogen atom or a substituent, provided that a plurality of $R_{1021}$s are the same or different;
$R_{1022}$ represents a hydrogen atom or a substituent, provided that a plurality of $R_{1022}$s are the same or different;
m represents an integer of from 2 to 4; and
the silicon linking group is linked to any one of C atoms in $A_{1021}$ to $A_{10211}$.

22. The compound according to claim 20, which is a compound represented by formula (10-3):

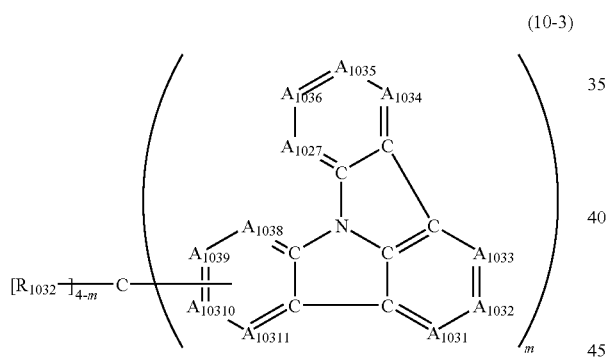

(10-3)

wherein each of $A_{1031}$ to $A_{10311}$ independently represents a nitrogen atom or C—$R_{1031}$;
$R_{1031}$ represents a hydrogen atom or a substituent, provided that a plurality of $R_{1031}$s are the same or different;
$R_{1032}$ represents a hydrogen atom or a substituent, provided that a plurality of $R_{1032}$s are the same or different;
m represents an integer of from 2 to 4; and
the carbon linking group is linked to any one of C atoms in $A_{1031}$ to $A_{10311}$.

23. The compound according to claim 20, which is a compound represented by formula (10-4):

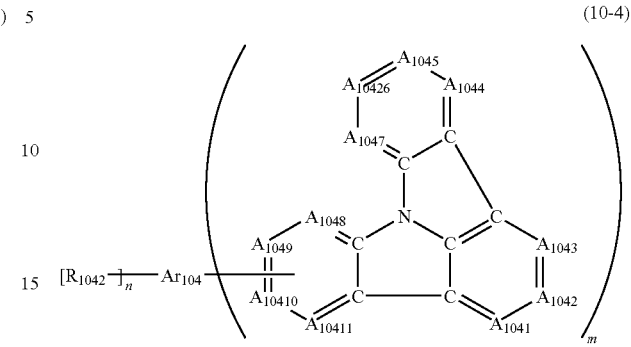

(10-4)

wherein each of $A_{1041}$ to $A_{10411}$ independently represents a nitrogen atom or C—$R_{1041}$;
$R_{1041}$ represents a hydrogen atom or a substituent, provided that a plurality of $R_{1041}$s are the same or different;
$Ar_{104}$ represents an aromatic hydrocarbon ring or an aromatic heterocyclic ring, and a size of the ring is from 5-membered to 6-membered ring;
$Ar_{104}$ is linked to any one of C atoms in $A_{1041}$ to $A_{10411}$;
$R_{1042}$ represents a hydrogen atom or a substituent, provided that a plurality of $R_{1042}$s are the same or different;
m represents an integer of 2 or more; and
n represents an integer of 0 or more.

24. An organic electroluminescence device, comprising:
a pair of electrodes; and
at least one organic layer including a light emitting layer, the light emitting layer being provided between the pair of electrodes,
wherein at least one layer of the at least one organic layer contains the compound represented by formula (4-1) according to claim 16.

25. The organic electroluminescence device according to claim 24,
wherein the light emitting layer contains a phosphorescent material.

26. The organic electroluminescence device according to claim 25,
wherein the phosphorescent material is an iridium complex or a platinum complex.

27. An organic electroluminescence device, comprising:
a pair of electrodes; and
at least one organic layer including a light emitting layer, the light emitting layer being provided between the pair of electrodes,
wherein at least one layer of the at least one organic layer contains the compound represented by formula (10-1) according to claim 20.

* * * * *